US008652842B2

(12) United States Patent
Platzer et al.

(10) Patent No.: US 8,652,842 B2
(45) Date of Patent: *Feb. 18, 2014

(54) HUMANIZED IMMUNOGLOBULIN LOCI

(71) Applicant: Therapeutic Human Polyclonals, Inc., Mountain View, CA (US)

(72) Inventors: Josef Platzer, Geretsried (DE); Roland Buelow, Palo Alto, CA (US); Wim van Schooten, Sunnyvale, CA (US)

(73) Assignee: Therapeutic Human Polyclonals, Inc, Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/779,585

(22) Filed: Feb. 27, 2013

(65) Prior Publication Data
US 2013/0189774 A1    Jul. 25, 2013

Related U.S. Application Data

(62) Division of application No. 12/511,188, filed on Jul. 29, 2009, now Pat. No. 8,410,333, which is a division of application No. 10/893,483, filed on Jul. 15, 2004, now Pat. No. 7,585,668.

(60) Provisional application No. 60/487,733, filed on Jul. 15, 2003.

(51) Int. Cl.
*C12N 5/10*        (2006.01)
*C12N 5/0781*      (2010.01)
*A01K 67/027*      (2006.01)

(52) U.S. Cl.
USPC ............................ 435/326; 435/328; 800/14

(58) Field of Classification Search
USPC ................................... 435/326, 328; 800/14
See application file for complete search history.

(56) References Cited

U.S. PATENT DOCUMENTS 8,410,333 B2 *   4/2013   Buelow et al. ................. 800/14

FOREIGN PATENT DOCUMENTS

| EP | 0 491 057 | 10/1991 |
| EP | 0 583 980 | 8/1993 |
| WO | WO 92/03918 | 3/1992 |
| WO | WO 97/16537 | 9/1997 |
| WO | WO 00/46251 | 8/2000 |
| WO | WO 00/75300 | 12/2000 |
| WO | WO 01/19394 | 3/2001 |
| WO | WO 02/12437 | * 2/2002 |
| WO | WO 2004/003157 | 8/2004 |

OTHER PUBLICATIONS

Bruggermann, et al. "A Repertorie of monoclonal antibodies with human heavy chains from transgenic mice", Proceedings of the national academy of sciences, vol. 86, No. 17, pp. 6709-6713, (1989).
Bruggermann, et al., "Strategies for expressing human antibody repertories in transgenic mice", Immunology, vol. 17, No. 8, pp. 391-397, (1996).
Butler, "Immunoglobulin Diversity, B-cell and Antibody Repertoire Development in Large Farm Animals" Rev. Sci. Tech. Off. int. Epiz. 17(1):43-70 (1998).
Database EMBL Jul. 16, 1998, "rabbit Ig Germline CL42.Vh25 and CL. 42Vh34 Genes, VHA3 Allotype, 5'end" XP002393777 retrieved from EBI Database Accession No. M12180.
Database EMBL, Sep. 23, 2003, Acc. No. AY386697: http://www.ebi.ac.uk/ena/data/view/AY386697[Jun. 12, 2012] 21 pgs.
Dufour et al., "The Sheep Ig Variable Region Repertoire Consists of Single $V_H$ Family" Journal of Immunology, 156:2163-2170 (1996).
Etches et al., "Strategies for the Production of Transgenic Chickens" Methods in Molecular Biology 62:433-450, 1997.
Genabnk, AY495826, Platzer, J., Direct Submission: Nov. 2003. THP Gmbh, Am Neuland 3, Bernried 82347 Germany.
Genbank, AY495827, Platzer, J., Direct Submission: Nov. 2003.THP Gmbh, Am Neuland 3, Bernried 82347 Germany.
Genbank, AY495828, Platzer, J., "Sequence Analysis of 0.4 Megabases of the rabbit Germline Immunoglobulin Kappal Light Chain Locus" Direct Submission: Nov. 2003. THP Gmbh, Am Neuland 3, Bernried 82347 Germany.
Ilesse et al., "V(D)J Recombination: A Functional Definition of the Joining Signals" Genes and Development, Cold Spring Harbor Laboratory Press, Plainview, NY, US, vol. 3, No. 7, (1989), pp. 1053-1061 XP009043633 ISSN: 0890-9369.
Hole et al., "Identification of Enhancer Sequences 3' of the Rabbit Ig $_K$ L Chain Loci" The Journal of Immunology 146(12):4377-4384 (1991).
Jakobovitis, et al., "Analysis of homozygous mutant chimeric mice: deletion of the immunoglobin heavy-chain region blocks b-cell development and antibody production", Proceedings of the national academy of sciences, vol. 90, No. 6, pp. 2551-2555, (1993).
Knight, K.L., et al., "Generating the Antibody Repertoire in Rabbit", *Advances in Immunology*, vol. 56 (1994) pp. 179-218.
Lauster et al., "Promotor, Enhancer and Silencer Elements Regulate Rearrangement of an Immunoglobulin Transgene" EMBO Journal 12(12):4615-4623 (1993).
Lee et al., "A Highly Efficient *Escherichia coli*-Based Chromosome Engineering System Adapted for Recombination Targeting and Subcloning of BAC DNA" Genomics 73:56-65 (2001).
Mansikka et al., "Bursectomy of Chicken Embryos at 60 Hours of Incubation Leads to an Oligoclonal B Cell Compartment and Restricted Ig Diversity" Journal of Immunology ,145(11):3601-3609 (1990).
McCormack, Wayne T. et al., "Chicken IgL variable region gene conversion display pseudogene donor preference and 5' to 3' polarity", *Genes & Development 4*: (1990) pp. 548-558.
Muyrers et al., "Techniques: Recombinogenic Engineering-New Options for Cloning and Manipulating DNA" Trends in Biochemical Sciences, 26(5):325-331 (2001).
Muyrers et al., "Rapid Modification of Bacterial Artificial Chromosomes by ET-recombination" Nucleic Acids Research 27(6):1555-15557 (1997).
Pain et al., "Chicken Embryonic Stem Cells and Transgenic Strategies" Cell Tissues, 165:212-219 (1999).

(Continued)

Primary Examiner — Anne Marie S Wehbe
(74) Attorney, Agent, or Firm — Ginger R. Dreger; Arnold & Porter LLP

(57) ABSTRACT

The present invention concerns methods and means to produce humanized antibodies from transgenic non-human animals. The invention specifically relates to novel immunoglobulin heavy and light chain constructs, recombination and transgenic vectors useful in making transgenic non-human animals expressing humanized antibodies, transgenic animals, and humanized immunoglobulin preparations.

3 Claims, 49 Drawing Sheets

(56) References Cited

OTHER PUBLICATIONS

Reynaud et al., "Somatic Hyperconversion Diversifies the Single $V_H$ Gene of the Chicken with a High Incidence in the D Region" Cell 59:171-183 (1989).

Reynaud et al., "Hypermutation Generating the Sheep Immunoglobulin Repertoire is an Antigen-Independent Process" Cell, 80:115-125 (1995).

Volgina et al., "A Single 3'áhs1,2 Ehancer in the rabbit IgH Locus" Journal of Immunology 165:6400-6405 (2000).

Ros, et al., "Sequence analysis of 0.5 Mb of the rabbit germline immunoglobin heavy chain locus", Gene: An international journal on genes and genomes, vol. 330, No. 14, pp. 49-59, (2004).

Sang, "Transgenic Chicken-Methods and Potential Applications" Tibtech, 12:415-420 (1994).

Sherman et al., "Transposition of the *Drosophila* Element Mariner into the Chicken Germ Line" Nature Biotechnology, 16:1050-1053 (1998).

Yu et al., "An Efficient Recombination System for Chromosome Engineering in *Escherichia coli*" PNAS, vol. 97, No. 11, pp. 5987-5983 (2000).

Zhang et al., "Risk of Tuberculosis Infection and Tuberculous Meningitis after Discontinuation of *Bacillus* Calmette-Guerin in Beijing" Am J Respir Crit Care Med 162:1314-1317 (2000).

Chen Su et al. "Fifty-million year old polymorphism at an immunoglobulin variable region gene locus in the rabbit evolutionary lineage", Proc. Natl. Acad. Sci. USA 96:9710-9715, Aug. 1999.

* cited by examiner (a)

(b)

Figure 9b Seq ID 186 agaggatcctattaattgtttgttaattaagaggacaggaattcagtgtcaggggggctgctctttgcttcccaatgtgtaccactgaa
gcctctctggatttatcagagatactcaatggactcttaacagcactgtggcacctgacctcctgctgccttcagcctcccttcctgg
ctggtgtgcttgtgttgaggagctgtgggaggctggtgcagttctgtgggatgaggtaaggccagctgaatagcctgggggctg
gtcaggggggcttagtgagaggagcagggctggggaatattgtgaacagcaggtggtgccactgctattctgaggaaggaggc
agcttctgcaaatgctttgcaatgcaggatgacaaagtgcttctgctagctctaggcccttgctcatggctgtgatggtgcttaacg
gtgccagagtgcagacaaatagatgtgtacagctgctctgggagtaacaacaacaactatggctggtaccagcagaagacacc
tggcagtgcccctctcactgtgatctatcaaaacacaaagagaccttcaggtatatctttatacttcagctggtaccagcagaagac
ctctggcagtgcatctgtcgctgtgctgaaaccaacagacacaccaacaccacaggacagcttcttgcagttctccatctcctggt
gcagcttcatgagcacgttaaccatcgtggggattcaagctgaggatgtagctgtctatccctgtggcaacagggacagcagtg
gtaagcctggtgaggtgatacagggagatgtcaaaaaaaagaaaaacccaacatgtatgggttaaaaatggaggctctctgc
cctttctctcatggctgagctgggctgtgcagtgaggtaagttcctgtctcgtctgcaaagcactgtctgaatggtctccctattgtg
tgttgtggtgcatgagggattctggggacagagggcatttgtctgtccctataaaggcccaaagcccctggctgtgtacagtaagt
ccgcctggggcacctgagctgtgggcaggtactgccaggagaggggctcaggccatgatccaataccaatggctctgtgtccc
catgctaataggcctatgctgcagcccatcactccctcttaaacccctcttaaacttcctacagttctaagttctatctctctcctcca
attaatcatcgtcaccatacagcatcagtgctgtcatcccagttcccccagtaatagacagcctcgtcctcgacttggacccccagtg
atggttaacgtgcttgtggttctgcctggggagccggagaatcgtgaagggatgttcgagggtctgttggtgttgtcatagatcac
agtgacaggggcactgccaggtgccttctgctggtaccagccatagtagctgctatccccggagcaggtgatctcaacggtttct
cccgggttcgctgacaccgaggccggctgagtcagaggagagagggggagaaaatggagctcagtgagtgtgcgacacaca
cagccctcagcgtactgcggtgggataatacttctgagcacacagtcccaaatggaacctcaggactctctcatctgcttcaggat
gaacaatgtctatggctgctcccagcagaggactcctggcagtgcccttgttgctgtgatataggggggccagcaggagaccctc
agacgttgctttgtactttccatgttccaaatcctgctgcatgcacaaattaactctcgtggagattcaagccaagggtgagactgtc
tattactgtggtgcctgggaaggcagcagtaatcctggtttggtgatacagggagatgtgcctcccccaaaaaaaacccaaaca
aacaaaagcatatataggggggtaaaaatggagttttctgcccatctgtctcacagccaagctgggctgtgcagctgcggcagg
ttcctggcctctctgcaaagctctgtttgtgaatggccttccttcctcttgtaccttgtggtgcaggaggagattgtggggacagaag
ccacttctccttgtccctacaaaggcacagcactgtgtcatccccagccctcctccatgttactgctggcagtcccgtcctcctgctt
ctgaagagacatggatgtaggtgaggtctcttctgcaacagtggtgttcatcaccccacagctgccaggtgagggctgtgtgtgt
cggacatttggctgagctccattttctctcctgtccctctccaggttccctggtgcaggcagcgctgactcagccatcctcggtgtc
agcaaacctgggaggaaccgtcgagatcacctgctccgggggtagcaacaactatggctggtatcagcagaagtctcctggca
gtgccctgtcactgtgatctatcaaaacaccaagaggccctcgggtctctcttcataactttcttgttcctcatctggctctgcaaac
acgttaaccatcactggggtccaagccaaggatgaggctgtctattactgtggtggctgggatagctgctgcctgagtcagtgct
gcctgcaccagggaactgggagaggagaggggggagaaaatggagttcattgagtccctgatatacggagtccttgctaggc
aatgagataagacagctgagcccacagaccatcttttactacagctggtaccagcagaagacgcctggcagtgcatctgtcact
gtgatctatgctgacaccaacagacccaccaacaccacggggcagcttctcacaatcctacacgttctggtgcagcttcatgagc
acattagccattgtgggggactcaagctgaggatgtggctgtctatttctgtggcagcagggacagcagaggtaagcctggtgag
gtgatacagggagatgtcaaaaaaaaatgaaacaacatgtataggagttaaaaatggaggttttctgctctcttctctcacaggtga
gctgggctgtgcagtgagatgagttcctgtccctctgcaaagcactgtctgaatggtctccctgctgtgtgttgtggtgcatgagg
agagtctgaagacagagggtacttctccctgtccctgagaagctgctgcatggtgtcatcccagccctgctgcatgttacactgt
ctgccctgtccttctgatgccgaagctgcttccatgctgggatgctctgggctgagctctgattctccaaaatggcagtggtttcttct
gatggtggtggtattcctcattctactgctgtgcagggagggctgtgtgtgttggctacccactgagccctgttttctctcctctcc
ctctccaggttccctggtgcaggcagcgctgactcagccggcctcggtgtcagcgaacctggggaggaacagtcaagatcacct
gcaccagggatgacagctggtatggctggcacctgcagtgaggggcattgaggctgggaacaatgcagtgctgtgcctttgca
ggaacagggataacggggcactggacccagaattgattactgaatgaaaaggttcagtaagagaggacatgcgtgtgatgtac
agtctggcagaagggactggattctccctcagccctgactcaacaagggcagaaagccttggttttgaatcgcagtctgcatgtc
accccacatctccccacatcactataccagcactattgctcctgtcccaatcaccacagtaatagacagcctcgtcctcgacttg

Figure 9b Seq ID 186 (con't)

```
gaccccagtgatggttaatgtggccgtggagccggatttggaaccggagaatcgtgaagggatgtccgagggtctgctgctgct
atcataaatcacagtgacaggggcactgccaggtgatttctgctggatccagccatagtagctgctgctaccagagcaggtgatc
ttgacagtttctcctgggtttgctgacactgaggttggctgagtcaggttactttgggacctgagccagactgtacctgtccctacaa
aggtacagcactatgtcatccccagccttgcttcatgttgctgctgcaagccctgttctcctgctggagctgtctctgtgctgggatg
ctctggtctggactctcatcttctaatgtgccggtggccatgactgaggtttcttctcctttaatagtggtgctccctttcccactgttgt
acgcagagggctgtccatgtgggtattccctgagccccacttctctcctctccctctccaggttccctggtggaggcagaactc
attcagccgacctcggtgtcagcaaaccctggggaaactgtcaagatcacctgcagtggaggtatcggccagtggtatggctgg
taccagcagaagtcacctggcagtgtgcctgtcactgtgatcaatgctaacaccaacagaccctcgaacatcccttcacgattctc
cggttcgctctccgtattcacacacacattaaccatcactggggtccaagctgaggatgaggctgtctattactgtggtgcctacga
cagcagctatgttggtatagtgccaggggagatgaggcggtgaattgatggccagagctgaaaatgatgggtttccacccttct
ccattatgactttgttgagatctcttctcatgatggtcttccctggttttcctgtggttggaaggagcagaaggcactggcagggtc
ttgctgggagagctggcaatagcagggatagtggatgccccacatggaagaaagggacacagctatggccacttctgatgaga
ggtgtccagagcacagcagcacatccctgtgcttcagacatctcctgtgccctggggtgtggaagggaatgcattcatagcatg
gccaggtggaggtaagagtaacatgcctactgcagtaattctgcacatagagaaggaagaaagacagaaaatcttcctacagtt
ctaagtttcctctctcttctccaattaatcatcatcaccatacagcttcagtgctgctatcccagctcccacagtaatagatagcctcgt
cgtcggcttggaccccagtgatggttaatgtgcttgtggagccggatgtggaaccggagaatcgtgaagggatgttcgagggtc
tctggttgttgctatagatcacagtgacaggggcactgccaggagacttctgctggtgccagctatagtaataacttccatcatcgc
tgccaccccgagcaggtgatctcgacggttcctcccaggtttgctgacaccgaggccggctgagtcagcgctgcctgcacc
agggaacctggagagggagaggagagaggggagaaaatggagctcagtgaatgtgtgacacacagccttcagcatgctgca
gtgggactgagcaccagcacttgctcagctccattttctccaggttccctggtgcaggcagtgctgactcagctggccttgatgtc
agtgcatctgcgtgttactgattacaggttcagctgctctgggagtagtggcgactatggcagtaactgtcagggcagcaccagc
aaaaggcatctggcagtgctcctttctatgtgctgtacctgaacaccaacagaccctcgaacatcccttgcaattcaccggttcca
aatctggctccacagccacattaaccatcactggggtccaagccggcgacgaggctgtctattactgtgggagtgaagacagca
gcggtactggtgccacagtgacacagagcaatggagatgtgatacacaaacctgtcagtgcagggaacagttggcactggcac
tcatctactcctggactcacaactactatggctggtaccagcagaagtcacctggcagtgccctgtcactctgatctatgctaaca
ccaacaggccctcgaacatcccttcacgattctccggttctggatccggctccacaaacacattaaccatcactggggtccgagc
cgaggacgaggctgtctattactgtggtggctacgacggcagcactgatgctggtagtgacggggagatgtgaaactgaggta
cagccctgaattaaaaacgtctgttttctgcctttctcccttatgtttgttctgggctgtgtcactgaggcagttttccctctgcatggcc
atggctttgatcatcttttctgtcctgcctcagtgtttggaaggtgactctcccagttaccgcggaggaaccatgaagatcatttgctc
ctggtgtagcagtagctatggttgtggctgcatctggcttcaacagcaagttaaccattactcatgttgaaaccaaggatgaggctg
tctaagatgtgtgagctagcatagcagtgaggctggtagagtgacaaagggaagcatagctgtgatgtctacttctggagtgcac
tggggcatgaaagcgaaaacagtcaaagccacaaccacacggagggaacaggaacatgtctacagccataactctgcgtggc
caaaatgctgaaagtcagaaaaccagcagggagcggggctgggtgcagtgcatgccaaccctttgtggggacagctgtagaa
catggaattcaatctcagtggagtcgaaccaattggcaggctgtcagcagaggcattccccagtgctcccctttgtttaatgtgaaa
ttacaaacaacgctgccaggcaacaaactgtattgatctgcttgagggtaggaaggccttgtagacagatgaggataggcaaaa
atcaatgggctgtgtcaaacccattgacgttcaagaacgttaagtcccagggcctgcacttaggtcataacaacacaaggcagca
gtgtaggctgaagagatggttgattagagggttctgttagaatggttcaattctgtgatcatgaagataacttccaaacaaaattggt
gtaggatagggataaggtgctctggccccagaatcacctgcaacaaaaaatacagcagggagggcataaacaattgcggccct
gcagaggggcagggcatctgcctcagccccattagtgaagggatgcttaagagtctaccggtgttaccatagatcacagtgaca
ggggcaccgccaggagacttctgctggtaccagccataagcatcgctactgcctgagcaggtgatcttgacggtttctcctgggt
ttgctgacatgaaggccagctgagtcggtgctgcctgcaccagggaacctggaggggagaggagagaaaatggagctcag
taagtgcctgacacgcaacacccagtgccagaagatagcactgatccccaagacaaggagaccatgcatgccaaagaggttc
ctctttctctcccacttcctctcagtccggctctagggtctccctccttcctcctgctctccttcaccctgtacatcagatcccagggc
tttgctgcatttctgctcctgcaggcattgcctggggccctgtggcaagaccagggatcagtcactctgggagtagccatgagtat
```

Figure 9b Seq ID 186 (con't)

ggctggttccaggagaaacctggtagtggtgctgtgactgtgatccacagtgacaccaacagaccctcgaacatcccttcacaat
tctccagttccaccccgcagtgccaccaccagcatatccactatcagtgctgctgtcgaagctcccacagtaatagacagcctcg
tcctcggcttggaccccagtgatggttaatgtgcccgtggagccggatgtggaaccggagaatcgtgaagggatgcccgaggg
tctctcatcatcccagtagatcacagtgacaagggcactgccaggagacttctgctggaaccagccatagctatagctgccccca
gagcaggtgatcttgacggtttctcctgggtttgctgacaccgaggccggctgctgagtcagtgctgcctgcaccagggaacct
ggagagggagaggagagaggggagaaaacggcaatcagtggctgcctgacatacacagcttccccccgcaaagcagcagg
acagaggccccatgcccatacaggcccaggtcacctgaactgttggtgaccatcactagtaggagaggggcccagaccatgg
tgctactccaacagttgtgctatggaccccaactccctttagacccccaccttctacagcacagccacctcctgcaagcctggt
gtccatggatactggccaccccatcccatgctcccttgcctcctgtagccattttccttgatctcagaagaccaatcatggttagc
cattactgggatccaaaatgagcacaagactatctactactgcggtagcttgggaaacagcactgatactggtagaatggcacag
ggagatgggaaactgagttacaaacctgagttcaaaatggaagctttctgcacttactgcattatggctggacagggctgcaggg
gctgagtcctgtttctgtcctctctgcacggccctgactgtaaatggcctcctctctcttcttaaccacaatgtacctgtccctgccca
ggcacagcactacgtcaaccctagccctgctccatgttgctgctgtgagctcctatctccttctagagctgcctttgtgctgagatg
ctctgtgctgggctcttgcccacaaacatacctatgtctgtgactgaggacccttctcctctgatggtagtgcttcccctgcggttgg
ggagggcagggcaaattgggcacctgttgagcccatttactccctctccctatgcaggttccctggtgcaggcagcgctgact
ctgccagactcattatcagcaaacctgggagaaactgtcaggataacctggtctggaggtagctatgattatggttggcaccagc
agaaatcacctggcagtgccctgtcactgtgatctataacaacaacaagagaccctcagacatcccttcacgattctccggtgc
cctatccggctccacagccacattaaccatcactgggggtccgagccgaggacgaggctgtctatttctgtggtgcctgggaaag
cagcagtaatcctggtatggtgataggggcgatgtggggggaaaaaaaaaaaaaaaaagacacatataggggataaaaat
ggaggttttctgcccatctgtctcacagccaagctgggctgtgcagctgaggcaggttcctggcccctctgcaaagcactcgttgt
gaatggtctccctcttgtacagtgcagtgcaggaagagataccaggtatgtccagacctgtttgctgttactgctggcagacctatc
ctcctgctttgaagaggcatggatgtctgtgaggcctcatctgccagggtggtgttcctcatcccaccccctgccaggtgagggct
gtgcgtgtcaggcaaacactgagccccattttctccctctccctctccaggttccctggtgcaggcagcgctgactcagccggc
ctcagtgtcagcaaacctgggaggaaccgtcaagctcacctgctccgggagtagcagtggctatggttatggctggtaccagca
gaagtctcctggcagtgcccctgtcactctgatctatagcaacgacaagagaccctcggacatcccttcacaattctccggttcta
aatccggctccacgggcacattaaccatcactgggggtccaagccgaggacgaggctgtctatttctgtggggaatgcagacagca
gcagtactgataccacagtgactcagatgtaatacacaaacctcccggcagtgcaaggagcagataatacccttaactgtctgtct
tacaggttccacctccatcaatacccatgctgcagggctcaggtcctcttaggctgccaggctgcaccctgctggctccctccc
cactaccctacacccacccttttgcagtgtccctgcatgcactggggcaacacttcctcacctgtccgctccctgctggagggcc
acagccacctggttgatacatcagcatagcaccagttcttccccaagctggccctccttggactctctactgagcccccatttctc
ccctctcctctccaggttccctggtgcaggcagcactgactcagccagcctcagtgtcagcaaacctaggagaaactcaggatc
acctgctctgggggtggcagtaacaatgcttatggctggttccagcagaaggcacctggcagtgcccctctcactgtgatctact
ggaatgacaagagaccctcaaacatcccttcacgattctccggttccaagtccggctccacagccacattaaccatcactggggt
ccgagccgaggacgaggctgtctattactgtgggagtgcagacagcagtggtgctggtcccatggtgacacacagcagtgag
gaagcgatgcacaaacctcctgacagtgcaaggagcagccggcaggttttgctgtctctgtttgatggtggcacaggacctcac
cacagccctaccttcactgtcctgcaatatgggtggctgtgcacggtgtcctgaacacgtcccaacaagatgcacagcactgcat
caggcccagcccctgcctgtagcagctgatgcccttgtccagcttctgcctgagctgcctctgtgctgggatgctccatgctgag
ctctgatcctccaaagtgcccatagctgtggctgggatcccttctgctctgatggtggtggcacattgcaggaacagagcccaga
ccagaacagctcagtacagagccagctccagcagggagagaatgggggctgccagcagcaatgtggaacagctggggatgg
cacagagctgtgccttttcagggacaggtacagtgtgactcagtacccagagtaacctctcatacaactacatataccaaggaag
gcatttacaagcatggccatgcagagaagatataaatcatcctcagtctcacagacctgctcagccataaggcatcaagggtgaa
aaacctctattttttttttaaccctgatcaatccatcagttcctccacctcccgctgaggcaataccagcataagtgctgctgtcgtagcc
accacagaaatagacagcctcgtcctcggcttggaccccagtgatggttaatgtggctgtggagccggatttggaaccggagaa
tcgtgaagggatgtccgagggtctgttgttgttgttatagatcacagtgacaggggcactgccaggagacttctgctggaaccag Figure 9b Seq ID 186 (con't)

ccgtagctgccactaccccggagcaggtgatcttgacggttcctcccaggtttgctgacaccgaggccggctgagtcagtgct
gcctgcaccagggaacctggagagggagagaaaacagggctctgtgtgtgtctgacacgcacagcctccttgtttggcagtgg
ggtgaggctgctgagcacacagacacacatgggacagcaggagacccacatctgctccaggattgacatctatggctggtacc
agcagaagatacctggcaatgccccatcactgggatccatgctaacactggtagacccacaggcgttctcttaccattctctggg
gtccaatccaggcctacacacatgaactgtcacactaactaccactgtggtctaagctgtggagaacactgcccattactgcggt
ggcaatgacaggagccaaggcctgaggatggcacttatcaccaggatagcaggacaaggggttcacaagaaaaaaagaaag
gttcttttttcctctcccgcttcctctcagtccagctctgtggtctcttctccttcctactgctctccttcaccctgtacatcagatcccag
ggcttcgctgcatttctgctcctgcaggcattgcctggggccctgtggcaagaccagggatcagtcagtccgggagtagcaatg
agtatggctggttccaggagaaacctggtagtggtgctgtgactgtgatccacagtgacaccaacggaccctcgaacatcccttc
acaattctcctgttcccctcggctccacgcacgagctaaccatcactggggtccaagctgaggacaaggctgtatattaccgtg
gagactgaagagcagcagtgatgctgtattttgacaatgtgtagtaggaacataaacacagccacattcacagtaaagttttcagg
ccaccttccttggtccccgagctttgggaattgtgacttatgttactgttttgggaattcaggaggccttgtcctatctgaatggccaa
gaccttgactgttacccagatcatattccaggaatgagggtgatactgggtatagaccccatcatccttgtccctctccaggttcc
ctggtgcaggcagcgctgactcagccggcctcggtgtcagcaaaccaggagaaaccgtcaagatcacctgctccgggggtg
gcagctatgctggaagttactattatggctggtaccagcagaagtctcctggcagtgcccctgtcactgtgatctatgacaacacc
aacagaccctcgaacatcccttcacgattctccggttccccatccggctccacaaacacattaaccatcactgggggtccaagtcg
aggacgaggctatctatttctgtgggagctacgaaggcagcactagtgctgtatggtgacaatgattaaaaggaactgaattaata
aattataagcctgttttctgcccatcttccttttggccatgcagaactgtggccatagcagtttcctgttccatctgcatggccatgcta
tgaatgcactccctccacaccgcagggcacaggagatgtctgaagcacagggatgtgctgctgtgctctggacacctctcatca
gaagtggccatagctgtgtcccttctccatgtggggcatccactatccctgctattgccagcactcccagcaagaccctgcca
gtgccttctgctccttctaaccacagcagtgggtgctgcccccagagctgctcctctggatgctgtgccccacatttcctgaacac
acactgcccatccagcaatgtgggacagggaacaccacagcaggaagagacctcaatcacagccatagtggaggcagacag
aaacctgtcattttagctctagacatcacatcactccctatctccctgtgtctctgtacctacaaaactgctgtcataggccccact
aggacaggaacatgaatgggggctctgcaaaggcagcgccacagcagctgtggacccagagagcagaactgactgccctcaa
cagctccgccatgcagggagatgtgcagcaacaaggagggaggaaatccaacagtgccgccaccagcataaccagcact
gctgtcgtagctcccacagaaatagacagcctcgtcgtcggcttggaccccagtgatggttaatgtgtttgtggagccggatgtg
gaaccggagaatcgtgaagggatgttcgagggtctcttgctgctttcatagatcacagtgacaagggcactgccaggagacttct
gctggtaccagccatagtagctgctgctaccaccccccggagcaggtgatcttgacggtttctcctgggtttgctgacaccgaggc
cggctgagtcactgctgcctgcaccagggaacctggagagggagaggagagaaaatggggctcagtgcctgacacacactg
ccctcctcctcctcatggggaggagaccccagagcacacaagcacacacagaatattcaaacaccgacttctaatccatgct
taacagcaactatgactggtacaagcagaagactcctgacaataccactggcactttgtaatacctccacaataagcccccctctc
tcctctccctctccaggttccctggtgcaggcagcactgactcagccggcctcggtgtcagcaaacctgggaggaaccgtcaag
atcacctgctccgggggtggcagcagctatggttacagctggcaccagcagaagtctcctggcagtgcccctgtcactgtgatct
atagcaacgacaagagaccctcggacatcccttcacgattctccggttccgcatccggctccacagccacattaaccatcactgg
ggtccaagtcgaggacgaggctgtctattactgtgcgaacttcgacagcagcagtactgctgttagtgacggggggggagatgtg
aaactctctacagccctgaattaaaacatggatgttttctgcctttctccctcaggatcacgctgggctctgtcactcaggcaggttc
ccctctgcatggccacggctttgaacatctttcctgttctgcctcattgtataggactctcccagtacctggaaacaccaaaaagatc
atgtgctgcaggggtagcagcagctatggttatggctaatagcagatgacacctggcagtgccccatcactgtgatctacagtaa
caccaagagatccttcatgattctctggttccatatcccacgccacacacacacactatcactggggcccatgccaaggatga
ggctgcctattactgtgtaaatgcagacaacagttgtacagtactgcttcccactgacacagagcagcaggtacaactgatgcact
aacctcctgccagtgcagggagcagctggctcttttttgctggctctgtttgatggcggtgctggttcctaccatggcccttccctcat
tgccctggactacatgtggcagggcaaaaatcacatcccagcactgacagcagggaacctgtggaccgctgagcagccagg
ccaaagctcctacttagaggggatgtttcccatggcacaaggctgggctggctgtgtttctcttctggcacgagggcagccaca
gaatctttcagatcaggatgattgttgtgatctgctcctacctcagctcaactggcatcacctacagcacagtgcccaggcctgtgt

Figure 9b Seq ID 186 (con't)

```
gcaggtggctgtcagagatctccaaggaggagactccatgatctctccgggcagcctggatcagtgctacattacctgcggagt
aaggatgtgactcctgactctggccagacagaacctctgcgttcagtctgtgccactgcctcctgtactggtgctgaatgctgctg
gaaaaagcctggctctgttcactttgcaccctcctttcaggttagcgtaagggagaggagagaaaataggggctcagcaattgccc
aacatgcacagccctcaccaggctgtcagatgaggcacgcaattccacaaggacacatggggtagcaggatacccacatctgc
tccaggattgttaacaactacggctggttccagcagaagtcacctggcagtgctcctgtcactgtgatctatggtagcaccagtag
accctcaaacatcccttcacgattctccggttccgagtccggctccacagccacattaaccatcactggggtccgagccgagga
cgaggctgtctattactgtgggagtgcagacagcagtggtgctggtcccatggtgacacacagcagtgaggaagtgatgcaca
aacctcctgtccgtgcaaggagcagctggcaggttttgctgtctctgtttgatggtggcacaggaccccaccacagccctaccttc
actgacctgcaacatgggtggctgtgcacggtgtcctgaacacgtcccaacaagatgcacagcactgcatcaggcccagcccc
tgcctgtagcagctgatgccettgtccaacttctgccagagctgcctctgtgctgggatgctccatgctgagctctgatcctccaaa
gtgcccatagctgtggctgggatcccttctgctctgatggtggttgcacattgcaggaacagagcccagaccagaacatcttagt
aaggaggcagctccagcagcagcagaacggggctgccagcagcagggaatgatgctgtgccacagtaggaacagggacca
agaggatcacttcccacgcaataaagtataaaagagagggcattcaaaaacacagccatgcagagcagagagaaacctgact
cagccccacagtcctgctcagccttaagtcagcaagtgcagaaaacctccatttcaactcaggtctgtaactcagttccacatcct
cttttgtctctataccagcattagtgctgctatcccagccaccacagcctcatcttctgaccttagtgacaactaaccacaattggtctt
ccagggcccagggaaatagctgcactgggacaggagctgccagtgaccatgaggttctgcatgagtgggctgtgttgtgggca
gttcagggtataaagaaaggagttggagtccatggcatagacccattggcataaggatgtgcatctgctgggatcacaccatgg
cctgtgccctctcctgctggcagtgctgacccacagctcaggtgccccaggaacaccggttgtgcccagccttgggcactgg
gccccatcccctgctttttaagacttggcatcaattcaccacaacacctctctgcagcaccataccaacatgctgctgtccctg
ctcccacagaaatagacagcctcgtcctcggcttggaccccagtgatggttaatgtgccatggagccggatttggaaccggag
aatcgtgaagggatgtccgagggtctcttgtcgttgtaatagatcacagtgacaggggcactgccaggtgacttctgctgatacca
gccatagctgccactactcccggagcaggtgatcttgacggttcctcccaggtttgctgacactgaggccggctgagtcactgct
gcctgcaccagggaacctggagaaggagagaagagaaaatgggctcaacaagagcctgacacacacagccctcccaagca
gcagtgggatggggaacagcaccattaaaggaaaagggacttcagccatagccacatcaaaggatgagagcccagcccaga
gcagcccagcacagaggcagctccatggagcagggctggggatgacaagatgctgtatctttacaaggataggtacagtgtgg
gtaagtgtcagagtaatctctcatacatctaggtacagacaggagggcatttacaaacacggccacgcagagaggacagaaac
ctgcctcagcccccacagcgctgataagccattactcagtaagtgcagaaagtttccattttttaactcaggcctgttactcagtttttcc
atctccctgtgtcactgatccccaacttggactccagtgaaggctaaccatgatcagccttctgtgagctgagaaaaggagtgtag
tgagcagggagagcactgcaataggagctgatagtgatcacacaggcctgtactatgggcagatgggagtttaagagtgaattg
cggtccatggcatatgcctgtcagcatagggatgctggaggaattgcaccttggcatgagcccctctcctcctggtgatgcttgcc
cacagctctgacgtcctgggaaggctcactgcaccttgttgtcagtgaaactgcaataagctatcaagatttgatataattctgccc
ctctgatctacttgtgagaccacacctggagtactgcatccagttctggtaccaccaacacaaaaaggacatggagctgctggag
cagggccagaggagggccatgaagatgaacagagggctgaagcacctcccctatggggacaggctgagagacatgggcgct
tttgagactggagaagagaaggctccatgggacctttcagtgtccttccaatacttgaaagggtccttgaggaaagctggggagg
gacttcctataaggacatatagcaacaggacaaaaggaaagggttttaaactggaagaaagtagatttagtctagatagtaacaa
gaaattctttacagtaaggatcacgagacactgaaacaggttgcccaaagcagctgtggatgcccctccctggaagtgttccag
gccaggctggatggggctttgagcaacctgttctagtgagaggtgaccctgcctacagcaggggagttgaacctagatggtctt
aaaggtcccttccaacccaaatcattctatggcaattctatagagaacacctatgctgagagtagctacaagtatggctggttcctg
gcagtgcccctgtctctgtgatctatagcagcaccaacagacccctcaaacatcccttcacgattctccggttccaaatctggctcca
cacacacattaaccatcactggggtccaagccgatgacgaggctgtctattactgtgggagcacagacagcagctatgttggtat
cacagtgacatggagcaattaaaaatgatgcataaccttttgcacatctgtaatgctataaggtgagagaaagtaagcaataatag
cagagcagcacaatcctaggctacagcaaatgagaacaagcccagatgcagccacagaaataaagaaaaaaaaactgcttac
ctttagaaagcctcatatagacagggatctccagcaagataccacacctccactgccaacccttaaatgagggctgggatggg
ctggatcctggctccacccctttcaatcactcaggtacattgcacacacctgagctcccctggctggccctgccttcccaccaggt
```

Figure 9b Seq ID 186 (con't)

gctcaatcactgctttgggctgtgactcagcatctccactacagcatcacagggagcggttgtcggtctctgctgttcctatgtggg
tgccccgggacacctgaaggcatgagtggcagtgagggctcccagctctatccatggtgaacagacattatgtttatgctttaca
gcagcatgaatctggcagtggtgttattgctgtgatgctgctgtctatgctcccacagtaatagatagcctcgtcctcggcttggac
cccagtgatggttaatgtgtttgtggagccggatccagaaccggagaatcgtgaagggatgtccgagggtctgttattgccattat
agatcacagtgacaggggcactgccaggcatagtcgctgtaaccccggagcaggtgatctcgacggttcctcccaggtttgct
gacaccgaggccggctgagtcagcgctgcctgcaccagggaacctggagagggagaggagagaggggagaaaatggatc
tgagcaattgcctgacacacacagccctccccagactgtgggatgaggccctgtgccgcagtcacatgtggaatatcaagaca
cacacatctatgacaatcacaatctgattatcaaccactatggctggtaccagcagaaggcacctagcagtgccctgtcactctg
atctactatgatgatgagagaccctcgaacatcccttcacgattctccggttccaaatccggctccacacacacattaaccatcact
ggggtccaagccgacgacgaggctgtctattactgtgggaatgaagacagcagcggtactggtgccccagtgacacagagca
atggagatatgatacacagacctgacatctcagggagcagctggtcattatcctggtgacacaagtcccaggcatggcccagca
ctgtgctgcaggtggctatgccgggtgccctgctctgccctcctgtagagcctcaggactgtgcccatcactcagggaggagat
ggtcccagcagccttgtccctgccctgcactgcacttagctcctggaccccatctcctgctgcccacccatattgcctccctgtgtt
gctgttgcagggttgcttctgcctcatactggtttctcccttctggaggtggccaaaagccgggccctgtgcaatcctggtgcataa
ataccttatgccccctaagtagggcaggtgtgggacacgctctggcacctggggtgtgtgcaagtgctcaggaagacctgcag
gcacaggtggcagtgggggggtctctggctgtgctcgagcagcagctgcctgggggtaagggtagtactctgtgcatgaacaatg
ctgcagggctcagctctgctcagaccacgaccctggcaccaacagagacctgcctggctctgtggtcatgtaaaccttacagg
agctcaagacaaggctgtttattactgctctggcaggaaagaagcactggccatggtcatagagagttccagcaacaggaaagt
gagagcccaagctgctgaggtaccagggctcctcaggtgcctgctgcagcagcttggacacagtcgaggaacagcaattgtac
ctgtgtggtggatcaggctgtgctgcctgtgaacctattctagcacatctgtcacctctgtgccactcacagggataccacccctga
gacccctacccccatcagcctctgtgtgggatatggtgttgggcccaagggctctgttgcacagggagatagaggcctggggag
gagggaaagcattgaggtggtgttgataccagggatgtgagcccaagcaagagatcagcagagcaaggaggaagaattgca
ggtgttggggctggggaaagccccagatggctggagctggtgggggccactggagatctcctcctcccatcctgctccatgctg
gggcagctgctgcaggctgaccagggcctgcccgggcacgttgtgaaggtcaccaaggatggagacttcagagctatctggg
acacgtgttttaacgtttgatcagccttgcagcaaaacagtgttttgctctattgaacagtgttcaacaaaaacgatcagtggcctgg
aacacatctcctacgaagaaaggttgcgagagctgggtctggagaagagaaggctctggggcaacctccctgtggcctgtcag
tgcttaaaggaggctcaagagaaagatggagagagactttatacacggagctgtagcaatatgacaaggagaaatggtttaaaa
tggaaagagggtagatttaggttagctatcaagaagaaattcttcactcagaggtgatgaagcactgtagcaggttgcccagaga
agtattggatgcttccttcctggcagggcccaaggccagactggatgggttctgggcagcctgttctggtgggagatgtccctgc
ctgtggcatggcttggaaatgggtagcctttgaggtccctctcagcccaaatcattctatgttcttgtggttccctgcatttcagcctttt
gcctgttgactctggtgccactgttggacaattctactcagctgcgtttcatccctgccccaaagcagtaatcccatggataagcaa
tgctctgaggccttcaccaccctcagggctcctgctgacccctagcggcctccctggcagcatgagccctttgttgtccgcactgct
gctgctgagggtcctgccagcccccagggccttttctgcccaggcactgccacctgctaaaacccagcctgcccatggcagg
gcatcgcatgtctgagggatggaacggggcaagggcagtgctgcaggcagtggttcaagaaacgtttagatgttgtactgagg
gatgtggtttagtgggaaatactggtgataggtggatggttggactggaggatcttagaggtcttttccaaccttggtgattatgtga
ttctatgaagggagccatagcctgctcccatcatgccccgccagtccggctctcccgagcactttggttccgcagcatccaggcc
cgctctggggccggtgtgggcctgggtgctgccacgtgtccccgctgcaaggcctggccaaccccgctgtgccacaatgcag
gggctgggctaggagtgggcagggaggtgtggggagaggcgtaggacgtggctgggagcgcagggagttatttgcatagg
ggggcgtgctgcggaaggacgcgggtataaaagggcatcgaggtccccggcacagcccatcggcgtggggacacacagc
tgctgggattccgccatggcctggctcctctcctcctggcggtgctcgcccacacctcaggtactcgttgcgcccggtcgggg
actgtgggcacgggctctgtcccattgctgcgcgggcagggctgtgcgtgcggggccgtcactgattgccgttttctcccctct
ctcctctccctctccaggttccctggtgcaggcagcgctgactcagccgtcctcggtgtcagcgaacccgggagaaaccgtcaa
gatcacctgctccggggataggagctactatggctggtaccagcagaaggcacctggcagtgcccctgtcactctgatctatga
caacaccaacagaccctcgaacatcccttcacgattctccggttccaaatccggctccacagccacattaaccatcactggggtc

Figure 9b Seq ID 186 (con't)

caagccgacgacgaggctgtctattactgtgggagtgcagacagcagcagtactgctgcacggtgacacaaagcaatgggga
aatgatacaaaaacctcctgccagtgcaaggagcagctgatggtttttactgtctctgtcttacaagtcccacctccattcctgccct
gtgctgcagggcccaggtcctcctgcattcccaggctgcaccccaggtccagctggctgcctccctgccatccaacatccacca
tttgtagtgtccctgcatgcaccaggctggcagctcctcatctgctcctgctcccactgagaccacctgcccagcccatgctgga
gggccaccaccactcaattgcactgcacatcagcacagcaccagttctcttacatgtgtccctctgaggaaaagagctggacttct
aagcacccttagtgtactcacctaaaatgaaactgaaacccataaaagtctcagaaatacccagaaactgttcatccatagtatat
ggcatcaactttagctatatactttcatagatagtttcaatgagtttctatcacttgcaccggtcacttgcacctaagccttcccagag
gaaaaccaaacctttgaaacagaaagtacttccaaccacaaaatctttgatgcatcattcatttctagtgactcaggagattcacca
actctgcctctttctataaccacttgcacaaaccacagcatttgcatatttgtgagtttattttaagccagtgccttggctctggcagct
ctggttgggcatcaacatcctcttcacattttcttttcctctcttgaggaggatgtgggcagcatgtgcagcgcagtggtgcaccaat
gggataaagctgggcccagtgacctcgaaggacaacatcagcgagagtaaggccatcaaaacagacaggcctgaattggag
gggctgcactaaaactggatgacaggcaagaacattatttggtgggttcttgtggcaggttgacatgacattggccaagaccttga
ccaacaatggcacagctactggatatcccttggaagaggtgaggaggacacacagacaccatctacactctgtgacccacagc
aggcagcagggctcagccacacatgagcgggcatgggccgctgcttgggctgttctgcacggccatgtatcactgcaggtatt
tccccggtgggacctcaggaatcaactgatcgtcctcaggaagtcgctctgtgttcacttacagtcctccccagcagtaagtgggt
gctcaggctcctcacagccttttttttttttttttggttggttttgttttctttgtccaactttggctgtggcagtacatccttggtctgcctaac
cacactgaaatgtactcatgcaccttcctgatttgcagaaagaaggttgtatggtctgaatgctctgtgctgttgcaagtctcttct
ggttcttcgaaatctgcagagtccctcccgactgtgtccttggtactgaacatccttgttcaccgtgtcagaaggcagctgggggg
ctggaggcagtagtgcgtggcaccaggatccctggggcatttcttgcctgcggcgcctgggtgctccacgtggctgccaggg
ggacacacctcctgtagcagccccagcaccaccatcctgctgtgtccattccgtcaccttgatcctactgtgtccagcccatcgt
ctcccttctgctttgcctgtcagaagaacacttccatcccatcacttctgacccacccctcatcctgccgcctccacaggacccag
aactgcccctgccacgaagtgggaggttttgcattgctccgtatcactgtgtggtatatttggggccgggacaaccctgaccgtc
ctaggtgagtcgctgacctcgtctcggtctttcttccccatcgtgaaattgtgacattttgtcgattttggtgatttgggggttttctt
ggacttggcggcaggctggggtctgccaccggcgcagggccgggcactcagcgcggcagcctgggctgagtcttgtcccca
ccgagccggagggctccggtgtgcgccatggaggacttagggttattttgtcaatggaaagttcttaaaatttgaccagaaaatgt
gcccgaggtctgtctctgccacacgatttcagaaattgtgtctaggtcgatgagaagacagttttttgtctttgtcaggaaattagttgt
gagttgttagtccttccctcttagtcctaaggactaagacctttgtcccccggtctggtctctcactgggggactcttggctccagtgcc
atggggagcccaagtgtcactgacacggtgtccttggggggtgaaattcagtttttcagctgtccaggtaagtgctgtcaaaaaatg
gaggttattctgctgaaaaagctgagaggaatattttgtcattttttttcggaaatatatatatatatatatatataaatatataaattatttat
atattttatatatatatatataaaatatatgtatttctctctttcttttatatatatatataaatatatatatatttctccctctttctttatatata
tttataggagagaatctatattttggccaatttggccaatttctctctctctctcttatatatatatatatatatatgtaatttatatatat
atatataaatttatatttatttatttatttatttatatagattatttttatatacatatatatatataaatttggccaatttagaagaaattggcca
aaaaaacccaatctgaaccaaattacttagggcataagtccaaaaaaaaagtgcagttcaagaattcctcgctggaaagtttttaat
gggggcagttcttccccatttttctggtgtagatatgagtgaagatatagatatgtatgtagatatagatttggctatagtttgtttgatga
acagtctgaggaagagtaaatcttgccttcctcatggcaattttttaattctacttcttctgagacaagtctgaacatgccttgaggtag
aaagagcccgaaaattgagtgcttttctttgaaattttaattaaaattaaaaaaatagccttacagcaggaaagaaaggggtgatg
gcagctaatcggagttccaaagctgaaccacgttcacccaaacacgtggttgaaattttgtgtgtgtatatatatataaatatatatgt
atacaaaagaaaatgcctatatataaaaaaattgttatgtatattatatagatttattatagatatgtacataagatataacacgtataca
tatatatgtagtctgctgtatgctttgtataaatttttatagatatgatgtatattatatgcatgggttatatatctataatatattttatctgta
gaaggaactacagtataaaatgcatatatgcgtatatatacacatatttatatatatgtgtatatatatgtatacgcacacgtataacat
ccatgaaaatagatatggatgggtgatgtgtttgttttacagaggtgcatgtgtgtctgtacatacacagccatacatacgcgtgtg
gccgctctgcctctctcttgcaggccagcccaaggtggcccccaccatcaccctcttcccaccgtcaaaggaggagctgaacg
aagccaccaaggccaccctggtgtgcctgataaacgacttctaccccagcccagtgactgtggattgggtgatcgatggctcca
cccgctctggcgagaccacagcaccacagcggcagagcaacagccagtatatggccagcagctacctgtcactgtctgccag

Figure 9b Seq ID 186 (con't)

cgactggtcaagccacgagacctacacctgcagggtcacacacaacggcacctctatcacgaagaccctgaagaggtccgag
tgctaatagtcccactggggatgcaatgtgaggacagtggttcctcaccctccctgtccctctgggccgctgctggtggcagcag
ccctcacttcccactcagatgtcccccaccgtgcccccatcacccacctgcctgtcgactcctcttgccctcatctctccaggtg
tcacattaataaacacgacactgaactagtgctgactctgcatccatgtctctgtgtccttttgcgtgctgtctgcatctcacacaggg
gggtcggccccagtatggggaagggctggggggcgcatacacacatattggtaatgttggggacggggggggggggggtgg
ggggtcaacagatcagcactggagacactggtgtataccctggcaccaccaacatctaaggcagggtgctttggggcaatttt
ggggcagtttaaggtctgtgctggcactgagcacgtggctgtggccgtgctgtcctcatctcccacccactacggtctgtgcgcc
aggtccctagcagagatttgctttatgctgggaacaggggggagttctggctctgttcccttgcattcagacaccctggtgcccct
gggtgggatgtcagtgtgaatactcctttgtgccctgtgcctgcagcagcctgaccctccacacaccacgccttgtgtgcacc
ccacccctgtcactatccctctccccgctccccagggagattttgcagtggccctgtagggcagcttttagcacagcccccagc
agcaagcaagcagaaagcactgctgtgcacagcttgtcagctgtgtgtgtttgctgaggaggatctgtcttttgctgaggccatca
gtcttgtcctgctcaacctccatcgatgctgccacctcaacacatctaccatctattccatctacaccaacatctccattcatccca
cccacccaaacatgtccatccatcacaacacctccatccaacccgcacactccagcacctccaatcattccatctacaccaccat
gctgatctgctacagccactccaacgcaaccgtccattccatctacaccaatgtccatccatcccagccactccagcacctccag
ccatcccacccacccctatgtctccatccagccactggtgggggtgcaggacatggggccagctctactgtcaggactgggggttttt
gcatggccccataccacttctgcagaagagacgcactgaaagtttggctgaccattttctccacggtagagttgtggcagttctgt
aatttagggtcttttatccagtttggagatgggctgggatctcccagctccatggcaggcattcatgacactggtttagtatctgat
gggtgggatgtggctgaacttcattttctttccccagtgacaaagttttgcagttgaatatgaattcctgctttctgctctatgagttgtt
tttttcccaggacgtacacagggaatcagcagtcttcattctccctctgccatgtgtagactctctgccacacaggactgtgctgtcc
tcatgcccctgcgcccaaattgctgccctctgcccatgcctgccaagctgagccctgcaggctgccatgctggattgacatgagc
cctgagattggtacagaaatggtgattttggggttttctttgcactcaggaagctgaaggctcaatgctcagtgatggatttaccaaa
ctgtgccctgaggcagctgctcatgctggataaagtcactggagcacagggaaccaggcgctgggcagggatttctcatgggc
cccacttggaaagctgcaggctgcaaacctggctctgccttcacgcctcaccctcatgaggacaacctcactaattattgattaaa
agattttgctaaaccatctccagaagcaacaacccactgaggagcatgtgctgaattatacatcacagctccacggccctgccct
catagcagggctgcatggcacccacagtggcactcagagggaccacagggctgagacagccgggtctggtggtggggaca
cagctgagcataggatgagccccccgggcagtgctgggctttgctaatgagcagaagtatggatagaaagcaacccagggc
tccgtacccagctgcagctcttgctctgtcgtgtcctttggtgaaactttaaacagtcgccttttttttttctcttttctttttctggcttgccatt
aatttcaaaccgagagagacctaatttagtaaatgagatgcttcaggaaggctttaattagctgcagatggaggcaggcagtgcta
tcgtggggcctggatcgcacagggggctgcatatcctcactagcagaatacactcaggctgggtccctcccacattcatgcccc
agaccagagggaatatgctctgttccccacacatcgctcccaatcttgcagccgttgagccccaacatcccaccagcacacggg
gctcagcacgcctggcgacatggcatcagcagagcaggccgcatggtacagctccatcagcacagctggggccacacaaag
agctgggttactgtgggcagcaggctgaaacccgaaaacaagagctgggggctcagaatagccccgggagcaggcagggc
ctgggggtgagggcaagcaccaggcccagggccacacagcccttccaggaaggcacagcgctgtcagggtgcagcacgct
cagccccaccatgcagctgtgcggccggggcatccccaagctaaatttacttctcagtctccaatcagaaactgaagctgaggg
gcccacaccggccaaaaaaaggaaacgaaacagtctccagaaagcactgacgtgtgaagcagagcgagcgccgcgcaaac
cggccgccatgtcacacacctcaggttggggctttgccagactgagctttgctgctgctcggggtgggtgcccacggcctgggc
acatgggatggggtacacacgtacacacacttgcacacccacaccccaacacttcaggtgatgctggtgcagatgggtgcccc
ccaggctgaccccccacgcatgggcctggccccacactgctccatccgtgtctctgtccccatgtgccacccctgcccgctcc
caccacgcgtcaccccaaatcctgagttaatcccacgactcctgcctgcttccagcgtccatggcagactggagatgcccaaat
gcagagcaggtttccctgaatctgagagatgaaatggagttatgggtgttcccctgcggcggagccccagctgtaggaagctca
gagccatcacacagcaattaaagaggaattaaattaaatcaataaatgttttaggcgggctcagctgccagcaccacctgaccga
aacagcccgcttgcaaagaggagagcatttgcatggctgtggcaaaacagcaaccgcctgttgtgcagctgggatggtgttatc
tggaaatgtacgcagcccaggaggggtaaacagctccaaactgagaccccgaacttgtccacaggttgtaaacaggctgacat
aaacacctttgtgccgtggaaaaatatttatcacctcaaatatagcaggttaataaaataaaactcccaacggagctacacacctgc

Figure 9b Seq ID 186 (con't)

tttggaagggaagcagacacttgttttctgcttgatgttggctgtaggaagccatgtttcccgatgcaggagggccacaaagcact
gacaacacaatgtgagctgagcttcgcccctgtttaagcccccacctcagggcttgtggtctcggagcaggcaggacgcaggg
gtggcaccgggctgggtgacatgggctggtcctggggtgtctcactgagctctttggggaggggttggagccctggggcaatc
acagcacacacagaggaggtgggggatgcagccagcagctgccctgcactaagaaaacccatccgtgggctttcagatg
gccttcccatctctctgcagcctctgcatgggctgaacacaaggtttaagtgtttctgccatgttttggggcatgtttggaggggca
gcgtgggcccggcatacgggtactgccacgtgccgccagccccacagctgagcctgcactctcccagatgtgctgaccgca
gccacgggggcaacagtttctcttgctaaaaattgtagccgggaagaaaacacgtggcaacttcggccaaacagcagctggag
gacaggaatagccgtggccacggcacgctctgcttcctcggcacaaacattccagtacgtggcaccacgagcgccgctgccc
ggcacagcagcaagcagagccaggagcaggaaatgctgatttggggccccattttggccatggctgagagaagaggcttccag
ggagctggtcagcttggtccccaagctgtggcttggggaaatgatggggaggggattgccactgcccaccctgcagagcagg
ctctggtcccatctcactgcagggcaccagggcgtttgcactgcagcaattcacagaaacattgaaatggctcctgccttgttcaa
catcttcatcagtgacctggatgaggggacagcatccaccatcagcgggttcactgatcatatgaagtcgggaggagtggctga
cgcaccacaaggctgtgctgccattcaacaggacgtggacagactggagagctggacagggaggaacccaatgaggttcaa
caatggcaagtgtaggatctacacctgggaaggaataacagcatgcatcagttcaggttaggggctgagctgctgcagatgagc
tctgagagaaggacctgagcatcctgctggacagcaggctggctgtgagccaccggtgtgccctggtggccaagaaggccag
tggtatcctggggagcaccgcaatgagagtgggcagcagggcgagggaggtgaggctgcatttggagcaccgtgcccagttc
tgggctcctcagttcaaggcagacagggaactgctggagagagcccagcagaggggctgcaatgatgatgaaggtcctggag
catcgcctgtatgaggaaaggctgagggacctgggattgttcagcttggagaagagaagactacagggcaggagccaagtgg
atagggccgggctcttccagcagtgcccagtgacaggacaaggggcagcaggcacaaagtggaacataagaagttccatct
gaacatgaggaaaaactgcctcgctttgagggtgtctgagcactggaagaagctgcccagagaggtggtggagtctcctctgg
agatattcagagcctggcaggacacttttgctgagtaacctactgtagggaacctgacgcagcagaggggtcggactggagg
atctccggaggtctctttcaaccccctacagttccatgaaatacctcaaacactgccaagcgcagtgctaaggcaagggtaacattt
gtaaactgaaacagggtgggtttaagttagatgtaaagaagaaactcttcactcagagggtggcgaggccctggcacaggctgc
ccatggaggctgcggtgccccatccctggcagtgcccaaggcaagagcccagcagtgaccacagccccacaaggacgag
cgtggccctcgtatctcagctcaccctgccccagctcaactcccacctccggcacagcgcgggcacacagccgggccctgtg
cttatggagccccttggggcaggtcagcactcacaccctccaaacacagccgtggctcccaaccggaggcagctggatctcggc
agccataaccaagcagggccatgcgggggtgacaccggggtccccaccccctgtggggcagcgtatgggctgggcccctg
ctccagtctgcagcgtgtgcatgggaaccatcaccagacaccatctagaccacctgcagccctaagctgcctcacagcaggga
ttgctccgtcacaccgtgaccccgtgcccttattccatcacttacggggctgggagtgcctggaccttgggcacattaacgaggat
ttcccgctctgccctcgctttgctccgagccgtggggctgtgtagtgcagacacagctgcagcctaaaattagcacctgggaaag
gcccccatgctgcaccgcgcagggctgagatgtgccacgtccccatggccggagctggggaaggcaacgtggccctgtgcg
tgtgcacgctgagcacaaggacacgtgctgggccaggatttgtctcccggggctcacgctatgtgtcacccgtgctgtgcca
tcccctcccgcagcccccagctccccacggccgcacgccgcctgcatccctgcaacggcaccgcacagagacacggagcc
agggggccgcacacggggccaggagctcacctttattgcagccctgacagccccacggcccagcccatagcggggctgccac
atcctcacccggccgacggcccagctgctccttaccatttcttcccccatcacccataaaccagaagccgcctcaccgctacgc
ggagcgggcagcagggaacccgggccctaagggggagacgagagggggccgagcaggggcaggaggagcagcaggg
cgagggggcagcggggcacccacagctggccgtggcatcccgggaggagaagaccttgcggctgcggagcggttgtgg
cggacggaaattgttggtcatcttcaggggcgcagcgcccgaggccgggaagtgcacggtgctgacaaacgcctgcagctgc
ggggagagcaccgcgggcgccgcagccgtgaggcgtagggcgaagcggggcacacgcgtggctgctgccgggcagagc
gcagcgcaggagcccgtctttcccctaccggcagcacacggctctgcacacaccgcgcttcgtgccgcctcgcagccgac
gctgcaggaagcccagccgagcgcttacagagcggccgggaaatgcatctgctgaggtgcccgggcaatgcagaacttcatc
catcccacatccattccagtcccctcccaaaccccatgccatccggcgacccacccaccctcctcttggtgccctctca
agctctccatccccacattcctacagatgtccctttactttgcctgcaaggtgcaagaaaacgcacagggaccggggtgctca
cagcacggctttggccagacgggcccttccatcccatggcagcagggccgaggaatcccattacctgctccctgctgatgccc Figure 9b Seq ID 186 (con't)

acaggctcctcaaacacggtccagatgacggcctcgctgcagtcaggggttgtcagggagccctggtagcggtagtaccggg
acagctgtgcaacgtgcggcagcagcgtgccaaggcggaaggtggaggccaggtccactgcctgccctgcacagcaggac
atgggcactcagccccgctgcccctggcacgccccagggtctctcccctcccagccgtgccccattgcagagcaccagggca
cctcaccagcatgggagatgttcctcagtcccccaatgatggtgttgtagttggagtttggggcttctgagacctgcaaagagcga
gtgggccctgcagctgtgctcatttaaggccaacgcatggcagcacccatcccatgcactttgcagccaacctggaagaagca
gcccagcacagccagcccgcttgggtgccccttggcctcccccagggtgcggtacttgacgttgatgtggacgatgtgcagct
ggagaaagaaagcacggagggctcagcagaggcaccggcctcgccagcagccaggcaccaggatgggaaatcaaagg
gccgtggtgctaaggggcttcttgcctacctccatggggagctgctgcccatccacggtgtgctcagagccattcgtagacagg
ctgccccagtggaagtgcagctgcagtgcacggtagcggcccgggaggcccccgccactgatggcaatgtgctcagcaccc
ggctcgctctccaggctcagcatcactgcaaacgataggagtgggacaggactgggggccgtggggcagcactgctgcaga
gctgagccctggctggagcagaacacccacccgtgtgcccatcgttcagcagccgccacttgccgggggggtgcctggtcata
gccctcaaagatgatgtccccaaggctgccgtcccgctgcagccagcgccggtcgatgttaaccggagactgcttgtcaccgc
cgcaggtggccttcagctccttccagtggctggggcctgcggggagcacggccatgggggcacccgcagagccaccagcac
caccccccagggggggacacagagccaagggcagccctgtccccaccacggaccctgccccatctccagcccttctctccccgt
tactccaggaaggtttttacttggaaacctgtggagctgtaacccgccccgtgagctccccattacccaccgccttcattaagggat
ggtgccctcagcacgtgcctgttctgtgctgccccaaccgcccccgccagccccagcacggtttaattgctgctggagccggc
tctgtgccgggcagtgaggctctgagcgctgctggacgcagctgacctgcagcacagtgagcacgcacctgagggctataaa
gcaattgggctgtaactgctgattacatgctccctgatccttaattaacctcttacaagctattatacgtgcgtttccaaagtgccccc
gggcactggggagggaggcaccgaacagagctgtgaccgtccccactcaccgcacttcgggtcctgcgagtcgtagcacca
ctgccctgcgggagagagctgtagtcaggggctgcagaggcccccaaagcccccccatactgcggatctctgcacagcacac
agcgtgaccgtgggcagaggtgcgcccacaccgcccggagcagcgctacgcggagccgcttccctcccacctcgctgctgt
cagtgcagggacacacagctctgctgtgttgggagcggggtgaggagcgcggctgctgcccacggccgctctgctccgctca
tgtcccaccaacccatccaaatcccgtgtgggaactcagccaccccagcactccctgcctacagggatggttccccgctgacc
ccgtgctctctccagccacaggccgcaggcagcgctgcgtgcaccgctgtgctgctggcttcgcatccatgtcctcaccacgc
tgctatgtgaggctgcagccacagggctgggaacagggactgtcccagggcagtgacttcaggctttccttcccatccagcgg
gaactgagcctcctgcacaccctcagagccacaaagcgctgccctcacccaactgtgagcatccctggcgtgagccaggtgg
gcgctctgctctatagaagggtgctgcgcactccagcccattttgctctgaggtgtcgtcctcagtggcatttccctgcttatgagt
acatggggcagaggggctgaaacctcaatcccagctgcctgattgaccgtccgacatcccagacacctcccagcagggctga
cacctccctgagcccggcagcacggcggggacagggtgtcccacggggagggcacagaacacagctcctgggctgcacc
acatctccgagcgccacagacatgcattcccccaacatgtgggaaagggaatagagtgctggcactgccgtacccccctccc
ggcaccatgctaccccataaccccaagccacctgcactccgtgcccatccctccgcagccccaaccacgacggtgcagcag
acgggcagcgcat

Figure 12a Unit1 Seq ID 187 gcgatcgcataacttcgtataatgtatgctatacgaagttatagaggatcctattaattgtttgttaattaagaggacaggaattcagt
gtcaggggctgctctttgcttcccaatgtgtaccactgaagcctctctggatttatcagagatactcaatggactcttaacagcact
gtggcacctgacctcctgctgccttcagcctcccttcctggctggtgtgcttgtgttgaggagctgtgggaggctggtgcagttctg
tgggatgaggtaaggccagctgaatagcctggggggctggtcaggggggcttagtgagaggagcagggctggggaatattgtga
acagcaggtggtgccactgctattctgaggaaggaggcagcttctgcaaatgctttgcaatgcaggatgacaaagtgcttctgct
agctctaggcccttgctcatggctgtgatggtgcttaacggtgccagagtgcagtgccagatatgacatgcagatgacccagtct
ccatcctcgctgtcttcctgtctaggtgagagtcaccatcacatgccaggaaagtcaggcagggcattagccatgttttagcctgat
acaaagagaagccagggaaagcttctgagctcctgatctacgatgcatccaatttgcaaacctgggtcccattgcagttatgtgg
cattggatccaggacagatttgattctcaccattagcatcctccagtctgaagttgctgcaacttcttattattggtcaacagtataaaa
gtgaccctctgtacactttggccaggggaccaagctggagatcaaactaccagcagaagacctctggcagtgcatctgtcgct
gtgctgaaaccaacagacacaccaacaccacaggacagcttcttgcagttctccatctcctggtgcagcttcatgagcacgttaa
ccatcgtggggattcaagctgaggatgtagctgtctatccctgtggcaacagggacagcagtggtaagcctggtgaggtgatac
agggagatgtcaaaaaaaaagaaaaacccaacatgtatgggggttaaaaatggaggctctctgcccttttctctcatggctgagct
gggctgtgcagtgaggtaagttcctgtctcgtctgcaaagcactgtctgaatggtctccctattgtgtgttgtggtgcatgagggatt
ctggggacagagggcatttgtctgtccctataaaggcccaaagccctggctgtgtacagtaagtccgcctggggcacctgagc
tgtgggcaggtactgccaggagaggggctcaggccatgatccaataccaatggctctgtgtccccatgctaatagggctatgct
gcagcccatcactccctcttaaaccccctcttaaacttcctacagttctaagttctatctctctcctccaattaatcatcgtcaccatagt
ttgatatccactttggtcccagggccgaaagtgaacggaggggcattgtaagtccgttgaccgtaataagttgcaacatcttcagg
ctgcaggctgctgatagtgagagtgaaatctgtcccagatccactgccactgaaccgagatgggactccagattgcaaattggat
gcactatagatcaggagcttaggaactttccctggtttctgccgataccaatttaaataactgctaatgccctgactcacccggcaa
gtgatggtgactctgtctcctacagatgcagacagggaggatggagactgggtcaactggatgtcacatctggcacgaggaga
gaggggagaaaatggagctcagtgagtgtgcgacacacacagccctcagcgtactgcggtgggataatacttctgagcacaca
gtcccaaatggaacctcaggactctctcatctgcttcaggatgaacaatgtgtgccagatgtgacatccagatgacccagtctcca
tccttcctgtctgcatctgtaggagacagagtcaccatcacttgccgggcaagtcagagcattagcagctatttaaattggtatcag
cagaaaccagggaaagcccctaagctcctgatctatgctgcatccagtttgcaaagtggggtcccatcaaggttcagtggcagt
ggatctgggacagatttcactctcaccatcagcagtctgcaacctgaagattttgcaacttattactgtcagtgtggttacagtacac
ctccgactttcggccctgggaccaaagtggatatcaaacaggcagcagtaatcctggtttggtgatacagggagatgtgcctccc
cccaaaaaaaccccaaacaaacaaaaagcatatataggggggtaaaaatggagttttctgcccatctgtctcacagccaagctgg
gctgtgcagctgcggcaggttcctggcctctctgcaaagctctgtttgtgaatggccttccttcctcttgtaccttgtggtgcaggag
gagattgtggggacagaagccacttctccttgtccctacaaaggcacagcactgtgtcatcccagccctcctccatgttactgct
ggcagtcccgtcctcctgcttctgaagagacatggatgtaggtgaggtctcttctgcaacagtggtgttcatcacccccacagctgc
caggtgagggctgtgtgtgtcggacatttggctgagctccattctctcctgtccctctccaggtgccagatgtgccatccagttga
cccagtctccatcctccctgtctgcatctgtaggagacagagtcaccatcacttgccgggcaagtcagggcattagcagtgcttta
gcctgatatcagcagaaaccagggaaagctcctaagctcctgatctatgatgcctccagtttggaaagtggggtcccatcaaggt
tcagcggcagtggatctgggacagatttcactctcaccatcagcagcctgcagcctgaagattttgcaacttattactgtcaacagt
ttaataattaccctcacacgttcggccaagggaccaaggtggaaatcaaacagtgctgcctgcaccagggaactgggagagga
gaggggggagaaaatggagttcattgagtccctgatatacggagtccttgctaggcaatgagataagacagctgagcccacag
accatcttttacggaccagaagtgacatccagtcacccagtctccatccacactgtctgcatctgtaaggagacagtgtcaccatc
acttgccgggcgagtcagagcattggtagtaatttagactggtatcagcagaaaccagggaaggcccctaagggcctgatctat
gctgcatccagtttgcaatctggggctccttcgcggttcggtggcagtggatctgggacagattttactctcaccatcagaatcctg
cagcctaaagatgttgcaacttattactgtcaacagtataaaaattaccctatgacgttcggccaagggaccaaggtggaaatcaa
acactgtgatctatgctgacaccaacagacccaccaacaccacgggggcagcttctcacaatcctacacgttctggtgcagcttca
tgagcacattagccattgtggggactcaagctgaggatgtggctgtctatttctgtggcagcagggacagcagaggtaagcctg
gtgaggtgatacagggagatgtcaaaaaaaaatgaaacaacatgtataggagttaaaaatggaggttttctgctctcttctctcaca Figure 12a Unit1 Seq ID 187 (con't)

ggtgagctgggctgtgcagtgagatgagttcctgtccctctgcaaagcactgtctgaatggtctccctgctgtgtgttgtggtgca
tgaggagagtctgaagacagagggtacttctccctgtccctgagaagctgctgcatggtgtcatcccagccctgctgcatgtta
cactgtctgccctgtccttctgatgccgaagctgcttccatgctgggatgctctgggctgagctctgattctccaaaatggcagtgg
tttcttctgatggtggtggtattcctcattctactgctgtgcagggagggctgtgtgtgttggctacccactgagccctgttttctct
cctctccctctccagggaccagaagtgacatccagtcacccagtctccatccacactgtctgcatctgtaaggagacagcgtcac
catcacttgccgggcgagtcagagcattggtagtaatttagactggtatcagcagaaaccagggaaggcccctaagggcctgat
ctatgctgcatccagtttgcaatctggggctccttcgcggttcggtggcagtggatctgggacagattttactctcaccatcagaat
cctgcagcctaaagatgttgcaagttattactgtcaacagtataaaaattaccctatcactttcggccctgggaccaaagtggatatc
aaaccagtgaggggcattgaggctgggaacaatgcagtgctgtgcctttgcaggaacagggataacgggggcactggacccag
aattgattactgaatgaaaaggttcagtaagagaggacatgcgtgtgatgtacagtctggcagaagggactggattctccctcag
ccctgactcaacaagggcagaaagccttggttttgaatcgcagtctgcatgtcaccccacatctccccacatcactatacgtttga
tctccagcttggtccctggctaaaatggggaggggtactataatactgttgacagtaataagttgcaaaatcttcaggctgcagg
ctgctgatggtgagagtgtaatccgtcccagatccactgccgctgaaccttgatgggaccccactttgcaaactggatgcataata
gatgaagagcttagggggcttttgctggttttgctgataccaggctaaataactgctaatgccctgactggcccagcaagtgatggt
gactctgtctcctacagatgcagacagggagaatggagactgggtcatccggatggcacatctggcacactttgggacctgagc
cagactgtacctgtccctacaaaggtacagcactatgtcatccccagccttgcttcatgttgctgctgcaagccctgttctcctgctg
gagctgtctctgtgctgggatgctctggtctggactctcatcttctaatgtgccggtggccatgactgaggttcttctcctttaatagt
ggtgctccctttcccactgttgtacgcagagggctgtccatgtggggtattccctgagccccactttctctcctctccctctccaggt
gtcagatttgacatccagatgatccagtctccatctttcctgtctgcatctgtaggagacagagtcagtatcatttgctgggcaagtg
agggcattagcagtaatttagcctggtatctgcagaaaccagggaaatcccctaagctcttcctctatgatgcaaaagatttgcacc
ctggggtctcatcgaggttcagtggcaggggatctgggacggatttcactctcaccatcatcagcctgaagcctgaagattttgca
gcttattactgtaaacaggacttcagttaccctcccattttagccaggggaccaagctggagatcaaactagtgccaggggggag
atgaggcggtgaattgatggccagagctgaaaatgatgggtttccacccttctccattatgacttttgttgagatctcttctcatgatg
gtcttccctggttttcctgtggttggaaggagcagaaggcactggcaggggtcttgctgggagagctggcaatagcagggatag
tggatgccccacatggaagaaagggacacagctatggccacttctgatgagaggtgtccagagcacagcagcacatccctgtg
cttcagacatctcctgtgccctggggtgtggaagggaatgcattcatagcatggccaggtggaggtaagagtaacatgcctactg
cagtaattctgcacatagagaaggaagaaagacagaaaatcttcctacagttctaagtttcctctctcttctccaattaatcatcatca
ccatagtttgatatccactttggtcccagggccgaaagtctgagggtaattattaaactgttgacagtaataagttgcaaaatcttca
ggctgcaggctgctgatggtgagagtgaaatctgtcccagatccactgccgctgaaccttgatgggaccccactttccaaactgg
aggcatcatagatcaggagcttaggagctttccctggtttctgctgataccaggctaaagcactgctaatgccctgacttgcccgg
caagtgatggtgactctgtctcctacagatgcagacagggaggatggagactgggtcaactggatggcacatctggcacctgg
agagggagaggagagaggggagaaaatggagctcagtgaatgtgtgacacacagccttcagcatgctgcagtgggactgag
caccagcacttgctcagctccattttctccaggtgccagatgtgacatccagatgacccagtctccatcctcactgtctgcatctgta
ggagacagagtcaccatcacttgtcgggcgagtcagggtattagcagctggttagcctggtatcagcagaaaccagagaaagc
ccctaagtccctgatctatgctgcatccagtttgcaaagtgg$_t$gtcccatcaaggttcagcggcagtggatctgggacagatttca
ctctcaccatcagcagcctgcagcctgaagattttgcaacttattactgccaacagtataatagttaccctcccacttttggccaggg
gaccaagttggagatcaaaccacagtgacacagagcaatggagatgtgatacacaaacctgtcagtgcagggaacagttggca
ctggcactcatctactcctggactcacaagtgccagatgtaacatccagatgacccagtctccatctgccatgtctgcatctgtagg
agacagagtcaccatcacttgtcgggcgaggcagggcattagcaattatttagcctggtttcagcagaaaccagggaaagtccc
taagcacctgatctatgctgcatccagtttgcaaagtggggtcccatcaaggttcagcggcagtggatctgggacagaattcactc
tcacaatcagcagcctgcagcctgaagattttgcaacttattactgtctacagcataatagttaccctcccactttcggcggaggga
ccaaggtggagatcaaaccactgatgctggtagtgacggggagatgtgaaactgaggtacagccctgaattaaaaacgtctgttt
tctgcctttctcccttatgtttgttctgggctgtgtcactgaggcagttttccctctgcatggccatggctttgatcatcttttctgtcctgc
ctcagtgtttggaaggtgactctcccagttaccgcggaggaaccatgaagatcatttgctcctggtgtagcagtagctatggttgtg

Figure 12a Unit1 Seq ID 187 (con't)

gctgcatctggcttcaacagcaagttaaccattactcatgttgaaaccaaggatgaggctgtctaagatgtgtgagctagcatagc
agtgaggctggtagagtgacaaagggaagcatagctgtgatgtctacttctggagtgcactggggcatgaaagcgaaaacagt
caaagccacaaccacacggagggaacaggaacatgtctacagccataactctgcgtggccaaaatgctgaaagtcagaaaac
cagcagggagcggggctgggtgcagtgcatgccaacccttgtggggacagctgtagaacatggaattcaatctcagtggagt
cgaaccaattggcaggctgtcagcagaggcattccccagtgctcccctttgtttaatgtgaaattacaaacaacgctgccaggca
acaaactgtattgatctgcttgagggtaggaaggccttgtagacagatgaggataggcaaaaatcaatgggctgtgtcaaaccca
ttgacgttcaagaacgttaagtcccagggcctgcacttaggtcataacaacacaaggcagcagtgtaggctgaagagatggttg
attagagggttctgttagaatggttcaattctgtgatcatgaagataacttccaaacaaaattggtgtaggataggggataaggtgctc
tggccccagaatcacctgcaacaaaaaatacagcagggagggcataaacaattgcggccctgcagaggggcagggcatctg
cctcagtttgatctccaccttggtccctggccgaacgccggagggtaactataatactgttgacagtaataagttgcaaaatcttc
agactgcaggcagctgatggtgagagtgaaatctgtcccagatccactgccgctgaaccttgatgggacccactttgcaaagt
ggatgcagcatagatcaggagcttaggggcttccctggttttgctgataccaggctaaataactgctaatacccctgactcgccc
gacaagtgatggtgactctgtctcctgtagatgcagagaatgaggatggagactgggtcatccggatggcacatctggcacctg
gaggggagaggagagaaaatggagctcagtaagtgcctgacacgcaacacccagtgccagaagatagcactgatccccaa
gacaaggagaccatgcatgccaaagaggttcctctttctctcccacttcctctcagtccggctctagggtctcccctcctcctcctg
ctctccttcaccctgtacatcagatcccagggctttgctgcatttctgctcctgcaggcattgcctgggggccctgtggcaagaccag
ttccagatgcgacatccagatgacccagtctccatcttctgtgtctgcatctgtaggagacagagtcaccatcacttgtcgggcga
gtcagggtattagcagctggttagcctggtatcagcagaaaccagggaaagcccctaagctcctgatctatgctgcatccagtttg
caaagtggggtcccatcaaggttcagcggcagtggatctgggacagatttcactctcactatcagcagcctgcagcctgaagatt
ttgcaacttactattgtcaacaggctaacagtttccctcccactttcggccctgggaccagggtggacatcaagcccgcagtgcca
ccaccagcatatcgtttgatatctactttggtcccagggccgaaagtgagagggtcacttttatactgttgaccaataataagaagtt
gcagcaacttcagactggaggatgctaatggtgagaatcaaatctgtcctggatccaatgccacataactgcaatgggacccag
gtttgcaaattggatgcatcgtagatcaggagctcagaagctttccctggcttctctttgtatcaggctaaaacatggctaatgccct
acctgactttcctggcatgtgatggtgactctcacctagacaggaagacagcgaggatggagactgggtcatctgcatgtcatat
ctggcacctggagagggagaggagagaggggagaaaacggcaatcagtggctgcctgacatacacagcttcccccccgcaaa
gcagcaggacagaggccccatgcccatacaggcccaggtcacctgaactgttggtgaccatcactagtaggagaggggccca
gaccatggtgctactccaacagttgtgctatggaccccaactcccttttagacccccaccttctacagcacagccacctcctgca
agcctggtgtccatggatactggccaccccatcccatgctcccctttgcctcctgtagccattttccttgatctcagaagaccaatc
atggttagccattactgggatccaaaatgagcacaagactatctactactgcggtagcttgggaaacagcactgatactggtaga
atggcacagggagatgggaaactgagttacaaacctgagttcaaaatggaagctttctgcacttactgcattatggctggacagg
gctgcagggctgagtcctgtttctgtcctctctgcacggccctgactgtaaatggcctcctctctcttcttaaccacaatgtacctgt
ccctgcccaggcacagcactacgtcaaccctagccctgctccatgttgctgctgtgagctcctatctccttctagagctgcctttgt
gctgagatgctctgtgctgggctcttgcccacaaacataccctatgtctgtgactgaggaccccttctcctctgatggtagtgcttcccc
tgcggttggggagggcagggcaaattgggcacctgttgagccccatttactcccctctccctatgcaggtgccagatgtgccatc
cagatgacccagtctccatcctccctgtctgcatctgtaggagacagagtcaccatcacttgccgggcaagtcagggcattagaa
atgatttaggctggtatcagcagaaaccagggaaagcccctaagctcctgatctatgctgcatccagtttacaaagtggggtccc
atcaaggttcagcggcagtggatctggcacagatttcactctcaccatcagcagcctgcagcctgaagattttgcaacttattactg
tctacaagattacaattaccctccaacgtccggccaagggaccaaggtggaaatcaaacgtatggtgataggggggcgatgtgg
ggggaaaaaaaaaaaaaaaaaagacacatataggggataaaaatggaggttttctgcccatctgtctcacagccaagctgggct
gtgcagctgaggcaggttcctggcccctctgcaaagcactcgttgtgaatggtctccctcttgtacagtgcagtgcaggaagaga
taccaggtatgtccagacctgtttgctgttactgctggcagaccatcctcctgctttgaagaggcatggatgtctgtgaggcctcat
ctgccagggtggtgttcctcatcccaccccctgccaggtgagggctgtgcgtgtcaggcaaacactgagccccattttctcccctct
ccctctccagataccagatgtgacatccagatgacccagtctccatcctccctgtctgcatctgtaggagacagagtcaccatcac
ttgccgggcgagtcagggcattagcaattatttagcctggtatcagcagaaaccagggaaagttcctaagctcctgatctatgctg

Figure 12a Unit1 Seq ID 187 (con't)

catccactttgcaatcaggggtcccatctcggttcagtggcagtggatctgggacagatttcactctcaccatcagcagcctgcag
cctgaagatgttgcaacttattactgtcaaaagtataacagtgcccctctcactttcggcggagggaccaaggtggtgatcagtcc
cacagtgactcagatgtaatacacaaacctcccggcagtgcaaggagcagataatacccttaactgtctgtcttacaggttccacc
tccatcaatacccatgctgcagggctcaggtcctcttaggctgccaggctgcaccctgctggctccctccccactaccctacac
ccacccttcagtgtcccctgcatgcactggggcaacacttcctcacctgtccgctccctgctggagggccacagccacctggt
tgatacatcagcatagcaccagttcttccccaagctggccctcccttggactctctactgagccccatttcctccctctcctctcca
ggtgccagatgtgccatccagttgacccagtctccatcctccctgtctgcatctgtaggagacagagtcaccatcacttgccggg
caagtcagggcattagcagtgctttagcctggtatcagcagaaaccagggaaagctcctaagctcctgatctatgatgcctccag
tttggaaagtggggtcccatcaaggttcagcggcagtggatctgggacagatttcactctcaccatcagcagcctgcagcctgaa
gattttgcaacttattactgtcaacagtttaatagttaccctcacaccttcggccaagggacacgactggagattaaacccatggtg
acacacagcagtgaggaagcgatgcacaaacctcctgacagtgcaaggagcagccggc

Figure 12b Unit2 Seq Id 188 gccggcaggttttgctgtctctgtttgatggtggcacaggacctcaccacagccctaccttcactgtcctgcaatatgggtggctgt
gcacggtgtcctgaacacgtcccaacaagatgcacagcacigcatcaggcccagccctgcctgtagcagctgatgcccttgtc
cagcttctgcctgagctgcctctgtgctgggatgctccatgctgagctctgatcctccaaagtgcccatagctgtggctgggatcc
cttctgctctgatggtggtggcacattgcaggaacagagcccagaccagaacagctcagtacagagccagctccagcaggga
gagaatggggctgccagcagcaatgtggaacagctggggatggcacagagctgtgccttttcagggacaggtacagtgtgact
cagtacccagagtaacctctcatacaactacatataccaaggaaggcatttacaagcatggccatgcagagaagatataaatcat
cctcagtctcacagacctgctcagccataaggcatcaagggtgaaaaacctctatttttttttaaccctgatcaatccatcagttcctc
acctcccgctgaggcaatacggttggcgtccaccctggtcccttggccgaacgtcggatggctgctgtaagtctatagacagca
ataagttataacatcttcaggttgcaggctcctgatggtgagaatgtgtgaaatgtgtcccagacctactgccactgaaccgtgac
gggaccccagattgcaaactggatgcagcatagatcaggagcttaggaggattctctagtttctactgatactagcttaaataattg
caaatgccctgactcgcccagcaagtgatggtgactctctctcctacagatgcagtcagggaggatggagactgagtcatctgg
aaattacatctgactcctggagagggagagaaaacagggctctgtgtgtctgacacgcacagcctccttgtttggcagtgggg
tgaggctgctgagcacacagacacacatgggacagcaggagacccacatctgctccaggattgacatctatggctggtaccag
cagaagatacctggcaatgccccatcactgggatccatgctaacactggtagacccacaggcgttctcttaccattctctggggtc
caatccaggcctacacacatgaactgtcacactaactaccactgtggtctaagctgtggagaacactgcccattactgcggtggc
aatgacaggagccaaggcctgaggatggcacttatcaccaggatagcaggacaaggggttcacaagaaaaaaagaaaggttc
ttttttcctctcccgcttcctctcagtccagctctgtggtctcttctccttcctactgctctccttcacccctgtacatcagatcccagggct
tcgctgcatttctgctcctgcaggcattgcctggggccctgtggcaagaccagtgccagatgtgacatccagatgacccagtctc
catcctcactgtctgcatctgtaggagacagagtcaccatcacttgtcgggcgagtcagggcattagcaattatttagcctggttc
agcagaaaccagggaaagcccctaagtccctgatctatgctgcatccagtttgcaaagtggggtcccatcaaggttcagcggca
gtggatctgggacagatttcactctcaccatcagcagcctgcagcctgaagattttgcaacttattactgccaacagtataatagtta
ccctctcactttcggcggagggaccaaggtggagattaaagtattttgacaatgtgtagtaggaacataaacacagccacattcac
agtaaagttttcaggccaccttccttggtccccgagctttgggaattgtgacttatgttactgttttgggaattcaggaggccttgtcct
atctgaatggccaagaccttgactgttaccccagatcatattccaggaatgagggtgatactgggtatagaccccatcatccttgtc
cctctccaggagtcagatgtgatttccagatgactcagtctccatcctccctgactgcatctgtaggagagagagtcaccatcactt
gctgggcgagtcagggcatttgcaattatttaagctagtatcagtagaaactagagaatcctcctaagctcctgatctatgctgcat
ccagtttgcaatctggggtcccgtcacggttcagtggcagtaggtctgggacacatttcacacattctcaccatcaggagcctgca
acctgaagatgttataacttattactgtctatagacttacagcagccatcccacttttggccaggggaccaagctggagatcaaact
atggtgacaatgattaaaaggaactgaattaataaattataagcctgttttctgcccatcttcctttttggccatgcagaactgtggcca
tagcagtttcctgttccatctgcatggccatgctatgaatgcactccttccacaccgcagggcacaggagatgtctgaagcacag
ggatgtgctgctgtgctctggacacctctcatcagaagtggccatagctgtgtcccttttcttccatgtggggcatccactatccctgc
tattgccagcactcccagcaagaccctgccagtgccttctgctccttctaaccacagcagtgggtgctgccccagagctgctc
ctctggatgctgtgccccacatttcctgaacacacactgcccatccagcaatgtgggacagggaacaccacagcaggaagaga
cctcaatcacagccatagtggaggcagacagaaacctgtcattttagctctagacatcacatcactcccatatctccctgtgtctct
gtacctacaaaactgctgtcataggccccactaggacaggaacatgaatggggctctgcaaaggcagcgccacagcagctgtg
gacccagagagcagaactgactgccctcaacagctccgcccatgcagggagatgtgcagcaacaaggaggggaggaaatc
caacagtgccgccaccagtttgagatcgaccttggtccctccgccaaaagtgagagggtaactattatgctgtagacagtaataa
gttgcaaaatcttcaggctgcaggctgctgattgtgagagtgaattctgtcccagatccactgccgctgaaccttgatgggacccc
actttgcaaactggatgcagcatagatcaggcgcttaggggctttccctggtttctgctgataccagcctaaatcatttctaatgccc
tgacttgcccggcaagtgatggtgactctgtctcctacagatgcagacagggaggatggagactgggtcatctggatgtcacac
ctggcacctggagagggagaggagagaaaatggggctcagtgcctgacacacactgccctcctcctcctcctcatggggagg
agaccccagagcacacaagcacacacagaatattcaaacaccgacttctaatccatgcttaacagcaactatgactggtacaag
cagaagactcctgacaataccactggcactttgtaatacctccacaataagccccctctctcctctccctctccaggtgccagatg
tgacatccagatgacccagtctccatcctccctgtctgcatctgtaggagacagagtcaccatcacttgccaggcgagtcaggac Figure 12b Unit2 Seq Id 188 (con't)

attagcaactatttaaattggtatcagcagaaaccagggaaagcccctaagctcctgatctacgatgcatccaatttggaaacagg
ggtcccatcaaggttcagtggaagtggatctgggacagatttactttcaccatcagcagcctgcagcctgaagatattgcaacat
attactgtcaacagtatgataatctccctctcactttcggcggcgggaccaaggtggatctcaaacttagtgacggggggagat
gtgaaactctctacagccctgaattaaaacatggatgtttctgcctttctccctcaggatcacgctgggctctgtcactcaggcagg
ttcccctctgcatggccacggctttgaacatctttcctgttctgcctcattgtataggactctcccagtacctggaaacaccaaaaata
ccagatgtgacatccagatgacccagtctccatcctccctgtctgcatctgtaggagacagagtcaccatcacttgccgggcgag
tcagggcattagcaattatttagcctggtatcagcagaaaccagggaaagttcctaagctcctgatctatgctgcatccgctttgca
atcagggggtcccatctcggttcagtggcagtggatctgggacagatttcactctcaccatcagcagcctgcagcctgaagatgt
tgcaacttattactgtcaaaagtataacagtgcccctcccacctttggccaggggaccaacctggagaccaggcaaatgcagac
aacagttgtacagtactgcttccactgacacagagcagcaggtacaactgatgcactaacctcctgccagtgcagggagcagc
tggctctttttgctggctctgtttgatggcggtgctggttcctaccatggcccttccctcattgccctggactacatgtggcagggca
aaaatcacatccccagcactgacagcaggaacctgtggaccgctgagcagccaggccaaagctccctacttagagggatg
ttcccatggcacaaggctgggctggctgtgtttctcttctggcacgagggcagccacagaatctttcagatcaggatgattgttgt
gatctgctcctacctcagctcaactggcatcacctacagcacagtgcccaggcctgtgtgcaggtggctgtcagagatctccaag
gaggagactccatgatctctccgggcagcctggatcagtgctacattacctgcggagtaaggatgtgactcctgactctggccag
acagaacctctgcgttcagtctgtgccactgcctcctgtactggtgctgaatgctgctggaaaaagcctggctctgttcactttgca
ccctcctttcaggttagcgtaagggagaggagagaaaataggggctcagcaattgcccaacatgcacagccctcaccaggctgt
cagatgaggcacgcaattccacaaggacacatgggtagcaggataccgttccagatgcgacatccagatgacccagtctcca
tcttccgtgtctgcatctgtaggagacagagtcaccatcacttgtcgggcgagtcagggtattagcagctggttagcctggtatca
gcagaaaccagggaaagccctaagctcctgatctatgctgcatccagtttgcaaagtggggtcccatcaaggttcagcggcag
tggatctgggacagatttcactctcaccatcagcagcctgcagcctgaagattttgcaacttactattgtcaacaggctaacagtttc
cctctcactttcggcggcgggaccagggtcgatctccgaccatggtgacacacagcagtgaggaagtgatgcacaaacctcct
gtccgtgcaaggagcagctggcaggttttgctgtctctgtttgatggtggcacaggaccccaccacagccctaccttcactgacct
gcaacatgggtggctgtgcacggtgtcctgaacacgtcccaacaagatgcacagcactgcatcaggcccagcccctgcctgta
gcagctgatgcccttgtccaacttctgccagagctgcctctgtgctgggatgctccatgctgagctctgatcctccaaagtgcccat
agctgtggctgggatcccttctgctctgatggtggttgcacattgcaggaacagagcccagaccagaacatcttagtaaggagg
cagctccagcagcagcagaacggggctgccagcagcagggaatgatgctgtgccacagtaggaacagggaccaagaggat
cacttcccacgcaataaagtataaaagagaggggcattcaaaaacacagccatgcagagcagagagaaacctgactcagcccc
acagtcctgctcagccttaagtcagcaagtgcagaaaacctccatttcaactcaggtctgtaactcagttccacatcctcttttgtctc
tataccagcattagtgctgctatcccagccaccacagcctcatcttctgaccttagtgacaactaaccacaattggtcttccagggc
ccagggaaatagctgcactgggacaggagctgccagtgaccatgaggttctgcatgagtgggctgtgttgtgggcagttcagg
gtataaagaaaggagttggagtccatggcatagacccattggcataaggatgtgcatctgctgggatcacaccatggcctgtgcc
cctctcctgctggcagtgctgacccacagctcaggtgccccaggaacaccccgttgtgcccagcctttgggcactgggccccatc
cccctgcttttttaagacttggcatcaattcaccacaacacctctctgcagcaccagtttgatgtccagcttggtccccgggccaaa
agactccggagggtaactattaagctgttgacagtaataagttgcaaaatcttcaggctgcaggctgctgattgtgagagtgaattc
tgtcccagatccactgccgctgaaccttgatgggacccactttgcaaagtggatgcagcatagatcaggagcttaggggcttttc
cctggtttttgctgataccaggctaaataactgctaatgccctgactggcccggcaagtgatggtgactctgtctcctacagatgca
gacaggaaggatggagactgggtcaactggatgtcacatctggcacctggagaaggagagaagagaaaatgggctcaacaa
gagcctgacacacacagccctcccaagcagcagtgggatggggaacagcaccattaaaggaaaagggacttcagccatagc
cacatcaaaggatgagagcccagcccagagcagcccagcacagaggcagctccatggagcagggctggggatgacaagat
gctgtatctttacaaggataggtacagtgtgggtaagtgtcagagtaatctctcatacatctaggtacagacaggagggcatttaca
aacacggccacgcagagaggacagaaacctgcctcagccccacagcgctgataagccattactcagtaagtgcagaaagtttc
cattttaactcaggcctgttactcagttttccatctccctgtgtcactgatccccaacttggactccagtgaaggctaaccatgatca
gccttctgtgagctgagaaaaggagtgtagtgagcagggagagcactgcaataggagctgatagtgatcacacaggcctgtac

Figure 12b Unit2 Seq Id 188 (con't)

tatgggcagatgggagtttaagagtgaattgcggtccatggcatatgcctgtcagcatagggatgctggaggaattgcaccttgg
catgagcccctctcctcctggtgatgcttgcccacagctctgacgtcctgggaaggctcactgcaccttgttgtcagtgaaactgc
aataagctatcaagatttgatataattctgcccctctgatctacttgtgagaccacacctggagtactgcatccagttctggtaccac
caacacaaaaaggacatggagctgctggagcagggccagaggagggccatgaagatgaacagagggctgaagcacctccc
ctatggggacaggctgagagacatggggcttttgagactggagaagagaaggctccatgggacctttcagtgtccttccaatact
tgaaagggtccttgaggaaagctggggagggacttcctataaggacatatagcaacaggacaaaaggaaagggttttaaactg
gaagaaagtagatttagtctagatagtaacaagaaattctttacagtaaggatcacgagacactgaaacaggttgcccaaagcag
ctgtggatgcccctccctggaagtgttccaggccaggctggatggggctttgagcaacctgttctagtgagaggtgaccctgcc
tacagcaggggagttgaacctagatggtcttaaaggtccttccaacccaaatcattctatggcaattctatagagaacacctatgc
tgagagtagctacaagtatggctggttgtgccagatgtgtcatctggatgacccagtctccatcctactctctgcatctacaggag
acagagtcaccatcagttgtcggatgagtcagggcattagcagttatttagcctggtatcagcaaaaaaccaggaaagcccctga
gctcctgatctatgctgcatccacttgcaaagtggggtcccatcaaggttcagtggcagtggatctgggacagatttcactctcac
catcagttgcctgcagtctgaagattttgcaacttattactgtcaacagtattatagtttccctccgactttcggccctgggaccaaag
tggatatcgaactcacagtgacatggagcaattaaaaatgatgcataaccttttgcacatctgtaatgctataaggtgagagaaagt
aagcaataatagcagagcagcacaatcctaggctacagcaaatgagaacaagcccagatgcagccacagaaataaagaaaaa
aaaactgcttaccttagaaagcctcatatagacagggatctccagcaagataccacacctccactgccaaccccttaaatgagg
gctgggatgggctggatcctggctccaccccttcaatcactcaggtacattgcacacacctgagctcccctggctggccctgcc
ttcccaccaggtgctcaatcactgctttgggctgtgactcagcatctccactacagcatcacagggagcggttgtcggtctctgct
gttcctatgtgggtgccccgggacacctgaaggcatgagtggcagtgagggctcccagctctatccatggtgaatttgagatcca
ccttggtcccaccgccgaaagtgagagaataactattatactgttggcagtaataagttgcaaaatcatcaggctgcaggctgctg
atggtgagagtgaattctgtcccagatccactgccgctgaaccttgatgggacccccactttccaaactggaggcatcatagatca
ggagcttagggcgcttccctggtttctgctgataccaggccaaccagctactaatactctgactggcccggcaagtgatggtgact
ctgtctcctacagatgcagacaggggtggaaggagactgggtcatctggatgtcacatttggcacctggagagggagaggagag
aggggagaaaatggatctgagcaattgcctgacacacacagccctccccagactgtgggatgaggccctgtgccgcagtca
catgtggaatatcaagacacacacatctatgacaatcacaatctgattatcaaccggaccagaagtgacatccagtcacccagtct
ccatccacactgtctgcatctgtaaggagacagcgtcaccatcacttgccgggcgagtcagagcattggtagtaatttagactggt
atcagcagaaaccagggaaggcccctaagggcctgatctatgctgcatccagtttgcaatctggggctccttcgcggttcggtg
gcagtggatctgggacagattttactctcaccatcagaatcctgcagcctaaagatgttgcaacttattactgtcaacagtataaaaa
ttaccctatcaccttcggccaggggacacgactggagattaaacagctgctcctcctgggcccatctgctgagagtgattctca
gagcagccaggcttgaaggtcctgcaggttttgttggaaggggccaggtgactcctctgaggccccctccttcctcctccttg
gcggcagcagtacacactttgggtaaccttccgtgtctgctgagatgcagtcagataggagaattctctgatccctcaccacctgc
acacaggggcagtgtccccaggtgtccacatcagacccaggttgcacaggtctcctacagagaatgtctctctggggtctcagc
agagagaggaccagtgtgtgtagaggtccacgctctcctcacggctcagcccagctttgctgctgctgctccacctgtgacagg
ggctgcagggcttgcacagcccagaacctggagaagctgagcagctcctcagtgtggttctggtggacgtcactgaggccag
ggcggcttctgctttctcttatttcctaatggcctttgtaacataaaagagcaataaatagaaaacatagtgagggctatgatttataa
aactggctgtgcttggatcctgccacacactgggagtcctacatggagtttgtgctctggactgtggcctgacccagcctcagct
gacaggctcatccgggaaactaccagcacgtggaggattttctctctctctcttctctctctcactttgtctttcaccaatgctcagtc
tttcaagtaaataaataaataaatattttaaaaatgggaaatattacatttaataaaataaatggggggcacatgtgcaatcgtgtca
gttttcaatctgatggagtagttcttgattcaatgcaaaatcaagtagaacattctcatccaattgcactaatagcagcttcactgttgg
cacataaaggcacacaaagaatagtagcacaaattcttaggcctgaaataattggaagaagtcgaacagagcccttatgtcata
gatctttcattttagtgggccgggcagatgagaaacaaaccaatgacgttccaactgtgctcccactgtgtccatgtgatgtgcctc
ccatggagcagggccagtgctcaggacaatgggctgtgggtgtgcaggtgcatgtgtgcctccttctgtctccacctagacag
ggcagaggcagaggcagaggagagggaatgtatcgggcaactccacatctgtgtttcctgaaaaataaactcattgtactctcg
gtgatggtcgggtagacaaactgtcctgacaaaagatttaagatttctcatgtccctgtagcataaagtcagtcagcacacaggtc

Figure 12b Unit2 Seq Id 188 (con't)

agagggaataatcagtgcccagacactggagataaaaaaaatggagcccagtttagtgcgcattagcagggaatgtgatcaga
agtggagcagtgggcttcaatccagtgtctgatgtaggctgctggctttgcaagtggcaacttaatccatgtaccatgatgccagt
ctaccctcctctctagattttcttagagataaagtgaaggtttcaggagagaggagagaaggaagttattttcttgatgtcttcagac
ctatggtgaggccttgaactttcactttctttcctcctgcatccttgactcagaactctggctgcaggtgggagagcacacatgtgt
gatctctcatctaagcacctgtgttatccttctgagtcctggtctctggcagccgcttgttctgaggatgtttattctgagtcagtacag
aggtaagtgtgggtagaagtctcgtctctcagagacaatctccctggtgcagcggtctccatgaggggacaagatgagggatca
aaggacaaacaggtgaaagacatggacctcagctttaaggtgtaactaagtattccctagaaaagcatttctactaaagaattcca
ccataagcatgaacaaattacaccttcttgtcctccagttcaattataggggttggcaaatgtccctcagggaatttgggaggtgatgt
ctcctggtggaagcatgcgcactgcaggtaaacttgtgcagccctggtctgagctggggcagctggagacacagcccctggac
tgagttctgaactgccctgggcccttcagctgggcacagccctgccccgccctgctcatttgcatgtccccagagcaccgccc
acctctctgggcatttaggagcaggctgctcccgccccatgcaggaggcagtgccaggcaggacccagcatggacatgaggg
tccccgctcagctcctggggctcctgctactctggctccgagtactcgttgcgcccggtcggggactgtgggcacggggctct
gtcccattgctgcgcgggcagggctgtgcgtgcggggccgtcactgattgccgttttctcccctctctcctctccctctccaggtg
ccagatgtgacatccagatgacccagtctccatcctccctgtctgcatctgtaggagacagagtcaccatcacttgccgggcaag
tcagagcattagcagctatttaaattggtatcagcagaaaccagggaaagcccctaagctcctgatctatgctgcatccagtttgca
aagtggggtcccatcaaggttcagtggcagtggatctgggacagatttcactctcaccatcagcagtctgcaacctgaagattttg
caacttactactgtcaacagagttacagtaccctctcactttcggcggagggaccaaggtggagattaaaggtaagtggccgttt
cactgattcctcaccgtttctgcctgattggtttgttttccacttttcgctgtttgtgtgtctttgttggctggaggtcagggttctaac
gaatttctttccaagatgaggcacagaggagggaaaactgtctgagatttccaagtcaaaataacttccccggggagagggcttg
ccgccttgtcagggagggttttgtggagggagaaggtaaagggagccaccgtgaagttcctattccgaagttcctattctctaga
aagtataggaacttcccctttctgtccaactgtgaggtcttggtcccctggatcacctgggcaagtttgtgatgtttcagttaaatgag
ccattcctggcgaccccaaaagtaaatagaagaaaataatcaaaagcggagaagacagaaatttgggggtttgggagaatagg
agagaaacagcagaagtttctctacagttgccgtgtggtgggactggccgcaaagggaggttttgtgaggggtgggatgacag
agtgacttacttttggctcagggaggcgcgcc

Figure 13a Unit 1 6607bp Seq ID 189 ggcgcgccataacttcgtatagcatacattatacgaacggtaaggggagtgcggctccaccaggggggcgcgcaagacacact
gagtccagattctggtcctgctcaggcacagagggagatgaagccctggtttcctgtcagggatttgggtttcctctcctacagtttt
gagggaagacttctacttcaggattctgtcccttacactgacgccactgacgtagagaagctttatgtgacaggaagaagtcttaa
atggacacattcaggtttgtgaacgatgacagtggtcaccagggtcagagatgtgagacaatcaggggacctcgtgagtgttgtc
cagtctgactcaggacagcgttccaggacactgccgactataagacaatttagttttccttcaaacccagacagacccgagcca
gagtcttgatttgctacctcagtttataagtcgtcccatcctcctgtcagagcagcctgtgtgctgcactgaaccaaccgtcttatttt
aactgtgggtgttctgcattcacttctacagactttatacccaatctccatttccctttaatcctgaaacagtctgtggtccctgtgtgc
acttccagctgatctggttctgctccagtgtcgtgggaaccctgcacctgctgtggttcagggagagcagaaagtgggacaca
gagcggctgtgcactctggggctggagtccacatcacggggagctgtgtctgtggctccagcatgatgcccagtgtcctgagg
ctgaatcacagctgcaggaagagccagtcccagagaccatgtgtccagagtccctgctcttcactccatgtctatgctgactggg
gtcatcaatccatttgtgttctttcatcagtattagagagggagacacccaggctgcatatcacattgctggatggagcccatttgca
cgcttcccatacttgtactgacagtgcaccctggaagacagtacatgatggatctgtatgaggccccatcaccaaggtgggaac
actgatgcagttcatgctcctgggttccagctgacaagcttgagtccactgcctttatttatcatctccataaaacatggccaacac
aacaccagtattcaaagatcaatcgtcatgattggccatcgttgctatttcatattcctaaatgtttgataaataatattgagtatagctc
tatgaggtacaatgatatgtgtggacaaaatgaatgcatattgagtggaattatgaagtcaggcttgatgacacattcataccacaa
cacatgtttttggtggagttcacctgtctcctgctcttaagagatttccactcacaatattctcttaacctctgtcaccatgctgtgcagt
agatccctcagtgtgtggagcctgtgggactaaaactctgaccttgctccagcgtctcctctgttcctccctcgctcagactttggtc
ttcaccattgtacttcctgcctctgtgccttcagcctttatcccatgtaggtagcatcacatattatgtgtcttcctggcctggatgctta
gcagagtgtacttttactgacatattatcttaggcacattattctccgggatcatccaagttgtccaaaatcacagaatttcttactctgt
actgcttttaaacttccttttaaaatgtaactttgtccatttctttcattttccattcttgcttccatgagatgtcactggatcatatgtgtgaa
ctcttttgaatggcggtgctttaaatgaacaaggaactgcagaggtgtttgccacagtgactgcagatcccgtggacacctccctg
ggatttcatattcattgtaccatgcaatggtgcttgaagatcatgtaataattctgtttctagttttttgatgcttttccataatggtttacta
attaacctgacacagacttgtaccagggttatcatctctctctacctccataaaacatgtcagctctggtatgtctgataatagtcattc
taacaggagggatgggatgtctcattgtgcttctaacatggacatacatgatggtcctagatttgtagcattttatatgtttgtctttata
tcttcttttgaaatttatagatgtaacataaattttaaaatttatcattttattggccagcgcatggctcactaggctaatcctccacctgc
ggtgactgcaacccagtttctagtctcggtcgggcgccggattctgtcccggttgcccctcttctaggccagctctctactgtggcc
cgggagtgcagtggaggatggcccaagagcttgtgccctgcaccccatgggagaccaggagaagcacctgactcctggcttc
ggatcagcgtggtgcaccggttacagcggccattggagggtgaaccaacggtaaaggaagacatttctctctgtctctctctctgt
cactgtccactctgcttgtcaaaaaagtgtaccatttatttaaaaatttgtctttatatatttgtccaaaaccacagagagactgagact
gacagtgatcttctaattcctggtcacttctcagatggctaccaaagattcagctgggtcaggcgacagccaggtgcttggaattct
gtccagggctcccacgtgggactacttggaacttcacctatggcctcccagaggggcttaggaaggaatatgagactggaacc
aaactaggacacagcactcagcatcctcatacaggagcaggaatccatcaggctcactccagtgctgctcctgtcaccaccttat
catcactgcatttaaggaattgatttcttcccttgggattcagttgtttgagatcttcaacattaggaaataggctttcaatcatatgtata
attaatcttcaatttattttaagtatctattttattttagagacagtgttatagcaagagatgaagagaccaacagatggagagagaag
cttctgtccagtggttcacttcgtgaatggctgcaaaggctatgatggctgagcctaaagccaggagcctggaacttcctccagttt
cccacagggctggaaggggacaaacactttggtcatggtcgacagtgatcaccattgcaatgcctacatctgtgagttcaattgtg
gactgcatatacaaataatgtcacatactatgtgtccacatctacctggatcatttctttagtatgtatgctccaggctgacccatgttt
cctactgacagaacgacctccttcttaatactgaataatattccatgtccaaatgtgaaagaatccattcactgttctgtgaacacttg
cttaattgtagactgaactattatgaacacagctgcattacctgaacccaggactgcgggtgaattgtgacacagtgacttctaccc
agtgcttgagctgaactcagagtcatgattacagaacagggaagaggggggaacacagggcagctgataacaggacgcaaag
caccactcacaggaaggaataattctgcctacaccacagtgggctgactcagttcaccacaacccatgacaggttccacaaata
actagaactgaggtctccaggcctcccaacagagtgatggaaaggaggtggaaatgtgcatgacactgagttcatctgtgccca
tttctaccatgcacattccaatagcacacaaaccccactaccatgtacagtgttctgtgttcaggaacagttttaaactaaagcaatg

Figure 13a Unit 1 6607bp Seq ID 189 (con't)

gatgaataaatgaacaacacatagttaaccttaaaaaatcaacttgcagtccttcatctatttaaaagtgggcagcaggcattagga
caaaattggctaagtccccactagggtcacccgtgttcccatcagagaactgactgagcccagcctcacggcttcccacactttc
cctcataatgcatcatgggaaactgtagatgacactacaggcaaaggagcccctaccaccgacgttggaattacagacacagttt
cttgcttcagggttcagaaagactaactcctaggggtcataggcatttgggatgtctagggctctcaacccaaaggcagaaatctc
ccattgtcacctttctgtccatctctacatttctgtaactctcaccccttctatctctatctctgtcccaatgtctttcatatagatgataag
gaactaatgggatttaaataaatgaggaacatgatattgctaacactggatattaagggtgcacacatattaaaatgaaacaaggta
tctgccttcaactttttaaaataattataacataaaaattcatatgatctgaatcatatcacagccatcaccgtacacccccaggtcac
cacatctgccctgggcgctgtcctgtctgaggcgtctgaccccatgcctgctatatagggggcagctcatgcaaatggggcctccc
tgtgcccatgaaaaccagcccagccctcaccctgcagctctggcacaggagctccagcccaggactccaggtgtccactca
gtgatcgcactcaacacagacgctcaccatggagactgggctgcgctggcttctcctggtcgctgtgctcaaaggtaatgatgg
ggaacgcgggacactgagtctgggagaggatgtgagtgagagacacagagagtgtgagtgacagtgtcctgaccatgtcgtct
gtgtttgcaggtgtccagtgtgaggtgcagctgttggagtctgggggaggcttggtacagcctggggggtccctgagactctcct
gtgcagcctctggattcacctttagcagctatgccatgagctgggtccgccaggctccagggaaggggctggagtgggtctcag
ctattagtggtagtggtggtagcacatactacgcagactccgtgaagggccggttcaccatctccagagacaattccaagaacac
gctgtatctgcaaatgaacagcctgagagccgaggacacggccgtatattactgtgcgaaagacacagtgaggggccctcagg
ctgagcccagacacaaacctccctgcaggtgtcgcgcggctctaccaggggggcgctcaagacgcactgagtgcagattctggt
cctgcacaggcgcagaagatgaagccctggtctcctgtgagggaattggggtttcctctcctgtagcagttttgagggaagaatt
ctactttttgattctgtccttcccaacttcactgacggagagaaagtttgatgtaaaaggaagaagtcctaattgaacaatttggttcat
ggacagcgactgtgctcaccagggtcagagatgtgggaatattgaggactctattgagtctcttccaacctgactcaggacagca
ccctcagggcactgaaagctttggacagtttcagttttccctgtataaccagggacagctgagacagggtcgttgatctgttaaac
agcaactattccactcatccctcctgccacaaccagcaagtgtgcactaaaccaaccttgactctacatgtgggtgatccacac
tcactttctgcagactttaaccegacctgcatttccctttaatcctggaacagtctgtggtccttgtgtgaacgtcacagcactcagga
atgtactgcagctcagctgtgtctcaggctgagcttctgcaggcacctgggaagcctacagggacttcctcatcctctaggtcctg
ggaccctcctgggggctccctgcctgaactcaggagggaaatgccctggacatcagcagtcaaggtcatcactgaatggaaa
gtgttgggtgtgcacttccagctgatctggttctgtcaagtgtcgtggcacctcctgcacctgctgtggttcagggagagcagaaa
gtgggacacagagtggctgtgcactctggggctggagtccacatcacggggagctgtgtctgtggctccagcatgatgcccag
tgtcctgaggctgaatcacagctgcaggaagagccagtcccagagaccatgtgtccagagtccctgctcttcactccatgtctat
gctgactggggtcatggatccattcggagtctttcatcagttttagagagggagatagatacacaggctgcatatcagagttctgg
acagagcacatttacactatttctatacttgtaagtgaaaatgcaccctaaagacagcagatgatggaccagttatgaagccccat
gaacaaggtgcaaacgctattgcagttccatgctcccgggttccagctgccaagcctcaaattaactggcatttatttatcatctaca
taaaacactgagaaacacaacaccagtattgagcgaactgaatctgtagttggccattttgtcattttatttttcataaatgtttgataaa
taataattgaacatagacatgagataaatgatatgtgttcaaaaatgactgtatcaaattgatggaattatgaagtcattcttattgaca
tgctcatcacaaaatccacatgttcccatggtcgaatgtcagtggtctcctgttttggaattcaatagacccaatattcatacgcgt

Figure 13b Unit 2 15699bp Seq ID 190 ggcgcgccgcaacccagtttctagtctcggtcgggcgccggattctgtcccggttgccccctcttctaggccagctctctactgtgg
cccgggagtgcagtggaggatggcccaagagcttgtgccctgcaccccatgggagaccaggagaagcacctgactcctggct
tcggatcagcgtggtgcaccggttacagcggccattggagggtgaaccaacggtaaaggaagacatttctctctgtctctctctct
gtcactgtccactctgcttgtcaaaaaagtgtaccattttatttaaaaatttgtctttatatatttgtccaaaaccacagagagactgaga
ctgacagtgatcttctaattcctggtcacttctcagatggctaccaaagattcagctgggtcaggcgacagccaggtgcttggaatt
ctgtccagggctcccacgtgggactacttggaacttcacctatggcctcccagaggggcttaggaaggaatatgagactggaac
caaactaggacacagcactcagcatcctcatacaggagcaggaatccatcaggctcactccagtgctgctcctgtcaccacctta
tcatcactgcatttaaggaattgatttcttcccttgggattcagttgtttgagatcttcaacattaggaaataggctttcaatcatatgtat
aattaatcttcaatttattttaagtatctattttattttagagacagtgttatagcaagagatgaagagaccaacagatggagagagaa
gcttctgtccagtggttcacttcgtgaatggctgcaaaggctatgatggctgagcctaaagccaggagcctggaacttcctccagt
ttcccacagggctggaaggggacaaacactttggtcatggtcgacagtgatcaccattgcaatgcctacatctgtgagttcaattg
tggactgcatatacaaataatgtcacatactatgtgtccacatctacctggatcatttcttttagtatgtatgctccaggctgacccatg
tttcctactgacagaacgacctccttcttaatactgaataatattccatgtccaaatgtgaaagaatccattcactgttctgtgaacact
tgcttaattgtagactgaactattatgaacacagctgcattacctgaacccaggactgcgggtgaattgtgacacagtgacttctac
ccagtgcttgagctgaactcagagtcatgattacagaacagggaagaggggggaacacagggcagctgataacaggacgcaa
agcaccactcacaggaaggaataattctgcctacaccacagtgggctgactcagttcaccacaacccatgacaggttccacaaa
taactagaactgaggtctccaggcctcccaacagagtgatggaaaggaggtggaaatgtgcatgacactgagttcatctgtgcc
catttctaccatgcacattccaatagcacacaaaccccactaccatgtacagtgttctgtgttcaggaacagtttttaaactaaagcaa
tggatgaataaatgaacaacacatagttaaccttaaaaaatcaacttgcagtccttcatctatttaaaagtgggcagcaggcattag
gacaaaattggctaagtccccactagggtcacccgtgttcccatcagagaactgactgagcccagcctcacggcttcccacactt
ttccctcataatgcatcatgggaaactgtagatgacactacaggcaaaggagccctaccaccgacgttggaattacagacaca
gtttcttgcttcagggttcagaaagactaactcctaggggtcataggcatttgggatgtctagggctctcaacccaaaggcagaaa
tctcccattgtcacctttctgtccatctctacatttctgtaactctcaccccttctatctctatctctgtcccaatgtctttcatatagatgat
aaggaactaatgggatttaaataaatgaggaacatgatattgctaacactggatattaagggtgcacacatattaaaatgaaacaa
ggtatctgccttcaactttttaaaataattataacataaaaattcatatgatctgaatcatatcacagccatcaccgtacacccccaggt
caccacatctgccctgggcgctgtcctgtctgaggcgtctgaccccatgcctgctatataggggcagctcatgcaaatggggcct
ccctgtgcccatgaaaaccagcccagccctcaccctgcagctctggcacaggagctccagccccaggactcccaggtgtcca
ctcagtgatcgcactcaacacagacgctcaccatggagactgggctgcgctggcttctcctggtcgctgtgctcaaaggtaatga
tggggaacgcgggacactgagtctgggagaggatgtgagtgagagacacagagagtgtgagtgacagtgtcctgaccatgtc
gtctgtgtttgcaggtgtccagtgtgaggtgcagctggtggagtctggggagccttggtaaagcctgggggtcccttagactc
tcctgtgcagcctctggattcactttcagtaacgcctggatgagctgggtccgccaggctccagggaaggggctggagtgggtt
ggccgtattaaaagcaaaactgatggtgggacaacagactacgctgcacccgtgaaaggcagattcaccatctcaagagatgat
tcaaaaaacacgctgtatctgcaaatgaacagcctgaaaaccgaggacacagccgtgtattactgtaccacagacacagtgagg
ggccctcaggctgagcccagacacaaacctccctgcaggggcgcgcggctccaccaggggggcgcacaaaacgcactgagc
ccagattctggtcctgcacaggcgcagagtgagaccaagcccctggtttcctgtcagggatttagggtttcctctcctgtaacagttt
tgagggaagaattctacttttttgattctgtccctcccaacttcaatgacggattgaaagtttgatgtaaaaggaagaagtcctaaatg
aacaatttggatcatggacagcgactgtgctcaccaggatcagagatgtgggaatattgaggacactattgagtctcttccaacct
gactcaggacagcaccctcagggcactgaaagctttggacagtttcagttttccctgtataaccagggacagctgagacagggt
cgttgatctgttaacagcaactattccactcatccctctcctgccacaaccagcaagtgtgcactgaaccaaccttttgactttatatgt
gggtgatccacactcactttctgcagactttaacccgacctgcatttcccttaatcctggaacagtctgtggtccctgtgtgaacgt
cacagcactcaggaatgtactgcagctcagctgtctcaggctgggcttctgcaggcacctgggaagcctacagggacttcct
catcctctaggtcctgggaccctcctgtgggctccctgcctgaactcaggagggaaatgcactggacatcagcagtcaaggtca
tcactgaatggaaagtgttgggtgtgcacttccggctgatctggttctgctccagtgtcatgggaccccctgcacctgctgtggttc
tgggagagcagaaagtgggacacacagaggctgtgcactctggggctggagtccacatcacagggagctgtgtctgtgactc

Figure 13b Unit 2 15699bp Seq ID 190 (con't)

cagcatgatgcccagtgtcctgaggctgaatcacagctgcaggaagagccagtcccagagaccatgtatccagagtccctgct
cttctctccatgtctatgctgactggcgtcatcaatgtattttcagtctttcatcagttttagagagggagacacccaggctgcatatca
gagtcctggacagagcccatttacacaataccacacttgtactgacaatgcaccctggaagacagtagatgatggatctgttatga
ggccccatcaccaaggtgggaacactgatgcagttccatgctccagggttccagctgccaagccttgagtgcactgccttcattt
atcatttctataaatctccatatatacttccttttaaatataactctgtccatttgtcccattatccattccttcttcaatgctaatttcactgg
attatgtgtgtgaactcttgagaatgacgctgctttaattgaacaggggactgcagagatgtttgtcacagtgactgcacatcccgt
ggtctcctccctggatttcatattccttctacccaggcatggtgttggaggatcctgtgataattctatttctcagcttctgatgttttcca
tgaaagctttcctaatttacctgactccagcctttaccaggttatcatctctctcttcctgcacaacatgtgtcagctctggtatgtctgg
tgatactcagtctaagaaagggatgggtatctcattgtttctccaacatgtacgtgcatgatgatcccagatttaaagcatttttatac
atttgcctttatatattttattttaaaaattacagatacacttcacctcttttaaaacttgtatttgtgtatttgtccaaaaggaaaaagaga
cagagactgacagacagtgatctactgaatcctggtaacttccagatgcccataaaagctgagttgggtcagatcatacaggtg
catagaactcagtccaggtctcacacatgggataaactcagacttctcatactgcctcccagagtgcacattggcaggaatctgaa
attgggatctaaactgggacataaacctgagcatcctgatgcaggaggcaggaatcccacgtgataccctcaatgctgctcctat
cacccaccttgtcagtcactgcatttaaaccattgattgcttccctgtgattcagttgcttgagttcattcaacatttggatctaggctc
ctaatcatatgtacaattatctttcatttattttgaatatctatgtatttgatttgaaaggcagtattatagcaagagaggaagagaccaa
cagagggagagagaagcttccatccactggtttccttcctgaatggctgcaaaggctgggcaagggcaagactgtagccagga
gcctggaacttcctccagtttcccacagagctcgaaggggacacacacttgagtcatcgttgacagagttctctggtccatgagc
agggagctggatttgaagtgcagcaagcaagatctgaacccatgctgctgagtgaagctgcatagggatggcagcttaacctgt
ggggccacaatgttggggagtaggccatgagggttgctgcctgcattgaagggaatacgacccttagaaagacccttcaggcc
ggcgccgcggctcgccagactaatcctctaactgcagtgccggcactccgggttctagtccaagttatggcgccggattctgtcc
tagttgctcctcttccagtccagctctctgctgtgacctgggagtgcagtggaggatggcccaagtgcttgggccctgcaccctca
tgggagaccaggaagaagcacctggctcccggcttcgaataggcacagcgcgctggtggaggcggacatttgggtgataaac
caacggaaggaagacctttctctctgtctttctctctctctatctctgcctgtcaaaaaaaaaaaagaaagaaagaaaagaaaa
gaaagtaagacccttcagtaacttaattttttaaatttgagttataacacatgaatcagagaggagaatgagagaaagagagatgttc
cgacactgtgctttcccaaatgttgctgtggccaggtctgcttcccagcttagcccggtctcaggaaaacaatcaggtgcatccac
aagcgtgacagggcccaaaattcctcccataaacttctgggtcctggggctgcaggagcaggaaactggtactgggagccaga
gccacacatgggaccctggcactctcttgggggatgtgctcatcttaaacagtgcaaatttcaatttattatttcctttatttccatgaa
atttgatgcactcagatgcacctacgtgaaacctggtcctctgtgcatctctctgttaaaaatggaatccagcaaaagtgctccttgtt
ctgctgctggcagggagttctgcagacctcaccaggaagcccagtgagtgctaagggtggactggggcagagctgagtcct
gtggtgagggcatggatcaaggtgctggggactcctcttaccacactggagtggggacacatccacactgtactgatgatttct
cctgtaacgttgaaatggaccaagacctaagggaacccatgaatacacattgtaggtccattcacataaaaggaccaagagagg
gttcagtgtgcaatgagagcatacaatttatcactcatcccacatatgaataatgtcagactgccccgggacactctcatcagtctg
gacactatcatactaaggagtctgacgccagggctgctatataggggcagcacatgcaaataggctccctctgcccatgaaaa
ccagcccagccctcactctgcagctctggcacaggagctccagccccaggactcccaggtgtccactcagtgatcgcactcaa
cacagacgctcaccatggagactgggctgcgctggcttctcctggtcgctgtgctcaaaggaaatgaagggccagtgcccgag
ctcactaggctaatcctccgcctttcggcgccagcacacagggttctagtcccggttggggcgctggattctgtcccggttgccc
ctcttccaggccagctctctactgtggccagggagtgaagtggaggatggcccaagtacttgggccctgcaccccatgggaga
ccaggataagtacctggctcctgccatcggatcatcgcggtgagccggcctcagtgagctgacacggtgaccattggagggtg
aagcaacggcaaaggaagacctttctctctgtctctctctctctcactgtccactctgcctgtcatataaaaaggtaatgatggagaa
tgcagggcactgagtttgggagaggatgtgagagagagtgtgagtgacagtttcgtgatcatgtcgtctgtgtttgcaggtgtcca
gtgtgaggtgcagctggtggagtctggggaggcttggtccagcctggggggtccctgagactctcctgtgcagcctctggatt
caccttagtagctattggatgagctgggtccgccaggctccagggaaggggctggagtgggtggccaacataaagcaagatg
gaagtgagaaatactatgtggactctgtgaagggccgattcaccatctccagagacaacgccaagaactcactgtatctgcaaat
gaacagcctgagagccgaggacacggctgtgtattactgtgcgagagacacagtgaggggccctcaggctgagcccagaca

Figure 13b Unit 2 15699bp Seq ID 190 (con't)

caaacctccctgcaggggcgcgcggctccaccaggggcgcacaaaacgcactgagcccagattctggtcctgcacaggcg
cagagtgagaccaagccctggtttcctgtcagggatttagggtttcctctcctgtaacagttttgagggaagaattctacttttgatt
ctgtccctcccaacttcaatgacggattgaaagtttgatgtaaaaggaagaagtcctaaatgaacaatttggatcatggacagcga
ctgtgctcaccaggatcagagatgtgggaatattgaggacactattgagtctcttccaacctgactcaggacagcaccctcaggg
cactgaaagctttggacagtttcagttttccctgtataaccagggacagctgagacagggtcgttgatctgttaacagcaactattc
cactcatccctctcctgccacaaccagcaagtgtgcactgaaccaacctttgactttacatgtgggtgatccacactcactttctgca
gactttaacccgacctgcatttcccttttaatcctgaaacagtctgtggtccctgtgtgaatgtcacagcactcaggactgtacttgca
gctcagctgtgtctcaggctgagcttctgcaggcacctgggaagcctacagggacttcctcatcctctaggtcctgggaccctcct
gggggctccctgcatgaactcaggagggaaatgcgatggacatcagcggtcaaggtcatcactgaatggaaagtgttgggtgt
gcacttccagctgatctggttctgtcaagtgtcgtgggaaccctgcacctgctgtggttcagggagagcagaaagtgggacac
acagaggctgtgcactctggggctggagtccacatcacggggagctgtgtctgtggctccagcatgatgcccagtgtcctgagg
ctgaatcacagctgcaggaagagagagtcccagagaccatgtgtccagagtccctgctcttcactccatgtttgtgctgactggg
gtcatcaatttatttggagtctttcattaatattacaggctgcatatcagagtcctggacggagcccatttacacattcaccacacttgt
actgacaatgcaccctggaagacagtagatgatggatctgttatgaggccccatcaccaaggttggaacactgatgaagttccat
gctcctgggtttcagctgccaagccttgagtacaatgccctttatttaccatctccataaaacattggcaagcacaccagtattttcc
gttttgccgtttcatttttataaatgttttataaataataattggatatagacatatgaggtgcaaggatatgtgttcaaaattgaatgtag
caaattgatggaattatgaagtcattcttattgacatgctcatcacaaaatccacatgttcccatggtagattgtcagttgtcttctgtttt
ggaattctgtagacacaatatttgcttaactgctgtcaccatgctgtacagtagatccctcaacatgtggatcctgtgggactgaaac
tctgaccttgctccaatgtctcctctgttccatgcccttttcttccattattgattccttcttccatgaaaatttcactggattatatgtgtga
acactcgtgaacgacgctgctttaattgcacatggaactgcagttgtagtttctatagagactgtgaatcccatgcacatctccctgg
gatttcacattcctgctacccaaaatgctgtttgaagatcctgtgataactgtatgtctcagtttttgatgactttccataatggatttact
aatttacctgactccagccttgtacaaccagagtggtcatctctcttccttcacaagaattgtcagctctggcttgtctggtaatactca
ttctaacatgaaggatggacatctcattgtgcttctaaaatgtgcatacatgatgatctcagatttatggcatttttacatgtttgcttttat
atcatttcttaaattttatagatgtaatctacagttaaaaattcatagatttttattttaaaatttgtctttatgtatttatctaaaaccacaaag
agactgagactgacagtgagattctatctcctggtcactaccaagagggctcaaatgcttcagttagatcaggtgacagccagg
ggcttggaattctgtcaggtctccacatgggagtacttggaacttcacctatggccacgagaaccaaactaggacacagcactaa
agaacctgattcgggggccggcgccgcggctcactaggctaatcctccgcctttcggcaccggcacaccgggttctagtcccg
gtcggggcgccgtattctgtcccggttgccctcttccaggccagctctctgctgtggccagggagtgcagtggaggatggccc
aggtgcttgggccctgcaccccatgggagaccaggagaagcacctggctcctgccatcggatcagcgcggtgcgccagccg
cagtgcgacggccgcggcggccattggagggtgaaccaacggcaaaaggaagaccttttgtctctgtctctctctctcactgtcc
actctgcctgtcaaaaaaaaaaaaaaaagaacctgacacaggaggcagcaatcccacatgctaactccagtgctgctcctgt
caccaccttatcagtcactgcatttaaacaattgatttcttcccttgggattcacttctctgtgtttattcaacatttgcatataggctccta
atgatatggataattaatctttcatttattttaatatctattttattttgtttgaaaggcattgttatagcaagagatgtcgtctgtgtttgcag
gtgcagctggtggagtctggggggaggcttggtcaagcctggaggtcgcctgagactctcctgtgcagcctctggattcaccttca
gtgactactacatgagctggatccgccaggctccagggaaggggctggagtgggtttcatacattagtagtagtggtagtaccat
atactacgcagactctgtgaagggccgattcaccatctccagggacaacgccaagaactcactgtatctgcaaatgaacagcct
gagagccgaggacacggccgtgtattactgtgcgagagacacagtgaggggccctcaggctgagcccagacacaaacctcc
ctgcaggggcgcacaagacacactgagtgcagattctggtcatgcataagtgcagaaggagcccaagccctggtttcctgtc
agggaactggggtttcctctcctgcaacagttttgagggaagaattcttctttgatgattctgaccctgtactgactctctgatgtgac
aggagaagtcctacatgaacgaatttaggttcagtggtctccagtatcagagatgtgggacaatctggggacttagtgagtgttgt
ccagcctgagtcaggacagagttcataggacactgccgactttagggcaattttacttttcccttttcaatccagcaatagctgagcc
aggggtttgagtttaaaaatctgctatttaagtatctctctccttttcaaaacgagcgactgtgctgaactgaaccaaccgtcttatttaa
actgtgagtgttctgcatcatttctaacagactttatacccgatctccatttcctttaatcctgaaacagtctgtggtccctgtgtgaac
gtcacagcactcaggaatatacttgcagctcagttgtgtctcaggctgagcttctgcaggcacctgggaagcctacagggacttc Figure 13b Unit 2 15699bp Seq ID 190 (con't)

ctcattctctaggtcctgggaccctcctgtgggctccctgcctggactcaggagggaaaaacactggacatcagcagtcaaggt
catcactgaatggaaagtgttgggcgtgcacttccatctggtctagttccgctccagtgtcgtgagaccacctgcacatgtgtggtt
cagggagaggagaaagtgggacacacagtggctgtgcactctggggctggagtccacatcacggggagctgtgtctgtggct
ccagcatgatgcccagtgtcctgaggctgaatcacagctgcaggaagagccagtcccagagatcatgtgtccagagtccctgct
cttcaattcatgtctatgctccaaatgtcaatccatttggagtctttcattaacattacagtgggagtcactcaggctgcatatcacatt
gctggatggagcccattttcacgctttcccatacttgtactgacaatgcaccctggaagacagtagatgatggatctgttatgaggc
cccatcaccaaggagggaacactgatgcagttccaagctcctgggttccagctgccaagcctgagtgcactgccttttttaatcat
ctccataaaacattggcaaacacaataccagtatgcagagatctgaatcttcatgactggccattgttcatccttttatccatgtagc
tacctacatcacatattatgtgtcttcctggcctggatggttagcagagtgtactttttagtgacatattatcctaggcacattattctcca
gggtcatccaagttgtccaaaattacagaatttcttactctgtactgcttttaaactccttttaaaatgtaactttgtccatttcttcattttc
cattcttcttccatgagatgtcactggatcatatgtgtgaactcttttgaatgaactcttttaaatgaacaaggaactgcagaggtgttt
ggcacagtgactgcagatcccgtggacacctccctgggatttcatattcattgtaccatgcaatggtgcttgaagatcatgtaataa
ttctgtttctagttttttgatgctttccatacggttttactaattaacctgacaagacttctaccagggttatcatctctctctacctccataa
aacatgtcagctctggtatgtctgataatagccattctaactggagcgatgcgatgtctcattgtgcttccaacatggacatacatgtt
ggtcccagatttatagcattttacatgtttgcctatatatcttctttaataattatagatattatataaattttaaaatttatcattttatttga
gaacttgtctttatgtatttgtacaaaaccacagagagactgagactgtcagtgatcttctaattcctgcgtcacttccccactggcta
caaaagatttttgctgggtcaggtgacagccaggtgcttggaattctgtccagggctcccacgtgggagtacttggaactacacct
acgcctcccagagtgtgctcaggcaggaatatgacactggaaccaaacaaggacacagcactaagcatcctgatacgggagg
caggaatccctcaggctcactccagtgctgctcctgtctccaccttatcatcactgcatgtacacaattgatttcttcccttgggattc
agttgcttgagatcattcaacattaggaaacaggctcctaatcatatgtacaattaatcttcaatgtattttaagtatctatttattttatttt
acaaacagtgttatagcaagagaggaagagatcaacaaatgagagagaattccatccactggttaacttcctgaatggctgca
aaggctggggatggctcagcctaaattcaggagcctgacttggatcatggtagacagttttcaccattgcactgcctacctctgtg
agttcaagcttgtgcactgcatgtataactaatgtcacatactgtgtgtccacatctacctggatcatttcttttagtatgaatgctccag
gctgacccacattcctaatgacagaacaacctccttcttaatactgaataatattcttagtctaaatgtgaaagaatccattcactgttt
tatgcacacttgttctttgtagactgaactattgtgaacaaagctgcattacccaaacgcaggactgcgggtgaattgtgacacagt
gacttctacccagtgcttgagctaaactcaaagtcatggttacagaacagggaagcgtggccggcgctgtggctcactaggcta
atcctccgccttgcggcgccggcacactgggttctagtcacggttggggcaacggattctgtcctggttgcccatcttccaagcc
agctcactgctgtggccagggagtgcagtggaggatggcccaagtgcttgggccctgcaccccatgggagaccaggagaagt
acctggctcctgccatcggatcagcgtcgtgcgccggccacagcacgccaaatgcaacggccattggagggtgaaacaacgg
caaaggaagacctttctctctgtctctctctctcttactgttcactctgcctgtcaaaaaataaaaaaaagaacaggggaagagggaa
cacagggcagctgataccagggcagaaagcaccaccaaaggcaggaataattctgcccacaccactttgggctgactcagttc
accacaacacacaacaggttccaagaatgactagaactgaggtctccaggcctcccaacagagtgatggaaaggaggtggaa
atgtgaatgacagtgagttcatctgtgcccatttctaccatgcacattccagtagcacacaaaccccactaccatgtacagtgttctg
tgttcaggaacagtttttaaacagttttaaacagtttttaaactttaaggcaatggatgaataaggaaaaaaacatagttaaccttaaaa
attcacttgagtatttcatctatttaaaagtgggtgacaggcattaggacaaaattggctaagtccccactagggtcacctgtgttcc
catcagagaactgactgagcccagcctcacggcttcccacacttttccctcataatgcatcatgggaaactgtagatgatgctaca
agcaaatgaaccctaccaccgacgttggaattacagacacagtttattgctccagggttcagaaagactaactcctagatgtcat
aggcatttgggggtgtctggggctgtcaacccaaaggcataaatttccccttgtcacttttctgtccatctctactttctgtctctctca
cccccttctctctctatcactgtaccaatgtctttcatatagatgataaagaactaatggttatttaaataaatgagggacatgatattgct
aacactcgatatgaagggtacacacatattaaaatgaaacaaggtcattgccttcaagttttttaaaattatgataacataaaaattcac
atgatcttaattctatcataaccatcacccaacacaccaagaacacagacaacttcccagggccctgtcctgttgaggcatctgac
cccatgcctgctatctaggggcagcacatgcaaataggggctccctctgcccatgaaaacctgcccagccctcaccctgcagctc
tggcacaggagctccagcctcaggactcccaggtgtccacicagtgaacgcactcaacacagacgctcaccatggagactgg
gctgcgctggcttctcctggtcgctgtgctcaaaggtaatgatggagaacgcgggacactgagtctgggagaggacatgagtg

Figure 13b Unit 2 15699bp Seq ID 190 (con't)

agagacacagagagtgtgcgtgacagtgtcctgatcatgtcgtctgtgtttgcaggtgtccaatgtgaggtgcagctggtggagt
ctgggggaggcttggtacagccagggcggtccctgagactctcctgtacagcttctggattcacctttggtgattatgctatgagct
ggttccgccaggctccagggaaggggctggagtgggtaggtttcattagaagcaaagcttatggtgggacaacagaatacacc
gcgtctgtgaaaggcagattcaccatctcaagagatggttccaaaagcatcgcctatctgcaaatgaacagcctgaaaaccgag
gacacagccgtgtattactgtactagagacacagtgaggggccctcaggctgagcccagacacaaacctccctgctaccgttcg
tatagcatacattatacgaagttatggccggccacgcgt

Figure 13c Unit 3 13971bp Seq ID 191 ggcgcgccggaagcctacagggacttcctcatcctctaggtcctgtttctctcctgtggggctccctgcctgaactcaggaggga
aatgcaccggacatcagcggtcaaggtcatcactgaatggaaagtgttgggtgtgcacttccagctgatctggttctgctccagtg
tcgtgggaaccccctgcacctgctgtggttcagggagagcagaaagtgggacacacagtggctgtgcactctggagctggagtc
cacatcacggggagctgtgtctgtggctccagcatgatgccnagtgtcctgaggctgaatcacagctgcaggaagagccagtc
ccagagaccatgtgtccagagtccctgctctttactccacgtctatgctccaaaggtcaatccatttggagtctttcattaacattcca
gtgggagtcactcaggctgcatacagagtgctggacagagcccacttacaggctttcccatacttgtactgaaatgcaccctgga
agacagtagatgatggatctgttatgaggccccatcaccaagaagggaacactgatgcagttccatgatcctgggttccagctgc
caaaccttgagtacactgcctttatttatcatctccataaaacattggcaaacacaacaccagtattcagagatctgaatcttcatgac
tggccattgttcatccttttatcccatgtaggtagcatcacatattatgtgtcttcctggcctggatgcttagcagagtgtacttttactg
acatattatcctaggcacattattctccgggatcatccaagttgtccaaaattacagaatttcttactctgtactgcttgtaaccttcctt
taaaatgtaactttgtccatttctttcattttccattcttgctttcatgagatgtcactggatcacatgtgtgaactctttgaatgacggtg
ctttaaatgaacaaggaactgcagaggtgtttgccacagtgactgtagattccgtggacacctccctgggatttcatattcattgtac
catgcaatggtgcttgaagatcatgtaataattctgtttctagtttttgatgcttttccataatggttttactaattaacctgacacagactt
gtaccagggttatcatctctctctacctccataaaacatgtcagctctggtatgtctgataatagccattctaatagga.aggatgcgat
gtctcgttgtgcttctaacatggacatacatgatggtcccagatttgtagcattttatatgtttgtctttatatcttcttttaaaatttataggt
gtaccataaattttaaaatttatcattttatttaaaaatttgtctttatgtatttgtccaaaaccacaaagagactgagactgacagtgatc
ttctaactcctgggtcacttccccaatggctacaaaagcttcagctgggtcaggtgacagccaggtgcttggaattctgtccaggg
ctcccacgtgggactacttggaacttcacctacggcctcccagaggggcttaggaaggaatatgacactggaaccaaactagg
acacagcactcagcatcctcatacaggagcaggaatccatcaggctcactccagtgctgctcctgtcaccaccttatcatcactgc
atttaaggaattgatttcttccctttgggattcagttacttgagatctttgaacattaggaaataggctcctaatcatatgtataatcttcaa
tttattttaagtatctattttattttagagacagtgttatagcaagagatgaagagaccaacggatggagagagaagcttctgtccagt
ggttcactttgtgaatggctgcaaaggctatgatggctgagcaagaaaccaggagcctggaacttcctctagtttcccacagggc
tggaaggggacaaacacttgggtcatggtagacagtgatcaccattgcaatgcctacctctgtgagttcaattgtggactgcatat
acaaataatgtcacatactatgtgtccacatctacctggattatatcttttagtatgtatactccaagctgacccatgtttcctactgaca
gaacgacctccttcttaacactgaataatatccatgtccaagtgttaaagaatccattcactgtttatgcgcacttgttctttgtagact
gaactattgggaacacagctgcattacctgaacccaggactacgggtgaattgtgacacagtgacttctacccagtgcttgagct
gaactcagagccatgattacagaacagggaagaggggggaacacagggcagctgataacaggacacaaagcaccactcaca
ggaaggaataattctgcccacaccacagtgggctgactcagttcaccacaacacacgacaggttccacaaataactagaactga
ggtctccaggcctcccaacagagtgatggaaaggaggtggaaatgtgcatgacactgagttcatctgtgcccatttctaccatgc
acattccaggagcacataaaccccactaccatgtacagtgttctgtgttcaggaacagttttaaactaaggcaatggatgaataaat
gaacaacacatagttaaccttaaaaaatccacttcagtctttcatctatttaaaagttggtgacaggcactaggacaaaattggctaa
gtccccactagggacaccgtgttcccatcagagaactgactgagcctagcctcacggcttcccacacttttccctcataatgcaa
catgggaacctgtagatgacgctacaagcaaaggagccccctaccaccaacgtttgaattacagacacagtttcttgctccagggt
tcagaaagactaactcctaggggtcataggcatttgggatgtatgggctgtcaacccaaaggcagaaatctcccattgtcacaa
tttctgtccaactctacatttctgtaactctcaccccttctctctctatctctgtcccaatgtctttcatatagatgataaggaactaaagg
ttatttaaataaatgaggaacatgatattgctaacactggatattaagggtacacattgaattaagatgaaataatgtatttgtcttcaa
cttttttaaaataatgataacataaaaattcacatgatctgaattttatcacagccatcagcgtacaccccccaggtcaccacatctgcc
ctgggccctgtcctgtctgaggcatctgaccccatgcctgttattagcagcagcacatgcaaatggggcctccctctgcccatga
aaaccagcccagccctcaccctgcagctctggcacaggagctccagccccaggactcccaggtgtccactcagtgatcgcact
caacacagacgctcaccatggagactgggctgcgctggcttctcctggtcgctgtgctcaaaggtaatgatggagaacgcggg
gcactgagtctgggagaggatgtgagtgagagacacagagagtgtgagtgacagtgtcttgaccatgtcgtctgtgtttgcaggt
gtccagtgtgaggtgcagctggtggagtctgggggaggcttggtccagcctggggggtccctgagactctcctgtgcagcctct
ggattcaccttcagtagctatgctatgcactgggtccgccaggctccagggaagggactggaatatgtttcagctattagtagtaat Figure 13c Unit 3 13971bp Seq ID 191 (con't)

ggggtagcacatattatgcaaactctgtgaagggcagattcaccatctccagagacaattccaagaacacgctgtatcttcaaat
gggcagcctgagagctgaggacatggctgtgtattactgtgcgagagacacagtgaggggccctcaggctgagcccagacac
aaacctccctgcagggatgcgcggctccagcaggggggcgctcaagacgcactgattgcagattctgatcttgcacaggcgcag
aaggagatgaagccctggtttcctgtcagggatttggggtttcctctcctgtaacagttttgagggaagaattctactttttattctgt
ccctcaaacttcaatgacggggagaaagtttgatgtaaaaggaagaagtcctaaatgaacaatttggttcatggacagcgactgt
gctcaccaaagtcagagatgtgggaatattgaggactctattgagtctcttccaacctgactcaggacagcaccctcagggcact
gaaagctttggacagtttcagttttccctgtataaccagggacagccgagacagggccgttgatctgttaaacagcaactattcca
ctcatccctctcctgccacaaccagcaagtgtgcactgaaccaacttttgactctacatgtgtgtgatccacactcactttctgcaga
ctttaacccgacctgcatttcccttaatcctggaacagtctgtggtccctgtgtgaacgtcacaacactcaggaatgtactgctgct
cagctgtgtctcaggctgagcttctgcaggcacctgggaagcctacagggacttcctcatcctctaggtcctgggaccctcctgt
gggctccctgcctgaactcaggagggaaatgcactggacatcagcagtcaaggtcatcactgaatggaaagtgttgggtgtgca
cttccggctgatctggttctgctccagtgtcatgggacccctgcacctgctgtggttcagggagagcagaaagtgggacacac
agtggctgtgcactctggggctggagtccacatcacggggagctgtgtctgtggctccagcatgatgcccagtgtcctgaggct
gaatcacagctgcaggaagagccagtcccagagaccatgtatccagagtccctgctcttctctccatgtctatgctgactggcgtc
atcaatgtatttcagtctttcatcagttttagagagggagacacccaggctgcatatcagagtcctggacagagcccatttacacat
ttctcatacttgtactgacagtgcacctggaagacagtagatgatggatctgttatgaggcccatcaccaaggtgggaacactg
atgcagttccatgctcctgggttccagctgccaagccttgagtacactgcctttatttatcatctccataaaacattggcaaacacaa
caccagtattcagagatcttaatcttcatgttttgcctcagttcaccacaacccatgacatgttccaccaataactagaactgaggttt
ccaggcctcccaacagagtgatggaaaggaggtggaaatgtgaatgacactgagttgatctgtgaccatttctacaacacacag
attccaatagcacactacaccccactaccatgtacagtgttccgtgttcaggaacagttttaaactaaagcagtgaatgaataagg
gaacaaatcatagttaaccttaaacaaatccacttatagtctttcatctgtttaaaagtgggtggcaggcattaggacaaaattggct
aagtccccgctagggacacccatgttcccatcagattgttgcttgagcccatcctcacagtttccaatactttttcctgataatacatc
ttgggaaactgtagatgacgctacaagtgaatgagaccctaccaccgatgtgggacacacagttttctgctccaggttttagaaag
tctaactcctagatgtctcaacattcatgtttctctcactccttctctctctgtcgctgtttcaatgtcattagaatagttaataatgaacca
atggttatttaaaaatgaaggacatgatactgctaacattggatataaagagtacaaacattaaagtgaaatgaggtattgccttca
aatgtttaaaaataataacataaaatttgccttgatctgaatcctatcatagccatcaccccacaccaccaggacacccacatctgc
cctaggcacagtcctgtctgaggcatctgaccccatgcctgctatataggggcagcacatgcaaataggcctccctctacccat
gaaaaccagcccagccctcaccctgcagctctggcacaggagctccagccccaggactcccaggtgtccactcagtgattgca
ctcaacacagacgctcaccccatggagactgggctgtgctagcttctcctggtcgctgtgctcaaaggtaatgatggggaacgc
ggggcactgagtctgggagaggatgtaagtgagagacacagagagtgtcagtgacagtgtcctgaccatgtcgtctgtgtttgc
aggtgtccagtgtgaagtgcagctggtggagtctgggggagtcgtggtacagcctggggggtccctgagactctcctgtgcag
cctctggattcacctttgatgattataccatgcactgggtccgtcaagctccggggaagggtctggagtgggtctctcttattagttg
ggatggtggtagcacatactatgcagactctgtgaagggccgattcaccatctccagagacaacagcaaaaactccctgtatctg
caaatgaacagtctgagaactgaggacacccgccttgtattactgtgcaaaagatgacacagtgaggggccctcaggctgagcc
cagacacaaacctccctgcaggggagtgcggctccaccagagggcgcgcaagacgcactgagcacagattctggtcctgctc
aggcgcagagggagatgaagccctggtttcctgtcagggatttggggtttcctctcctacagttttgagggaagaattctccttttatg
actctgtccttccttgacttcactgacgtagagaagtttgaagtgacaggaagaagtcctaaacggacacattcaggtttgtgaa
cgatgacagtggtcaccaggatcagagatgcaggactatctggggacctcgtgagtgttgtccagtctgactcaggacagcgtt
ccaggacactgccgactataagacaatttggttttccttcaaacccagacagacccgagccagagtcttgatttgctacctcagttt
tataagtcgtcccatcctcctgtcagagcagcctgtgtgctgaactgaaccaaccgtcttatttaaactgtgggtgttctgcattcac
tttctacagactttatacccaatctccatttcccttaatcctggaacagtctgtggtccctgtgtgcacttccagctgatctggttctgc
tccagtgtcatgggacccctgcacctgctgtggttcagggagagcagaaagtgggacacagtggctgtgcactctggggc
tggagtccacatcacggggagctgtgtctgtggctccagcatgatgcccagtgtcctgaggctgaatcacagctgcaggaaga
gccagtccaagagaccatgtgaccagagtccctactcttctctccatgtctatgctgactggcgtcatcaatgtatttcagtctttca

Figure 13c Unit 3 13971bp Seq ID 191 (con't)

tcagttttagagagggagacacccaggctgcatatcagagtcctggacagagcccatttacacaataccacacttgtaactgaca
atgcaccctggaagacagtagatgatggatctgttatgaggccccatcaccaaggtgggaacattgatgcagttccatgcttctg
ggttccagctgccaagccttgagtacactgccttcatttatcatctccataaacattggcaaacacaacaccagtattcagagatca
atcgtcatgattggccatcattgctatttcatattcctaaatgtttgataaataatattgagtatagctctatgaagtacaatgatatgtgt
ggtcaaaatgaatgcatactgagaggaattgtgaagtcagacttgatgacacattcataccacaacacatgttttggtggagttca
cctgtctcctgctcttaagagatttctactcacaatattctcttaacctctgtcaccatgctgtgcagtagatccctcagtgtgtggagc
ctgtggggactgaaactctgaccttgctccagcgtctcctctgttcctccctcgctcagactttggtcttcaccattgtactttctgcctct
gtgagttcagccttttatcccatgtaggtagcatcacatattatgtgtcttcctggcctggatgcttagcagagtgtacttttactgaca
tattatcctaggcacattattctccgggaccatccaagttgtccaaaatcacagaatttcttactctttactgcttataaacttccttttaa
aatataactttgtccatttctttcataatccattcttgcttccatgagatgtcactggatcatatgtgtgaactcttttgaatgacggtgctt
taaatgaacaaggaactgcagaggtgtttgccacagtgactgtagatcccgtggacacctccctgggatttcatattcattgtacca
tgcaatggtgcttgaagatcatgtaataattctgtttctagtttttgatgcttttccataatggttttactaattaacctgacacagacttgt
accagggttatcatctctctacctccataaaacatgtcagctctggtatgtctgataataggcattctaacaggagggatgggat
gtctcattgtgcttctaacatggacatacatgatggtcctagatttgtagcattttatatgtttgtctttatatcttcttttgaaatttatagat
gtaacataaattttaaaattttatcattttattggccagcgcatggctcactaggctaatcctccacctgcggcaactgcactccgggtt
ctagtctcggtcgggcgctggattctgtcctggttgcccctcttccagtccagctctctactgtggcccaggagcgcagtggagg
atgatccaagtgcttgggccctgcacccgcttggagaccaggagaagcacctggctcctggctacggatcagcgcggtgcag
cggctacagcggccattggagggtgaaccaacggtaaaggaagacattgctctctgtctctctcactgccactgtccactctgcc
catcaaaaaaatttatcattttatttaaaaatttgtctgtatgtatttgtccaaaaccacagagagactgagactgacagtgatctccta
actcctgggttacttctcgatggatacaaaattcagctaggtcaagcgacatccagttgcttggaattctgtccagggctccacgtg
ggactacttggaacttcacctacggcctcccagaggggcttaggcaggcatctgaaaccggaaccatactaggacacagcact
aagcatcctgacacgggaggcaggaatccctcaggctcactccagtgctgctcctgtctccaccttatcatcactgcatttaagga
attgattcagttgcttgagatctttcaacattgggaaataggctcctaatcatatgtataatcaatcttcaatttactttaagtatctatttat
tttatttttaagacagtgttatagcaagagaggaagagaccaacagatggagggagaattccatccactggttaacttcctgaatgg
ctgcaaaggctagggatggctgagcctaaagtcatgagcttggaacttccaccagtttcccacagggaggaaggggacaaacc
cctggttcatggtagacagtgatcaccattgctcttcttatctctgtgagttcaacttgtggagttcaacttgtgcatgtataactaatgt
cacatactatgtgtccacatctacctggattatttctgttagcatattatgctccaggctgacccacgtttcctaatgacagaacaacc
tccttcttaatactgaataatattctatgtccaaatgtgaaataatccattcactgtttaatgcacacttgatttattgtagactgaactatt
atgaacaaaactgcattacctgaacccaggactgcgggtgaattgtgacacagtgacttctacccagtgcttgagctgaactcag
agccatgattacagaatagagaagacagtggaacacaggggtggctgataccagggcacaaaacaccaccaaaggcaggaat
aattctgcccacaccacagtgggctgactcagttcaccacaacccacgacaggttccacaaataactagaactgaggcctccag
acctccaaacacagagtgatggaaaggaggtggaaatgtgcctgacactgagttcatctgtgcccatttctgcatgcacattccaa
tagcacacaaaccccactaccatgtacagtgttctgtgttcaggaacagttttaaacagttttaaacagttttaaatttttaaggcaatg
atgaataaggaaacaaaacatagttatcctaaagatatccacttgcagtccttcatctgtttaaaagtgggcgacagccattaggac
aaaattggctaagtcaccactagggtcacccgtgttcccatcagagaactgactaagcccagcctcacggcttcccacacttttcc
ctcataatgcatcatgggaaactgcaggtgacactaagagcaaatgaggccctaccactgacattggaattacagtcacatttctt
gctccagggttcagaaagactaactcctaggggtcataggcatttgggatgtctggggctgtcaacccaaaggcagaaatctcc
ctttgtcaccttttctgtccatctctacatttctgtatctctcacccctctctctctatcactgtcccaatgtctttcatatagatgataagg
aactaatggttatttaaataaatgaaggacatggtattgctaatactcgatatgaagggcacacacatattaaaatgaaacaaagtat
tttcctttaactttttaaaataatgataacataaaaattcatatgatctgaatcttatcacagccatcaccgtacacccccaggtcacca
catctgccctgggccctgtcctgtctgaggcgtctgaccccatgcctgctatataggggcagcacatgcaaatagggcctccctc
tgcccatgaaaaccagcccagccctcaccctgcagctctggcacaggagctccagccccaggactcccaggtgtccactcagt
gatcgcactcaacacagacactcaccatggagactgggctgcgctggcttctcctggtcgctgtgctcaaaggtaatgatggag
aacgcggggcactgagtctgggagaggatgtgagtgagagacacagagagtgtgagtgacagtgtcctgaccatgtcgtctgt

Figure 13c Unit 3 13971bp Seq ID 191 (con't)

gtttgcaggtgtccagtgtgaggtgcagctggtggagtctgggggaggcttggtacagcctggggggtccctgagactctcctg
tgcagcctctggattcaccttcagtagctatagcatgaactgggtccgccaggctccagggaaggggctggagtgggtttcatac
attagtagtagtagtaccatatactacgcagactctgtgaagggccgattcaccatctccagagacaatgccaagaactcact
gtatctgcaaatgaacagcctgagagccgaggacacggctgtgtattactgtgcgagagacacagtgaggggccctcaggctg
agcccagacacaaacctccctgcaggggagtgcggctccaccaggggggcgcgcaagacacactgagtccagattctggtcct
gctcaggcacagagggagatgaagccctggtttcctgtcagggatttgggtttcctctcctacagttttgagggaagacttctactt
caggattctgtcccttacactgacgccactgacgtagagaagctttatgtgacaggaagaagtcttaaatggacacattcaggtttg
tgaacgatgacagtggtcaccagggtcagagatgtgagacaatcaggggacctcgtgagtgttgtccagtctgactcaggaca
gcgttccaggacactgccgactataagacaattttagttttccttcaaacccagacagacccgagccagagtcttgatttgctacct
cagttttataagtcgtcccatcctcctgtcagagcagcctgtgtgctgcactgaaccaaccgtcttatttttaactgtgggtgttctgca
ttcactttctacagactttataccccaatctccatttccctttaatcctgaaacagtctgtggtccctgtgtgcacttccagctgatctggtt
ctgctccagtgtcgtgggaaccccctgcacctgctgtggttcagggagagcagaaagtgggacacagagcggctgtgcactctg
gggctggagtccacatcacggggagctgtgtctgtggctccagcatgatgcccagtgtcctgaggctgaatcacagctgcagg
aagagccagtcccagagaccatgtgtccagagtccctgctcttcactccatgtctatgctgactggggtcatcaatccatttgtgttc
tttcatcagtattagagagggagacacccaggctgcatatcacattgctggatggagcccatttgcacgctttcccatacttgtact
gacagtgcaccctggaagacagtacatgatggatctgtatgaggccccatcaccaaggtgggaacactgatgcagtttcatgct
cctgggttccagctgacaagcttgagtccactgcctttatttatcatctccataaaacatggccaacacaacaccagtattcaaagat
caatcgtcatgattggccatcgttgctatttcatattcctaaatgtttgataaataatattgagtatagctctatgaggtacaatgatatgt
gtggacaaaatgaatgcatattgagtggaattatgaagtcaggcttgatgacacattcataccacaacacatgttttggtggagttc
acctgtctcctgctcttaagagatttccactcacaatattctcttaacctctgtcaccatgctgtgcagtagatccctcagtgtgtgga
gcctgtgggactaaaactctgaccttgctccagcgtctcctctgttcctccctcgctcagactttggtcttcaccattgtacttcctgc
ctctgtgccttcagcctttatcccatgtaggtagcatcacatattatgtgtcttcctggcctggatgcttagcagagtgtacttttactg
acatattatcttaggcacattattctccgggatcatccaagttgtccaaaatcacagaatttcttactctgtactgcttttaaacttcctttt
aaaatgtaactttgtccatttctttcattttccattcttgcttccatgagatgtcactggatcatatgtgtgaactcttttgaatggcggtgc
tttaaatgaacaaggaactgcagaggtgtttgccacagtgactgcagatcccgtggacacctccctgggatttcatattcattgtac
catgcaatggtgcttgaagatcatgtaataattctgtttctagttttgatgcttttccataatggttttactaattaacctgacacagactt
gtaccagggttatcatctctctctacctccataaaacatgtcagctctggtatgtctgataatagtcattctaacaggagggatggga
tgtctcattgtgcttctaacatggacatacatgatggtcctagatttgtagcattttatatgtttgtctttatatcttcttttgaaatttatagat
gtaacataaattttaaaatttatcattttattggccagcgcatggctcactaggctaatcctccacctgcggtgacttaccgttcgtata
gcatacattatacgaagttatggccggccacgcgt

Figure 13d Unit 4 15445bp Seq ID 192 gcgcgccgcgatcgcgaagttcctattccgaagttcctattctctagaaagtataggaacttcagggcgcgaggctcttctaggg
ggcgcacaagacgcactgagcccagattcctgtcctgcacaggcgcagagggagatgaagccctggtttcctatcagggaatt
ggggtttgctgtcctgtaacagttttgagggaagaattctactttttgattctgtccctcccaacttcaatgacggagagaaagtttga
tgtaaaaagaagaagtcctaattgaacaatttggttcatggacagcgactgtgctcaccagggtcagagatgtgggaatattgag
gacactattgagtctcttccaacctgactcccgacagcaccctcagggcactgaaagctttggacagtttcagttttccctgtataac
cagggacagccgagacagggtcgttgatctgttaaacagcaactattccactcatccctctcctgccacaaccagcaagtgtgca
ctgaaccaacttttgactctacatgtgtgcgatccacactcactttctgcagactttaacccgacctgcatttccctttaatcctggaac
agtctgtggtccctgtgtgaacgtcacagcactcaggaatgtacttgcagctcagctgtgtctcgggctgagcttctgcaggcacc
tgggaagcctacagggacttcctcatcctctaggtcctgggaccctcctgtgggctccctgcctgaactcaagagagaaatgtgc
tggacatcagcagtcaaggtcataactgaatggaaagtgttggatgtgcacttccagctgatctggttctgctccagtgccatggg
acccccctgcacctgctgtggttcagggagagcagaaagtgggacacacagtggctgtgcactctggagctggagtccacatca
cggggagctgtgtctgtggctccagcatgatgaccaatgtcctgaggttgaatcacagctgcaggaagagccagtcttagacca
tgtgtccagagtccctgctcttcactccatgtcatgttgactggagttatcactccactttagtctttcatctatttagagagggagaca
tccatgctgcacatcacattgctggatggagcccatttacacatttcccatacttgtactgacagtgcaccctggaagacagtagat
gatggatctgttatgaggccccatcaccaaggtgggaacactgatgcagttccaagctcctgggttccagctgccaagccttgag
tacactgccttgtttatcatctccataaaacattggccaacacaacaccagtattcagagatctgaatcttcatgattgatcatcgttg
ccatttcatatttataaatgtttcataaataagaattcattatagctctatgaggtacaatgatatgtgtggacaaaatgaatgcatattg
agtggaattatgaactcagacttgctgacacgttcatacctcaacacatgtttttggtggagttcagctgtctcctgctcttaggagat
ttccaaacacagtattctcttaacctctttcaccatgctgtagagtagatccctcagtgtgtggatcctgtgggactggaactctgac
cttgctccaccattctctgctcctccctcactcagactttggtcttcaccattgtacttcctgcctctgtgagttcagcctttatcccgc
ataggtagcatcacatattatgtgtcttcctggcctggatggttagcagtgtgcacttttactgacatattatcctaggcacattattctc
caggatcatccaagttgtccaaaattacagaatttcttactctactgcttataaacttccttttaaaatgtaacttttttccatttctttcatttt
ccattcttgctttcatgagatgtcactggatcacacgtatgaactctttttgattgatggtgctttaaacgaacaaggaactgcagaggt
gtttgccacactgactgcagatcccgtggacacctccctgggatttcatattcattgtaccatgcaatggtgcttgaacatcatgtaa
taattctatttctagttttttgatgcttttccatacggttttactaattaacctgacacagacttgtaccagggttatcatctctctttacctata
aaacatgtcagctctggtatgtctggtaatagccattctaacaggagcgatgggatgtctcattgtgcttctaacatggacatacatg
atggtcccagactgataacattttatttgtctgtctatatatcttctttttaataatttatagaaatgatataattttaaaatttatcattttattta
aaaatttgtctgtatgtatttgtccaaaaccacaaagagacggagactgacagtgatcttctaattcctgggtcacttccccaatggc
tacaaaagctttagctggatgaggcaacagcctggttcttggaattctgtccatgtgtccgcatgggactacttggaacctcaccta
tggcctcccagggtgtgcttaggcaggaatctggaactggaaccaaactaggacgcagcactaagaatcctgacacgggagg
caggaatccctcaggctcactccagtgctgctcctgtcaccacctatcagtcactgcatttaaacaattgatttcttcccttgggatt
cagttgcttgagatcattcaacattaagaaacaggctccaatcatatgtataattaatcttcaatttatttaagtatctattattttatttt
aaagtcagtgttatagcaagagaggaagagaccaacagatggagggagaatcttccttccacaggtttccgtctgaatggctgct
aagactgaagatggctcagccagaaaccaggagcctggaacttcctccagtttcctacagggttggaaggggacaaacacttg
ggtcatggtagacagtgatcaacattgcactgcctacctctgtgagttcaatcttgtggactgcatatataactaatgtcacatactat
gtgtctacgtgtaccgggattatttctgttagcatattgtgttccaggcagacccacgtttcctattgacagaatgacctccttcttaat
actgaataatattctatgtccaaatgcgaaagaatccattcagtcttctatgcacacttgctttattgtagactgaactattgggaacaa
agctgcattacctgaacacaggatggcggctcaattgtgacacagagacttctacccagtgcttgacctcaactcagagtcatgat
tactagacacagagaagagagggggaacagggggaaggctgataccaggacacaaagcaccactcacaggaaggaataattct
gcccacaccgcagtgggctgactcagttcaccacaacacacgacaggttccacaaataatgagaactgaggtctccaggctgc
ccaactcagagtgattgaaaggaggtggaaatgcgcatgacactgagttgatctgtgcccatttctaccatgcacattccagtagc
actctataccccactaccatgtacagtgttctgagttcaggaacagttttaaacagtttaaatagttgttaaactttaaagcaatggag
gaagaaggaaacaaaacatagttaaccttaaaaaatccacttgcagtccttcatctgtttaaaagtgggcgacaggcatttggtca
aaattggctaagtccccactagggacacccgtgttcccatcacagaactgactgagcccagcctcacggcttcccacacttttcct

Figure 13d Unit 4 15445bp Seq ID 192 (con't)

cataatgcatcatgggaaactgtagatgacgctacgagcaaaggagccectaccaccaacgtttgaattacagacacagtttctt
gctccagggttcagaaagactaactcctaggggtcataggcatttgggatgtctggggctgtcaacccaaaggcagaaatctcc
cattgtcaccttttctgtccatctctacatttctgtatctctgaccccttctctctctatcactgtaccaaggtctttcatatagatgaaaag
gaactaatggttatttaaataaatgagggacatgatattgctaacattggatatgaggggtacacacatattaaaatgaaacaaggt
cattgccttcagtctttaaaattatgataacataaacattcatatcatctgaatcgtatcatagccatcaccctacacacccaggaca
ccacgtctgccctgggccctgtcctgtctgaggcgtctgacatcatgcctgctatataggggcagcacatgcagatagggcctcc
ctctgcccatgaaaacctgcccagccctcaccctgcagctctggcacaggagctccagcccagcactccaggtgtccactc
agtgattgcactcaacacagatgctcaccatggagactgggctgcgctggcttctcctggtcgctgtgctcaaaggtaatgatgg
ggaaggcggggcactgagtctgggagaggacgtgagtgagagacacagtgagtgtcagtgacagtgtgctgaccatgtcgtc
tgtgtttgcaggtgtccagtgtgaagtgcagctggtggagtctgggggaggcttggtacagcctggcaggtccctgagactctcc
tgtgcagcctctggattcacctttgatgattatgccatgcactgggtccggcaagctccagggaagggcctggagtgggtctcag
gtattagttggaatagtggtagcataggctatgcggactctgtgaagggccgattcaccatctccagagacaacgccaagaactc
cctgtatctgcaaatgaacagtctgagagctgaggacacggccttgtattactgtgcaaaagatgacacagtgaggggccctca
ggctgagcccagacacaagcctccctgcagggacgcgcggctccaccaggggggcgcaaaagtctcactgagcgcagattct
ggttctgcacaggcacagagggagatgaagccctggtttcctgtagggatggggtttcctctcctgcaacagttttgagggaaga
attcttcttttatgattctgtccctgctactgaattcctgacatagagaagtttgaattgacaggagaagtcctatatgaaccaattcag
gttcagtggtctccaggatcagagatgtgggtctatctgggtacaacgtgagtgttgtccactctgagtcaggacaacgctctcag
ggcactgccgactttaggacaattttagatttcccttcgaccaggacagctgaggcagggttcttggtctttataaatcagctattta
agtatctgtagcctgacaaaaagagcaagtgtgctgaactgaaccaacctttgactttacttgtgggtgatccacacaaactttcga
tagactttatgctcgatttctatttcccttttaatcctggaacagtctgtggtccctgtgtgaacgtcacagcactcaggaatgtacttgc
agctcagctatgtctcaggctgagcttctgcaggcacctgggaagcctacagggacttcctcatcctctaggtcctgggaccctc
ctgtgggctccctgcatgaactcaggagggaaatgccctggacatcagcagtcaaggtcatcactgaatggaaagtgttgggtg
tgcacttccagctgatctggttctgtctagtgtcgtgggaaccccctgcacctgctgtggttcagggagagcagaaagtgggacac
acagtggctgtgcactctggggctggagtccacatcacggggagctgtgtctgtggctccagcatgatgaccaatatgctgagg
ctgaaccacagctgcaggaagagccagtcccagagaccatttgtccagagtccctgctcttcactccatgtctatgctgactggc
gtcatcaatccatttggagtcttagatcagtttagatgggagacaccaggctgcatatcagagtcttggacagagcccatttaca
catttaccacacttgtaactgacaatgcaccctggaagacagtagatgatggatctgttatgaggccccatctccaaggtgggaac
actgatgcagttccaagctcctgggttccagctgccaagcctgagtcaactgccttcatttatcatctccataatactttggcaaaca
caacaccagtattcagagatctgaatcttcatgatgggccattgttgccatttcatattcataaatattttataaataagaattgagtata
cctctatgaggtacaatgatatgtgtggacaaatgaatgcatattgagtggaattatgaagtcagacttgatgacacattcataccg
caacacatgtttttggtggagttcagctgtctcctgcttttaggattttccactcacaatattcccttaagctctgtcaccatgctgtgca
ggagatccctcagtgtgtggatcctgtgggactgaaactctgaccttggtccaccatcacctctgttcctccctcactcagactctg
gtcttcaccactgtacttcctgcctctgtgccttcagctttttttcccacataggtagtatcacatattatgtgtcttcctggcctggatgg
tgagcagagtgtactttactgacatattatcctaggcacattatctccaggatcattaaagttgtccaaaattacagaatttcttactc
tactgcttataaacttccttttaaaatgtaactttgtccatttctttcatttttccattcttttcttccatgagatgtcactggatcatatgtgtact
cttttaaatgaacaaggaactgcagaggtgtttgccactgtgactgcagatcccgtgaacacctccctgggatttcatattcattgta
ccatgcaatggtgcttgaacatcatgtaataattctatttctagttttttgatgcttttccatacggttttactaattaacctgacacagactt
gtaccagggttatcatctctctacctccataaaacatgtcagctctggtatgtctggtaatagccattcaacaggagcgatggga
tgtctcgttgtgcttctaacatggacatacatgatggtcccaaattgatagcattttatatgtctgtctatatatcttcttttaataatttata
gaaatgatataattttaaaatttatcattttatttcagaccttgtctttatgtatttgtccaaaaccacagagagtgagactgacagtgatc
ttctaattcctgggtcacttccccaatggctacaaaagcttcagctggatgaggcaacagcctggtgcttggaattctgtccatgtgt
ccgcatgggagtacttggaacctcacctacggcctcccagggtgtgcttagcaggaatctgaaactggaaccaaactaggaca
cagcactaagcatcctcacatgggaggcaggaatcccacaggctcactcaagtgctgctcctgtcaccaccttatcatcgctgtat
gtacacaattgatttcttcccttgggattcagttgtctgtgttcattcaacattaacaaacaggctcctaatcatatgtataattaatcttc

Figure 13d Unit 4 15445bp Seq ID 192 (con't)

aatgtattttaagtatctatttattttattttaaagacagtgttatagcaacagaggaagagaccaacagatggagggagaattccttc
catttgttcacttcctgaatggctgccaaaggctggggatggctaagcctaaagtcaggagcctggaacttcctctagtttcccaca
gggctggaaggggacaaacatggttgacagtgatcaccattgcacttcctacctctgtgagttcaacttgtggactgcatatataa
ctaatgtcacttactatgtgtccacatgtacttgcattatttcttttagtttgtatgctccagggagacccacatttcctaatgacagaac
aacctccttcttaatactgaataatattccatgtccaaatgggaaagaatgcattcactgttttatgcgcacttgctttgtttgagactga
agtattgtgaacaaagctgcaacctgacacaggactgggggtaaattgtgacacagtgacttctacccagtgcttgagctgaact
cagagtcatggttactagacacagggaagaggggggcaacaggggacggctgataccaggacacaaagcaccactcacagg
aaggaataattctgcccacaccacagtgggctgactcagttcaccacaacacacgacagattccacaaataactagaactaatgc
gtccaggctgcccaactcagagtgattgaaaggaggtagaaatgtgcatgacactgagttgatctgtgcccatttctaccatgcac
attccaatagcactctataccccactaccatgtacagtgttctgtgttcaaaacagttttaaaccatttaaacagtttttaaactttaagg
caatggatgaataaggaaacaaaacatagttaaccttaaaaaatgcacttgcagtccttcatctgtttaaaagtgggtgacaggcat
taggagaaaattggctaagtccccactagggacaccggagttcccgtcagagaactgactgagcccagcctcacggcttccca
cactttttccctcataatgcatcatgccaaactagatgacactacaagaaaatgagcacctaccactgacgttggaattacagacata
gtttcttgcttcagcgttcagaaagactaactcctagatgtcataggcatttgggatgtctggggctgtcaacccaaaggcagaaat
ctcccattgtcacctttctgtccatctctacatttctgtatctctgaccccttctctctctatcactgtcccaatgtctttcatatagatgat
aaggaactagtggttacttaaataaatgagggacatgatattgctaacactggatatgagggtaaacacatattaaaatgaaacaa
ggtcattgccttcaactttttgaaattatgataacataaaaattcatatgatctgaatcatatattatagtcatcaccctacaaacccaggtc
acctaattctgccccaggccctatcctgtctgaggcatctgaccccagggctgctatataggggcagcacatgcagatagccctc
cctctgcccatgaaaaccagcccagccctcaccctgcagctctggcacaggagctccagccccaggactcccaggtgtccact
agtgatcacactcaacacagacgctcaccatggagactgggctgcgctggcttctcctggtcgctgtgctcaaaggtaatgatgg
ggaacgcggggcactgagtctgggagaggacgtgagtgagagacacagagagtgtgagtgacagtgtcgtgaccatgtcgtc
tgtgtttgcaggtgtccagtgtcaggtgcagctggtggagtctgggggaggcgtggtccagcctggggaggtccctgagactctc
ctgtgcagcctctggattcaccttcagtagctatggcatgcactgggtccgccaggctccaggcaaggggctggagtgggtggc
agttatatcatatgatggaagtaataaatactatgcagactccgtgaagggccgattcaccatctccagagacaattccaagaaca
cgctgtatctgcaaatgaacagcctgagagctgaggacacggctgtgtattactgtgcgagagacacagtgaggggccctcag
gctgagcccagacacaaacctccctgcagggccgtacgtctccaccaggaggcacacaagatgcactgaatatatattctggtc
atgggtaggtgtagagggacaataagccctggtttccttttagggaattgggttcctctcctctaatacatttgaagaaatggttct
actcttacgattctgtccctgccactgacttcactgacggatagaaactttgaatagaaggaagaagtcctacgtgacaatttcggg
ttcatgactgacaactatcctcaccgcgatcagatatcatggggatctgtgaggacctcgtgagtcttttccagtctaactcgtgctg
gtgtcctcagggcgctgccgactctaggacaattttacttttcccttatatcctggagacaactgagccagggtctctggtctgtta
aacctcaactatttccctctcttcctgtcaaagtagcctgtgtgcggaactgaattgacattttattttaaactgtgggtgatccacact
cactttctgcagaatgtggccacctttaatcctggaacagtctgtggtccctgtgtgaacgtcacagcactcaggaatgtacttgca
gctcagctgtgtctcagactgagcttctggaagcacctgggaagcctacagggacttcctcatcctctaggtcttgggacactcct
gggggggctccctgcctgaactcggaggggaaatgcactggacatcagcagtcaaggtcatcactgaatggaaagtgttgggtg
tgcacttctagttgatctgattctgttgagtgttgtgggactccctgcacctgctgtggttcagggagagcagaaagtgggacacac
agtggctgtgcactctggggctggagtccacatcacggggagctgtgtctgtggctccagcatgatgaccagtgtcctgacgct
gaatcacagcttcaggaagagcaagtctcggagaccatgtgtccagagtccctgctcttcactccatgtctatggtgactggggtc
atcaatgcatttggagacttccatcagtattagagagggagacacccaggctgcatatcagagtgctggacacagcccatttgca
cactttcccagacaagtaactgacagtgcaccctggaagtcagtagatgatggatgtgttatgaggccccatcacgaaggtggg
aacactaatgcagtttcaagctcctgggttccagctgccaagcttcagtccactggaatttatttatcatctccataaaatattggaaa
atactggaaagcactacaccagtattcagagtgttgaatctccatttttgatcatttaatcatttcctttacataagtgtttgatatataata
ccaaaacatagacatatgaggtacaatgatatgtgttgataaatatgtatcaaattgagttttttatgaagtcagacttattgacatg
ctcatcagaaaaccacatgtttccatggtagaatgtcagttgtctgctgttttggaattctttaggcacaatattcccttcactgctgtg
accatgctgtacagtagatcctcagtgtatggatcctgttggactggaactctgaccttgctccaacgtctcctctgctcctcccttg

Figure 13d Unit 4 15445bp Seq ID 192 (con't)

ctcagacgttggtcttcaccatcgtacttcctgcctctgtgacttcatccttttatcccatgtatccagcatcacgtattatttgtcttcttg
tcctgcatggttagcagagtgtacttaccctgacacattatccttggacattattctccaggatcatccgagttgtccaaaatacaga
atttcctcatctgtactgccatataaacttcctgttaaatataattttgtccatttgttccattgttgattctttcttcatgaatatttcactgga
ttgtatgtgtgaactcttgtgaatgatgctgcattagttgaacatggaagagcagaggtgtttgccacattgattgcggttcccctgg
acacctccctgggatttcatattccttctactcaaaattggtgtttgaagatcctgtgataattctgtttcagttttgatgaatttccataat
aattttacttgtttacctgactccattcttgcaccagagttatctccagcttcctccacatggattgtcagctctggattgtaggataata
ctcattctaacaggaaggatgggatgtctcattgtgcatctattagggacatgcatgatgggcccaatatatcattttatatgttgcctt
tatatctttttaaaaagttaaagatactatttcacttattttgatatttgtatttacatattttttttcaaaaaagcaaagagactgagactga
cagtgatcttctaattcctggtcacttcccagatggatacaaaagcttcagctgggttaggtgacagccatgtgcttggaattctgtc
cagttgtccacatggcagtacttggaacttcacctactgcctcccagaagggcttagacaggaatctgacactggaacgaaacta
ggacacagcactcagcatcctgacacgggaggcaggaatccctcaggctcactccagtgctgctcctgtcaccaccttatcatc
actgcatttaaggaattgattgcttcccttgggatcagtggcttgagttcattcaacatttggaaataggctcctaaccatatgtataat
taatctttcatttattttaagtatttattttatttgaaaggcagtgttatagcaagagagaaagctatcaacagatggagagagaagtttc
tattcactggttcacttcgtgaatggctgcaaaggctgggatggctgagcctgaagccaggagcctggaacttcccccagtttcc
cccagagctggaaggggacaaacacttgggtcatggtacacagtgatcaccattgcacttcctccctctgtgagttcaatcttgtg
gactgcatgtataactaatgtcacatactatgtgtccacatgtacctgcattatttctgttagcatattatgctccaggctgaccaatga
tttcctaacgaccgaacaacctccttcttaacactgaataatattccatgtcaaatgtaacagactgcattcactgttttaggcacattt
cactttattgtagactgaactattgtgaacaaagctgcattacatgaacccaggactgtgggtgaattgtgacacagtgacttctatc
cagtgcttgagctgaactcagagtcatggttactagacacagggaagaggggggaacacagggcagctgataccagggcacaa
agcactcacaggaaggaataattctgcccacactacagtgggctgactcagttcaccacaacccatgacagattccatgaataat
gagaactgaggcctccaggcccctccaactcagagtgtaggaaaggaggtggaaatgtgaatgacattcagttgatctgtgccc
atttctacaacacacagattccaatagcacagtacaccccactagcaagcacagtgttctgtgttcatgacgagtgttaaataagtc
aatggatgaataaggaaacaaaacatagttaacctaaaaagaatccacttgcagtcttttatctgtttaaaagtgggaggcaggcat
taggacaaaattggcaaagtccccactagggacaccggtgttcccatcagaatgaatcattcagccacacgactcccacactt
ttctgataatgcatttggaaaactgtagatgacactacaagtgaatgagcccctaccactgacgtgggaaacaaatttgcagttttg
cgctccatgttttagaaaggctaagtcctcggtgttgtaggcacttgggatgtttggggctgtcaatcaaaggtggaaatctccctt
gtcaccttttctgtccatctctacatttctctttctctcacccctctctcactgtcactattccaatgttattcaaatagttaaaaatgaacc
atggttatttttaaaaatgaaggacatgataacactggattattaaggatacacacatattaaaatgaaacaaggtcattgccttcaatt
gtttaagcaacaatgataatgtaaagatttctatgatctgaatcctatcatagccatcaacctacaccacaggacaccacatctgcc
ctgggcactttcctgtctgaggcatcagaccccatgcctgctatataggggcagcacatgaaaacagggcctccctctgcccatg
aaaaccagcacaggcctcaccctgcagctctggcacaggagctccagcctcaggactcccaggtgtccactcagtgatcacac
tcaacacagatgctcaccatggagactgggctgcgctggcttctcctggtcgctgtgctcaaaggtaatgatggggaacgcggg
gcactgagtctgggagaggacgtgagtgagagacacagagagtgtgcgtgacagtgtgctgaccatgtcgtctgtgtttgcagg
tgtccagtgaggtgcagctggtggagtctggggggaggcttagttcagcctggggggtccctgagactctcctgtgcagcctctg
gattcaccttcagtagctactggatgcactgggtccgccaagctccagggaaggggctggtgtgggtctcacgtattaatagtga
tgggagtagcacaagctacgcggactccgtgaagggccgattcaccatctccagagacaacgccaagaacacgctgtatctgc
aaatgaacagtctgagagccgaggacacggctgtgtattactgtgcaagagacacagtgaggggccctcaggctgagcccag
acacaaacctccctgcaggggagtgcggctccaccagggtgcgcacaagacgcactgagcccagattctggccctgctctgat
gcagagggaaatgagccctggtttcctgtcagtgatttgtggtttgttctacagttttgcggcaagaattctacttcatgattctgtctg
ttccactgacttcactgacttagagaagtttgatgtgacaggaagaagtcctgaatggacacattcaggttagtgaactatgacagt
ggtcaccagggtcagagatgtgagacaatcaggggacctcgtgagtgttgtccagtctgactcaggacagcgttccaggacact
gccgactataagacaattttagttttccttcaaacccagagagagccgagtcagagcattgattttcaccttaattatataagtcatg
acacatcctgtcggagtagcctgtgtgctgcactgaaccaactgtcttattttaaactgtgggtgttctgcattcactttctacagactt

Figure 13d Unit 4 15445bp Seq ID 192 (con't)

0tataccccatctccatttccctttcatcctggaacagtctgtggtccctgtgtgaacgtcacagcactcaggaatgtactgcagctc
agttgtgtctcaggctgagcttctgcaggcacctgtaccgttcgtatagcatacattatacgaagttatggccggccacgcgt

HUMANIZED IMMUNOGLOBULIN LOCI

CROSS REFERENCE TO RELATED APPLICATIONS

This application is a divisional application of U.S. application Ser. No. 12/511,188 filed Jul. 29, 2009, which is a divisional application of U.S. application Ser. No. 10/893,483 filed Jul. 15, 2004 (now U.S. Pat. No. 7,585,668) which claims priority under 35 U.S.C. Section 119(e) and the benefit of U.S. Provisional Application Ser. No. 60/487,733 filed Jul. 15, 2003, the entire disclosures of which are incorporated herein by reference in their entireties.

In accordance with 37 CFR 1.821(e), we hereby expressly incorporate herein by reference, in its entirety, the last-filed (filed Apr. 4, 2005) computer readable Sequence Listing, saved as "39691-0007A saved Apr. 4, 2005.txt" date of creation Apr. 4, 2005, size 1,489 KB, submitted in U.S. application Ser. No. 10/893,483, filed Jul. 15, 2004.

FIELD OF THE INVENTION

The present invention concerns methods and means to produce humanized antibodies from transgenic non-human animals. The invention specifically relates to novel immunoglobulin heavy and light chain constructs, recombination and transgenic vectors useful in making transgenic non-human animals expressing humanized antibodies, transgenic animals, and humanized immunoglobulin preparations. The transgenic vectors contain humanized immunoglobulin loci, which are capable of undergoing gene rearrangement, gene conversion and hypermutation in transgenic non-human animals to produce diversified humanized antibodies, while leaving the endogenous regulatory and antibody production machinery of the non-human animals essentially intact. The humanized antibodies obtained have minimal immunogenicity to humans and are appropriate for use in the therapeutic treatment of human subjects.

BACKGROUND OF THE INVENTION

Antibodies are an important class of pharmaceutical products that have been successfully used in the treatment of various human diseases and conditions, such as cancer, allergic diseases, prevention of transplant rejection and host-versus-graft disease.

A major problem of antibody preparations obtained from animals is the intrinsic immunogenicity of non-human immunoglobulins in human patients. In order to reduce the immunogenicity of non-human antibodies, it has been shown that by fusing animal variable (V) region exons with human constant (C) region exons, a chimeric antibody gene can be obtained.

Humanized monoclonal antibodies have also been developed and are in clinical use. Humanized monoclonal antibodies are typically human antibodies in which some CDR residues and possibly some FR residues are substituted by residues from analogous sites in non-human animal, e.g. rodent, antibodies. Humanization can be essentially performed following the method of Winter and co-workers (Jones et al., *Nature,* 321: 522 (1986); Riechmann et al., *Nature,* 332: 323 (1988); Verhoeyen et al., *Science,* 239: 1534 (1988)), by substituting non-human animal, e.g. rodent, CDRs or CDR sequences for the corresponding sequences of a human monoclonal antibody.

It has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA,* 90: 2551 (1993); Jakobovits et al., *Nature,* 362: 255 (1993); Bruggemann et al., *Year in Immunol.,* 7: 33 (1993). While this genetic engineering approach resulted in the expression of human immunoglobulin polypeptides in genetically engineered mice, the level of human immunoglobulin expression is low. This may be due to species-specific regulatory elements in the immunoglobulin loci that are necessary for efficient expression of immunoglobulins. As demonstrated in transfected cell lines, regulatory elements present in human immunoglobulin genes may not function properly in non-human animals.

Indeed, several regulatory elements in immunoglobulin genes have been described. Of particular importance are enhancers downstream (3') of heavy chain constant regions and intronic enhancers in light chain genes. In addition, other, yet to be identified, control elements may be present in immunoglobulin genes. Studies in mice have shown that the membrane and cytoplasmic tail of the membrane form of immunoglobulin molecules play an important role in expression levels of human-mouse chimeric antibodies in the serum of mice homozygous for the human Cγ1 gene. Therefore, for the expression of heterologous immunoglobulin genes in animals it is desirable to replace sequences that contain enhancer elements and exons encoding transmembrane (M1 exon) and cytoplasmic tail (M2 exon) with sequences that are normally found in the animal in similar positions.

In addition to the issues raised by the potential immunogenicity of the non-human antibodies, the use of monoclonal antibodies in general, whether chimeric, humanized or human, is further limited by the fact that devastating diseases, such as cancer and infections with virulent pathogens, are difficult to treat by attacking one target, due to their complexity, multifactorial etiology and adaptivity. Monoclonal antibodies directed against singularly defined targets fail when those targets change, evolve and mutate. Thus, malignancies may gain resistance to standard monoclonal antibody therapies. A solution to this problem is the use of polyclonal antibodies, which have the ability to target and attack a plurality of evolving targets linked with complex diseases. Polyclonal antibodies also have the ability to neutralize bacterial and viral toxins, and direct immune responses to kill and eliminate pathogens.

Accordingly, there is a great clinical need for a new approach suitable for the large-scale production of high-titer, high-affinity, humanized poly- and monoclonal antibodies.

The introduction of human immunoglobulin genes into the genome of mice resulted in expression of a diversified human antibody repertoire in genetically engineered mice. In both mice and humans, primary antibody diversity is generated by gene rearrangement. This process results in the generation of many different recombined V(D)J segments encoding a large number of antibody molecules with different antigen binding sites. However, in other animals, like rabbits, pigs, cows and birds, primary antibody diversity is generated by substantially different mechanisms, namely templated mutations or gene conversion and non-templated mutations or hypermutation. For example, it is well established that in rabbit and chicken, VDJ rearrangement is very limited (almost 90% of immunoglobulin is generated with the 3' proximal VH1 element) and antibody diversity is generated by gene conversion and hypermutation. In contrast, mouse and human gene conversion occurs very rarely, if at all. Therefore, it is expected that in animals that diversify their primary antibody repertoire by gene conversion and hypermutation a genetic engineering approach based on gene rearrangement will result in animals with low antibody titers and limited antibody diversity. Thus, the genetic engineering of large animals for the production of non-immunogenic antibody preparations for human therapy requires alternative genetic engineering strategies.

The production of humanized antibodies in transgenic non-human animals is described in PCT Publication No. WO 02/12437, published on Feb. 14, 2002, the disclosure of which is hereby expressly incorporated by reference in its entirety. WO 02/12437 describes genetically engineered non-human animals containing one or more humanized immunoglobulin loci which are capable of undergoing gene rearrangement and gene conversion in transgenic non-human animals, including animals in which antibody diversity is primarily generated by gene conversion to produce diversified humanized antibodies. The humanized antibodies obtained have minimal immunogenicity to humans and are appropriate for use in the therapeutic treatment of human subjects. It further describes novel nucleotide sequences from the 5' and 3' flanking regions of immunoglobulin heavy chain constant region segments of various non-human mammalians, such as chickens, cows, sheep, and rabbits. Recombinant vectors in which human immunoglobulin heavy chain gene segments are flanked by sequences homologous to such 5' and 3' sequences are shown to be useful for replacing an immunoglobulin heavy chain gene segment of a non-human animal with the corresponding human immunoglobulin heavy chain gene segment.

SUMMARY OF THE INVENTION

In one aspect, the present invention concerns an isolated nucleic acid molecule comprising a human immunoglobulin gene segment, flanked by nucleotide sequences, wherein the flanking sequences are identical or different, and comprise at least about 20 contiguous nucleotides of a spacer sequence from an immunoglobulin heavy or light chain gene of an animal generating antibody diversity primarily by gene conversion and/or hypermutation, or from a consensus sequence of two or more of the spacer sequences.

In another aspect, the invention concerns an isolated nucleic acid molecule comprising a human immunoglobulin heavy or light chain constant region (C) gene segment, flanked by nucleotide sequences, wherein the flanking sequences are identical or different, and comprise at least about 20 contiguous nucleotides of a spacer sequence from an immunoglobulin heavy or light chain gene of a non-primate animal, or from a consensus sequence of two or more of the spacer sequences.

In a further aspect, the invention concerns an isolated nucleic acid molecule comprising a human immunoglobulin heavy or light chain gene segment, flanked by nucleotide sequences, wherein the flanking sequences are identical or different, and comprise at least about 20 contiguous nucleotides of a spacer sequence selected from the group consisting of SEQ ID NOS: 1 to 185 (Table 1), or from a consensus sequence of two or more of the spacer sequences.

In one embodiment, the flanking sequences comprise at least about 50 contiguous nucleotides of a spacer sequence.

In another embodiment, the human immunoglobulin gene segment is a heavy chain V, D, or J segment, where the V fragment may, for example be a member of the VH3, VH1, VH5, or VH4 family.

In a further embodiment, the human immunoglobulin gene segment is a light chain V or J segment, where the V segment may, for example be a κ light chain gene segment, such as Vκ1, Vκ3, or Vκ4, or a λ light chain segment, e.g. Vλ1, Vλ2 or Vλ3.

In a further embodiment, the non-primate animal which generates antibody diversity primarily by gene conversion and/or somatic hypermutation is, for example, rabbit, pig, bird, e.g. chicken, turkey, duck, or goose, sheep, goat, cow, horse or donkey, however, other non-primate animals, e.g. rodents are also specifically included within the scope of the invention.

In another aspect, the invention concerns a recombination vector comprising any of the foregoing nucleic acid molecules.

In yet another aspect, the invention concerns a transgenic vector comprising a humanized immunoglobulin (Ig) locus, wherein the humanized Ig locus is derived from an Ig locus or a portion of an Ig locus of a non-human animal, comprising multiple Ig segments wherein (a) at least one of the gene segments is a human Ig gene segment flanked by nucleotide sequences comprising at least about 20 contiguous nucleotides from a spacer sequence, or from a consensus sequence or two or more of such spacer sequences;

(b) the gene segments are juxtaposed in an unrearranged, partially rearranged or fully rearranged configuration, and (c) the humanized Ig locus is capable of undergoing gene rearrangement, if necessary, as well as gene conversion and/or hypermutation, if the non-human animal is a gene converting animal, and producing a repertoire of humanized immunoglobulins in the non-human animal.

In a further embodiment, the humanized Ig heavy chain locus present in the transgenic vector comprises about 5 to 100 V gene segments, with at least one human V gene segment. In a specific embodiment, the humanized Ig heavy chain locus comprises more than one human V gene segments.

In another embodiment, the humanized Ig heavy chain locus present in the transgenic vector comprises about 5 to 25 D gene segments, In a specific embodiment, the humanized Ig heavy chain locus comprises one or several human D gene segments.

In yet another embodiment, the humanized Ig heavy chain locus present in the transgenic vector comprises about 1 to 10 J gene segments, with at least one human J gene segment. In a specific embodiment, the humanized Ig heavy chain locus comprises more than one human J gene segments.

In another embodiment, the humanized Ig heavy chain locus present in the transgenic vector comprises about 1-25 C region segments, with at least one human C region segment. In a specific embodiment, the humanized Ig heavy chain locus present in the transgenic vector comprises more than one human C gene segment.

In a still further embodiment, the humanized Ig locus present in the transgenic vector is a light chain locus of a non-human animal, and it comprises at least one V gene segment, at least one J gene segment and at least one constant (C) region gene segment, where at least one gene segment is selected from the group of human light chain V and J segments and human light chain C region segments. In a specific embodiment, the constant region gene segment is a human light chain constant region gene segment, which can, for example, be a Cλ or Cκ gene segment. In another embodiment, the humanized Ig light chain locus comprises two or more segments selected from human V and J segments and human C region segments. In a further embodiment, the humanized Ig light chain locus comprises at least one human V segment, at least one human J segment, and at least one human C region segment.

In a further embodiment, the humanized Ig light chain locus present in the transgenic vector comprises about 5-100 V gene segments, with at least one human V gene segment, wherein the human V gene segment is placed downstream to the 5-100 V gene segments of the non-human animal. In a specific embodiment, the human V gene segment is placed immediately 5' to a J gene segment in a rearranged configuration. In another embodiment, the humanized Ig light chain locus present in the transgenic vector comprises more than one human V gene segment.

In a still further embodiment, the humanized Ig light chain locus present in the transgenic vector comprises about 1-10 J gene segments, with at least one human J gene segment. In a specific embodiment, the humanized Ig light chain locus present in the transgenic vector comprises more than one human J gene segment.

In another embodiment, the humanized Ig light chain locus present in the transgenic vector comprises about 1-25 C region segments, with at least one human C region segment. In a specific embodiment, the humanized Ig light chain locus present in the transgenic vector comprises more than one human C gene segment.

In a still further embodiment, the humanized Ig locus present in the transgenic vector is a light chain locus of a non-human animal, and it comprises at least one V gene segment, at least one J gene segment and at least one constant (C) region gene segment, where at least one gene segment is selected from the group of human light chain V and J segments and human light chain C region segments. In a specific embodiment, the constant region gene segment is a human light chain constant region gene segment, which can, for example, be a Cλ or Cκ gene segment. In another embodiment, the humanized Ig light chain locus comprises two or more segments selected from human V and J segments and human C region segments. In a further embodiment, the humanized Ig light chain locus comprises at least one human V segment, at least one human J segment, and at least one human C region segment.

In a different aspect, the invention concerns a nucleic acid molecule comprising two or more units consisting of, from 5' to 3' direction, a 5' nucleotide sequence, a human immunoglobulin sequence, and a 3' nucleotide sequence, wherein the 5' and 3' nucleotide sequences are identical or different, and comprise at least about 20 contiguous nucleotides from a spacer sequence separating the coding regions in a non-primate animal immunoglobulin heavy or light chain gene, or from a consensus sequence of two or more of the spacer sequences. In a specific embodiment, the spacer sequences are selected from within SEQ ID NOS: 1 to 185 (Table 1). In another particular embodiment, the 5' and/or 3' nucleotide sequences in all repetitive units of the nucleic acid molecule are identical. In another particular embodiment, the repetitive units of the nucleic acid molecule comprise at least two different 5' and/or 3' sequences. In a further embodiment, the 5' and 3' nucleotide sequence are different from each other, but all 5' and all 3' nucleotide sequences are identical.

In a further aspect, the invention concerns a method for making a transgenic vector comprising a humanized immunoglobulin (Ig) locus capable of producing a functional repertoire of humanized antibodies in a non-human animal, comprising:

(a) obtaining a DNA fragment comprising an Ig locus or a portion thereof from the non-human animal which comprises at least one V gene segment, at least one J gene segment and at least one constant region gene segment; and (b) integrating at least one human Ig gene segment into the DNA fragment of step (a) to produce a humanized Ig locus, wherein the human Ig gene segment flanked by nucleotide sequences comprising at least about 20 contiguous nucleotides from a spacer sequence separating the coding regions in a non-primate animal immunoglobulin heavy or light chain gene, or from a consensus sequence or two or more of such spacer sequences; wherein (i) the gene segments are juxtaposed in an unrearranged, partially rearranged or fully rearranged configuration, and (ii) the humanized Ig locus is capable of undergoing gene rearrangement, if necessary, and producing a repertoire of humanized immunoglobulins in the non-human animal.

The humanized Ig locus can be a humanized Ig heavy chain or light chain locus. In the case of a humanized Ig heavy chain locus the DNA fragment obtained in step (a) additionally comprises at least one D gene segment.

In another aspect, the invention concerns a transgenic animal comprising a humanized immunoglobulin locus described above, and methods for making such transgenic animals. In one embodiment, the transgenic animal comprises both a humanized immunoglobulin heavy chain locus and a humanized immunoglobulin light chain locus. In another embodiment, only one of the heavy and light chain loci present in the transgenic animal is humanized. In another embodiment, all of the V, D, J and C regions of at least one of the animal's immunoglobulin loci are humanized. In yet another embodiment, all of the V, D, J, and C region of the transgenic animals endogenous immunoglobulin loci are humanized.

In a further aspect, the invention concerns a B cell from the transgenic animals produced in accordance with the present invention.

In a still further aspect, the invention concerns a humanized immunoglobulin produced using a transgenic animal of the present invention, and an antibody preparation or a pharmaceutical composition comprising the humanized immunoglobulin.

BRIEF DESCRIPTION OF THE DRAWINGS

FIG. 7(a) shows that the upper cassette contains two restriction sites (FseI and AscI) flanking a gentamycin cassette. FIG. 7(b) shows that the lower cassette contains an inverted (i) and mutated (71) loxP-site, a FRT-site and a MluI-restriction site. After modification the BAC is digested with FseI and AscI.

FIGS. 12a to 12c show a humanized light chain locus. A synthetic sequence (FIG. 12a, Unit 1, 12,235 bp, SEQ ID NO: 187) containing 17 human V pseudogenes and 18 chicken spacer sequences is shown in (a). A second synthetic sequence (FIG. 12b, Unit 2, 13,283 bp, SEQ ID NO: 188) containing a functional rearranged human VkJk gene fragment, 11 human V pseudogenes, 12 chicken spacer sequences and 2 introns is shown in (b). Units 1 and 2 were combined with a fragment derived from BAC 179L1 containing human Ck and rabbit intron and spacer sequences (FIG. 12c).

FIG. 13a-e show a humanized heavy chain locus. Four synthetic DNA fragments (Unit 1-4, FIG. 13a-d, SEQ ID NOS: 189, 190, 191, 192) consisting of human VH3 gene fragments and rabbit spacer and intron sequences were combined with parts of BAC 219D23, 27N5 and Fos15B as shown in (FIG. 13e).

DETAILED DESCRIPTION OF THE INVENTION

A. Definitions

Figure 1:
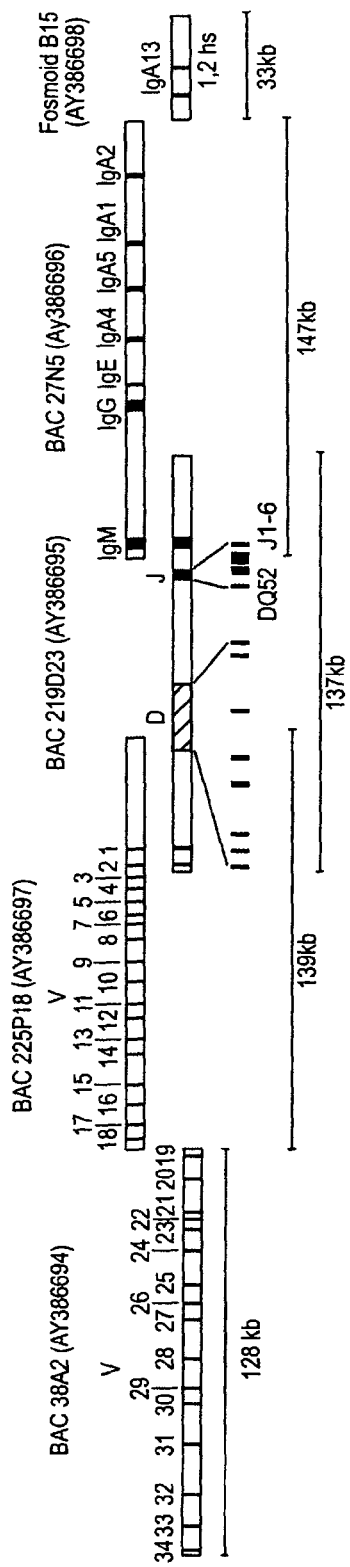
FIG. 1 is a schematic depiction of the rabbit immunoglobulin gene heavy chain locus.

"Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

"Native antibodies and immunoglobulins" are usually heterotetrameric glycoproteins of about 150,000 daltons, composed of two identical light (L) chains and two identical heavy (H) chains. Each light chain is linked to a heavy chain by covalent disulfide bond(s), while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light chain variable domain is aligned with the variable domain of the heavy chain. Particular amino acid residues are believed to form an interface between the light- and heavy-chain variable domains (Clothia et al., *J. Mol. Biol.* 186:651 (1985); Novotny and Haber, *Proc. Natl. Acad. Sci. U.S.A.* 82:4592 (1985)).

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, connected by three CDRs. The CDRs in each chain are held together in close proximity by the FR regions and, with the CDRs from the other chain, contribute to the formation of the antigen-binding site of antibodies (see Kabat et al., *Sequences of Proteins of Immunological Interest*, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity.

The term "monoclonal antibody" is used to refer to an antibody molecule synthesized by a single clone of B cells.

The term "polyclonal antibody" is used to refer to a population of antibody molecules synthesized by many clones of B cells. In a specific embodiment, polyclonal antibodies recognize several epitopes.

The terms "a humanized antibody" and "a humanized immunoglobulin", as used herein, mean an immunoglobulin molecule comprising at least a portion of a human immunoglobulin polypeptide sequence (or a polypeptide sequence encoded by a human immunoglobulin gene segment). The humanized immunoglobulin molecules of the present invention can be isolated from a transgenic non-human animal engineered to produce humanized immunoglobulin molecules. Such humanized immunoglobulin molecules are less immunogenic to primates, especially humans, relative to non-humanized immunoglobulin molecules prepared from the animal or prepared from cells derived from the animal.

The term "non-human animal" as used herein includes, but is not limited to mammals, and includes, for example, non-human primates, rabbits, pigs, birds (e.g., chickens, turkeys, ducks, geese and the like), sheep, goats, cows, horses, and rodents (e.g. mice and rats). Preferred non-human animals are those animals which create antibody diversity substantially by gene conversion and/or somatic hypermutation, e.g., rabbit, pigs, birds (e.g., chicken, turkey, duck, goose and the like), sheep, goat, and cow. Particularly preferred non-human animals are rabbit and chicken.

The term "non-primate animal" as used herein includes, but is not limited to, mammals other than primates, including those listed above.

The phrase "animals which create antibody diversity substantially by gene conversion and/or hypermutation" is used to refer to animals in which the predominant mechanism of antibody diversification is gene conversion and/or hypermutation as opposed to gene rearrangement.

The term "Ig gene segment" as used herein refers to segments of DNA encoding various portions of an Ig molecule, which are present in the germline of animals and humans, and which are brought together in B cells to form rearranged Ig genes. Thus, Ig gene segments as used herein include V gene segments, D gene segments, J gene segments and C region gene segments.

The term "human Ig gene segment" as used herein includes both naturally occurring sequences of a human Ig gene segment, degenerate forms of naturally occurring sequences of a human Ig gene segment, as well as synthetic sequences that encode a polypeptide sequence substantially identical to the polypeptide encoded by a naturally occurring sequence of a human Ig gene segment. By "substantially" is meant that the degree of amino acid sequence identity is at least about 85%-95%. In a particular embodiment, the human Ig gene segment renders the immunoglobulin molecule non-immunogenic in humans.

A specific humanized immunoglobulin molecule of the present invention contains at least a portion of a human heavy or light chain variable region polypeptide sequence. Another specific immunoglobulin molecule contains at least a portion of a human heavy or light chain variable region polypeptide sequence, and at least a portion of a human constant domain polypeptide sequence.

By "a preparation of humanized antibodies" or "a humanized antibody preparation" is meant an isolated antibody product or a purified antibody product prepared from a transgenic non-human animal (e.g., serum, milk, or egg yolk of the animal) or from cells derived from a transgenic non-human animal (e.g., a B-cell or a hybridoma cell).

A humanized antibody preparation can be a preparation of polyclonal antibodies, which includes a repertoire of humanized immunoglobulin molecules. A humanized antibody preparation can also be a preparation of a monoclonal antibody.

The terms "antibody diversity" and "antibody repertoire" are used interchangeably, and refer to the total of all antibody specificities that an organism is capable of expressing.

The term "spacer sequence" is used herein to refer to any non-coding nucleotide sequence present in an immunoglobulin heavy or light chain gene. Thus, the term specifically includes intron sequences and any other non-coding sequences separating the coding regions within the V, D, J segments and C region segments in an immunoglobulin heavy chain gene, intron sequences and any other non-coding sequences separating the coding regions within the V and J segments an C region segments in an immunoglobulin light chain gene, as well as non-coding sequence flanking regulatory elements, such as enhancers, in an immunoglobulin heavy or light chain gene. In addition, non-coding sequences between exons encoding parts of a membrane-spanning helix and heavy and light chain enhancers are specifically included.

An Ig locus having the capacity to undergo gene rearrangement and gene conversion is also referred to herein as a "functional" Ig locus, and the antibodies with a diversity generated by a functional Ig locus are also referred to herein as "functional" antibodies or a "functional" repertoire of antibodies.

B. Relevant Literature

Regulatory elements in immunoglobulin genes have been described by Bradley et al. (1999), *Transcriptional enhancers and the evolution of the IgH locus*; Lauster, R. et al., *Embo J* 12: 4615-23 (1993); Volgina et al., *J Immunol* 165:6400 (2000); Hole et al., *J Immunol* 146:4377 (1991).

Antibody diversification by gene conversion in chicken and rabbit has been described by Bucchini et al., *Nature* 326: 409-11 (1987); Knight et al., *Advances in Immunology* 56: 179-218 (1994); Langman et al., *Res Immunol* 144: 422-46 (1993). The generation of mice expressing human-mouse chimeric antibodies has been described by Pluschke et al., *Journal of Immunological Methods* 215: 27-37 (1998). The generation of mice expressing human-mouse chimeric antibodies with mouse derived membrane and cytoplamic tails has been described by Zou et al., *Science* 262: 1271-1274 (1993); Zou et al. *Curr Biol* 4: 1099-1103. The generation of mice expressing human immunoglobulin polypeptides has been described by Bruggemann et al. *Curr Opin Biotechnol* 8(4): 455-8 (1997); Lonberg et al. *Int Rev Immunol* 13(1):65-93 (1995); Neuberger et al., *Nature* 338: 350-2 (1989). Generation of transgenic mice using a BAC clone has been described by Yang et al., *Nat Biotechnol* 15: 859-65 (1997). The generation of cows expressing human antibodies has been described by Kuroiwa et al., Nature Biotech 20(9): 889-894 (2002).

The generation of transgenic rabbits has been described by Fan, J. et al., Pathol Int 49: 583-94 (1999); Brem et al., *Mol Reprod Dev* 44: 56-62 (1996). Rabbits with impaired immunoglobulin expression have been described by McCartney-Francis et al., *Mol Immunol* 24: 357-64 (1987); Allegrucci, et al., *Eur J Immunol* 21: 411-7 (1991).

The production of transgenic chicken has been described by Sherman et al., Nature Biotech 16:1050-1053 (1998); Etches et al., *Methods in Molecular Biology* 62: 433-450; Pain et al., *Cells Tissues Organs* 165(3-4): 212-9 (1999); Sang, H., "Transgenic chickens—methods and potential applications", *Trends Biotechnol* 12:415 (1994); and in WO2004003157, "Gene regulation in transgenic animals using a transposon based vector"; and in WO 200075300, "Introducing a nucleic acid into an avian genome, useful for transfecting avian blastodermal cells for producing transgenic avian animals with the desired genes, by directly introducing the nucleic acid into the germinal disc of the egg".

A gammaglobulinemic chicken have been described by Frommel et al., *J Immunol* 105(1): 1-6 (1970); Benedict et al., *Adv Exp Med Biol* 1977; 88(2): 197-205.

The cloning of animals from cells has been described by T. Wakayama et al., *Nature* 1998; 394:369-374; J. B. Cibelli et al., *Science* 280:1256-1258 (1998); J. B. Cibelli et al., *Nature Biotechnology* 1998; 16:642-646; A. E. Schnieke et al., *Science* 278: 2130-2133 (1997); K. H. Campbell et al., *Nature* 380: 64-66 (1996), Kuroiwa et al., Nature Genetics 2004, Jun. 6. Nuclear transfer cloning of rabbits has been described by Stice et al., *Biology of Reproduction* 39: 657-664 (1988), and Challah-Jacques et al., Cloning and Stem Cells 8(4):295-299 (2003).

Production of antibodies from transgenic animals is described in U.S. Pat. No. 5,814,318, No. 5,545,807 and No. 5,570,429. Homologous recombination for chimeric mammalian hosts is exemplified in U.S. Pat. No. 5,416,260. A method for introducing DNA into an embryo is described in U.S. Pat. No. 5,567,607. Maintenance and expansion of embryonic stem cells is described in U.S. Pat. No. 5,453,357.

The mechanisms involved in the diversification of the antibody repertoire in pigs, sheep and cows are reviewed in Butler, J. E. (1998), "Immunoglobulin diversity, B-cell and antibody repertoire development in large farm animals", *Rev Sci Tech* 17:43. Antibody diversification in sheep is described in Reynaud, C. A., C. Garcia, W. R. Hein, and J. C. Weill (1995), "Hypermutation generating the sheep immunoglobulin repertoire is an antigen-independent process", *Cell* 80:115; and Dufour, V., S. Malinge, and F. Nau. (1996), "The sheep Ig variable region repertoire consists of a single VH family," *J Immunol* 156:2163.

C. Detailed Description

Immunoglobulin heavy and light chain genes comprise several segments encoded by individual genes and separated by intron sequences. Thus genes for the human immunoglobulin heavy chain are found on chromosome 14. The variable region of the heavy chain (VH) comprises three gene segments: V, D and J segments, followed by multiple genes coding for the C region. The V region is separated from the C region by a large spacer, and the individual genes encoding the V, D and J segments are also separated by spacers.

There are two types of immunoglobulin light chains: κ and λ. Genes for the human κ light chain are found on chromosome 2 and genes for the human λ light chain are found on chromosome 22. The variable region of antibody light chains includes a V segment and a J segment, encoded by separate gene segments. In the germline configuration of the κ light chain gene, there are approximately 100-200 V region genes in linear arrangement, each gene having its own leader sequence, followed by approximately 5 J gene segments, and C region gene segment. All V regions are separated by introns, and there are introns separating the V, J and C region gene segments as well.

The immune system's capacity to protect against infection rests in a genetic machinery specialized to create a diverse repertoire of antibodies. Antibody-coding genes in B cells are assembled in a manner that allows to countless combinations of binding sites in the variable (V) region. It is estimated that more than $10^{12}$ possible binding structures arise from such mechanisms. In all animals, including humans, the antibody-making process begins by recombining variable (V), diversity (D) and joining (J) segments of the immunoglobulin (Ig) locus. Following this step, depending on the animal species, two general mechanisms are used to produce the diverse binding structures of antibodies.

In some animals, such as human and mouse, there are multiple copies of V, D and J gene segments on the immunoglobulin heavy chain locus, and multiple copies of V and J gene segments on the immunoglobulin light chain locus. Antibody diversity in these animals is generated primarily by gene rearrangement, i.e., different combinations of gene segments to form rearranged heavy chain variable region and light chain variable region. In other animals (e.g., rabbit, birds, e.g., chicken, goose, and duck, sheep, goat, and cow), however, gene rearrangement plays a smaller role in the generation of antibody diversity. For example, in rabbit, only a very limited number of the V gene segments, most often the V gene segments at the 3' end of the V-region, is used in gene rearrangement to form a contiguous VDJ segment. In chicken, only one V gene segment (the one adjacent to the D region, or "the 3' proximal V gene segment"), one D segment and one J segment are used in the heavy chain rearrangement; and only one V gene segment (the 3' proximal V segment) and one J segment are used in the light chain rearrangement. Thus, in these animals, there is little diversity among initially rearranged variable region sequences resulting from junctional diversification. Further diversification of the rearranged Ig genes is achieved by gene conversion, a process in which short sequences derived from the upstream V gene segments replace short sequences within the V gene segment in the rearranged Ig gene. Additional diversification of antibody sequences may be generated by hypermutation.

Immunoglobulins (antibodies) belong into five classes (IgG, IgM, IgA, IgE, and IgD), each with different biological roles in immune defense. The most abundant in the blood and potent in response to infection is the IgG class. Within the human IgG class, there are four sub-classes (IgG1, IgG2, IgG3 and IgG4 isotypes) determined by the structure of the heavy chain constant regions that comprise the Fc domain. The F(ab) domains of antibodies bind to specific sequences (epitopes) on antigens, while the Fc domain of antibodies recruits and activates other components of the immune system in order to eliminate the antigens.

Antibodies have been used successfully as therapeutics since the 1890s when it was found that polyclonal antiserum taken from animals could treat life-threatening infections in humans. A significant advance in antibody research occurred with the development of methods for the recombinant production of antibodies, followed by the development of antibody humanization techniques and method for making fully human monoclonal antibodies in non-human animals.

As a result, chimeric, humanized and human monoclonal antibodies have recently emerged as an important class of pharmaceutical products. While monoclonal antibody-based drugs are very effective in treating diseases when blocking a particular target (e.g. receptor or ligand) certain devastating diseases, such as cancer and infections with virulent pathogens, may be difficult to treat due to their complexity, multifactoral etiology and adaptivity. Monoclonal antibodies address singularly defined targets that change, evolve and mutate during the spread of diseases throughout a population or within an individual. Such adaptive evolution is the bane of mono-specific drugs (e.g. monoclonal antibodies), which are quickly circumvented by resistant strains. Examples abound of bacterial and viral resistance to high-potency antibiotics, and malignant cancers that develop resistance to standard anticancer drugs, such as monoclonal antibody therapies.

In contrast, polyclonal antibodies have the ability to bind and eliminate a plurality of evolving targets linked with complex diseases. By binding multiple antigens, polyclonal antibodies saturate the target and retain activity even in the event of antigen mutation. Following this, through a cascade of signals, polyclonal antibodies induce a potent immune response to eliminate the target antigen, pathogen or cell. These properties make polyclonal antibodies ideal for treating infectious diseases and cancer.

So far, the use of polyclonal antibodies has been severely limited by either supply problems or unwanted reactions to non-human proteins.

The present invention provides a new humanization approach, based on selective humanization the immunoglobulin-coding elements of the immunoglobulin (Ig) translocus. The creation of such human-animal translocus allows for the creation of transgenic animals that express diversified, high-affinity humanized (polyclonal) antibodies in high yields.

Figure 5:
FIG. 5 is a schematic depiction of the rabbit immunoglobulin light chain locus.
Figure 9A:
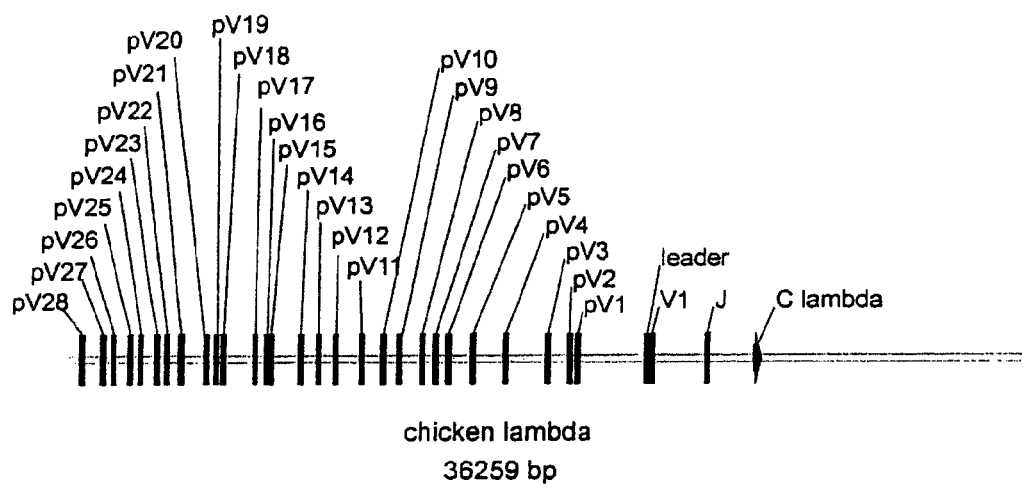
FIG. 9a shows the sequence of a BAC clone comprising a chicken light chain genomic locus whose nucleotide sequence is shown in FIG. 9b (SEQ ID NO: 186).

As a first step, the genomic loci for non-human, including non-primate, immunoglobulin heavy and light chains are identified and sequenced. For example, as part of the present invention, genomic sequences for rabbit and chicken immunoglobulin heavy and light chains were determined, and are shown in FIGS. 1, 5, and 9.

Analysis of the rabbit Ig heavy chain genomic locus has shown that the immunoglobulin heavy chain variable region (Vh) contains numerous genes, including functional genes and non-functional pseudogenes. Alignment of 18 Vh genes has revealed a high degree (80-90%) sequence identity among rabbit heavy chain variable region gene sequences (Vh1-Vh18). The rabbit heavy chain variable region genes have been found to share highest homology with the Vh3 group of the human heavy chain variable region genes. Specifically, sequence comparison of the rabbit Vh1-a2 gene with the human Vh3-23 sequences has revealed 72.8% sequence identity.

Figure 2:
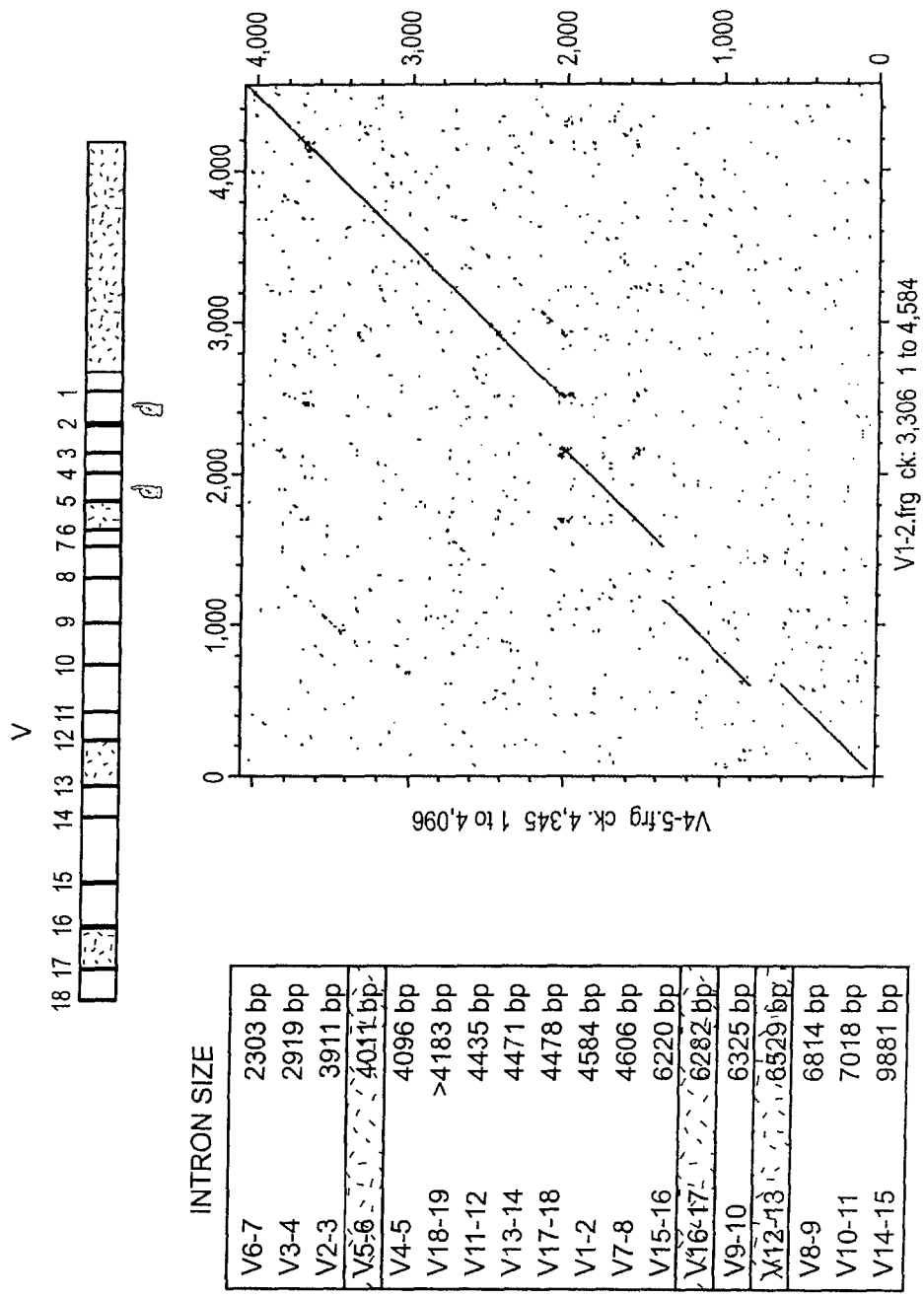
FIGS. 2-4 show a comparison of rabbit heavy chain spacer sequences.
Figure 3:
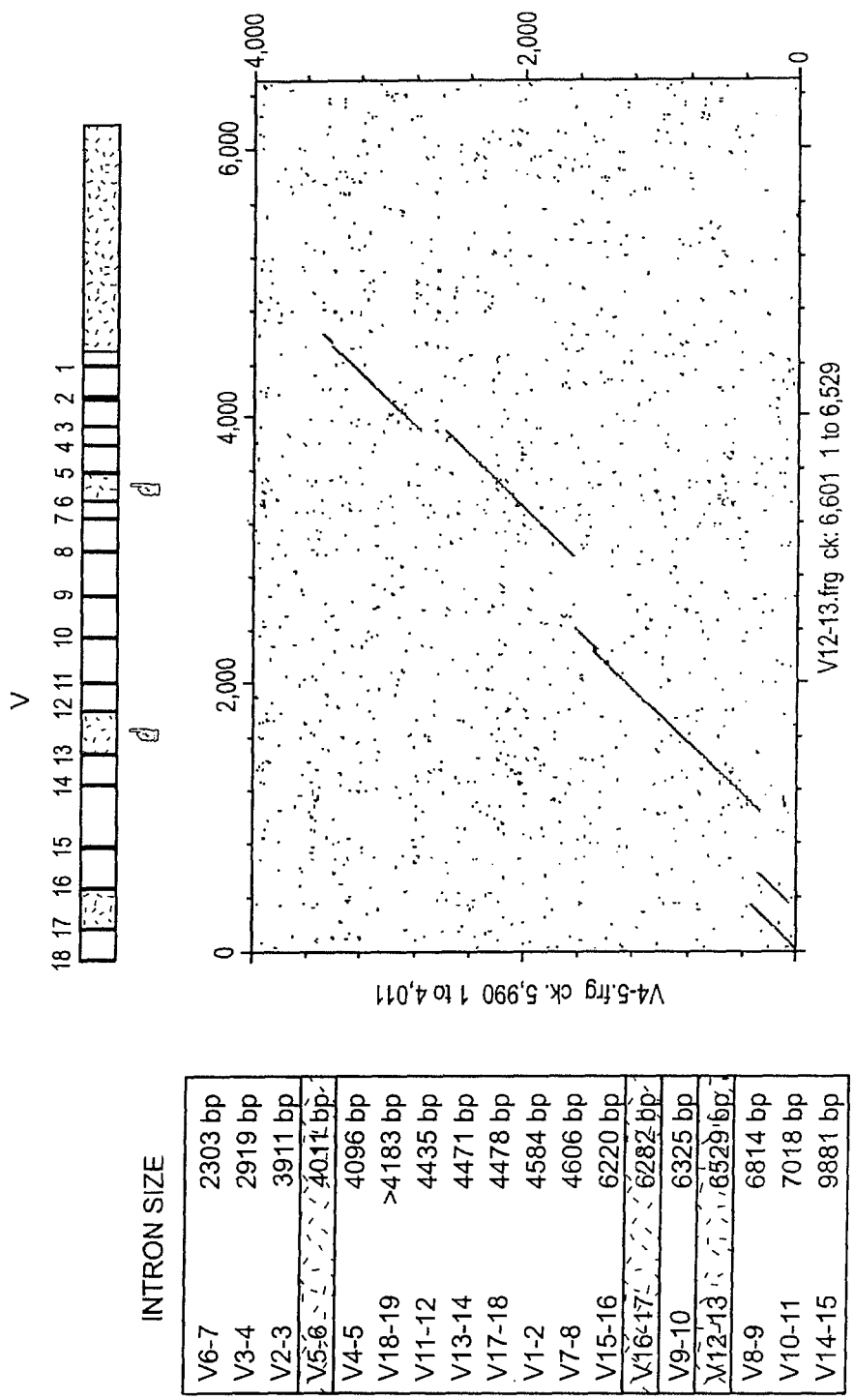
Figure 4:
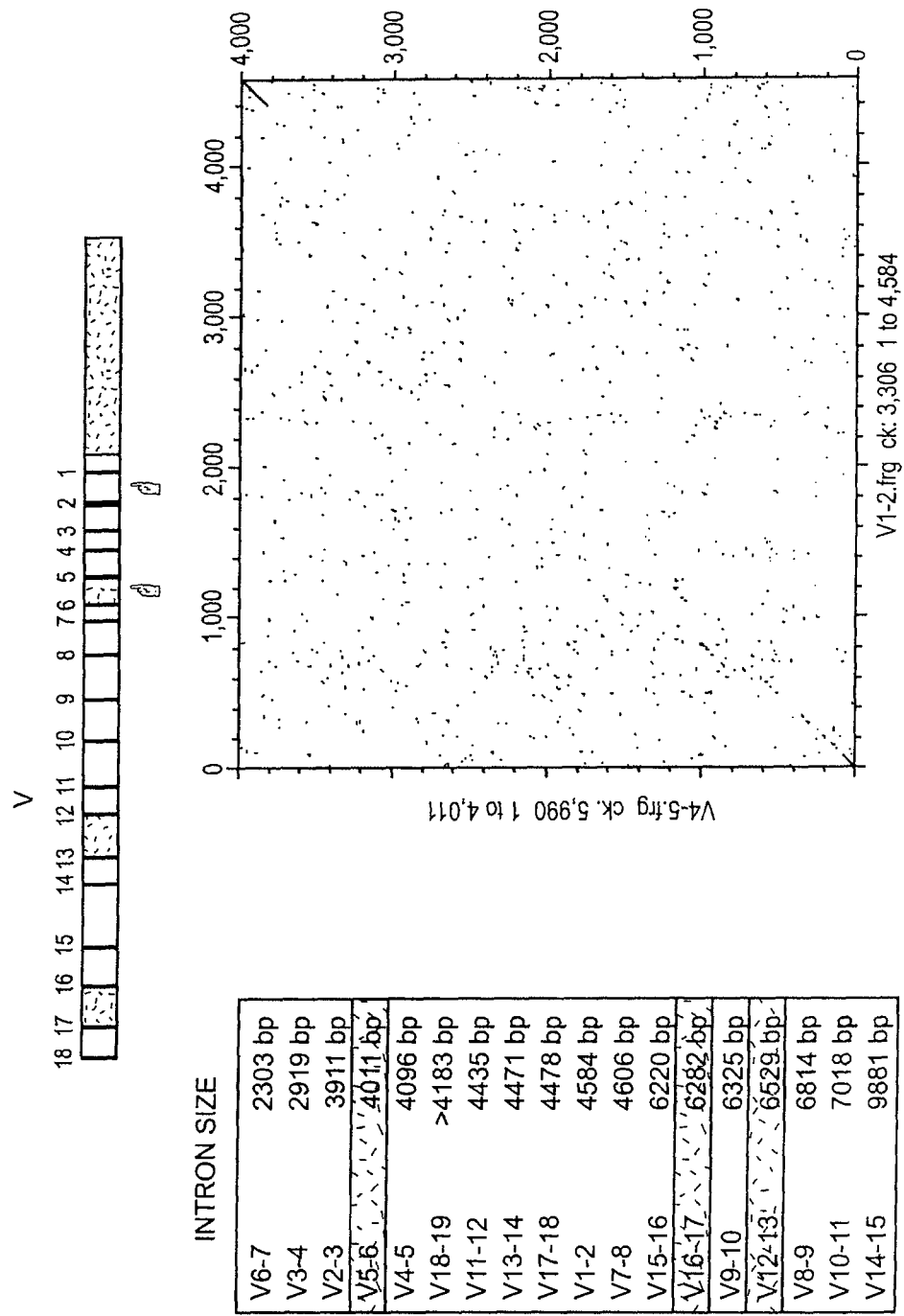

In addition, the non-coding (e.g. intron) sequences separating the rabbit heavy chain variable region gene sequences were analyzed. FIGS. 2-4 show a comparison of rabbit heavy chain intron sequences. It has been found that such intron sequences fall into two groups, and are highly conserved. Especially members of the Group 1 introns show a surprisingly high (80-90%) sequence identity.

Similar findings were made by analysis of rabbit immunoglobulin light chain variable region genomic sequences. In particular, analysis of the rabbit immunoglobulin light chain locus has shown that the light chain variable region (Vl) region contains numerous gene segments, which show a high degree (80-90% sequence identity). It has further been found that the rabbit light chain variable region (Vκ) exhibits high homology with the Vκ1 group of the human light chain variable region gene sequences. Most Vκ sequences have been found to be functional and highly conserved. Unlike in the rabbit heavy chain variable region genes, in the rabbit light chain variable region genes the intron sequences have been found to be heterogeneous.

Similar studies with chicken immunoglobulin heavy and light chain genomic sequences provide analogous results.

In one aspect, the present invention provides spacer sequences, which separate the coding regions in a non-primate animal heavy or light chain gene. In one embodiment, the present invention provides spacer sequences from the heavy and light chain genes of animals which create antibody diversity substantially by gene conversion, including, for example, rabbit and chicken. Such spacer sequences are then used to flank human immunoglobulin heavy or light chain gene segments used in the process of creating a humanized immunoglobulin locus.

The spacer sequences typically comprise at least about 20 nucleotides, or at least about 30 nucleotides, or at least about 40 nucleotides, or at least about 50 nucleotides, and typically are between about 20 and about 10000 nucleotides in length. The spacer sequences may contain a contiguous stretch of nucleotides of appropriate length from a naturally occurring intron sequence in a non-human (e.g. non-primate) animal, or may include an artificial sequence, which may, for example, be a consensus sequence of two or more naturally occurring intron sequences.

The spacer sequences may comprise at least about 20 (30, 40, 50, etc. up to 1000 in 10-nucleotide increments) contiguous nucleotides from a sequence selected from the group consisting of SEQ ID NOS 1 to 185 (Table 1), or from a consensus sequence of two or more of such sequences. It is possible, but not necessary, to separate human heavy or light chain sequences (e.g. V, D, J, C region sequences) used for humanization by spacer sequences that separate the corresponding regions within the genomic sequence of the non-human (non-primate) animal the immunoglobulin of which is humanized.

In general, the humanization of an immunoglobulin (Ig) locus in a non-human animal involves the integration of one or more human Ig gene segments into the animal's genome to create humanized immunoglobulin loci. Thus, creation of a humanized Ig heavy chain locus involves the integration of one or more V and/or D and/or J segments, and/or C region segments into the animal's genome. Similarly, the creation of a humanized Ig light chain locus involves the integration of one or more V and/or J segments, and/or C region segments into the animal's genome.

Depending upon the approach used, the human Ig gene segment(s) can be integrated at the chromosomal location where the endogenous Ig locus of the animal ordinarily resides, or at a different locus of the animal. Regardless of the chromosomal location, the humanized Ig locus of the present invention has the capacity to undergo gene rearrangement and gene conversion and hypermutation in the non-human animal, thereby producing a diversified repertoire of humanized Ig molecules. An Ig locus having the capacity to undergo gene rearrangement and gene conversion is also referred to as a "functional" Ig locus and the antibodies with a diversity generated by a functional Ig locus are also referred to as "functional" antibodies or a "functional" repertoire of antibody molecules.

In a further aspect, the invention provides nucleic acid molecules comprising a human Ig gene segment, flanked by nucleotide sequences which comprise at least bout 20 contiguous nucleotides from a spacer sequence separating the coding regions in a non-primate animal Ig heavy or light chain gene, or from a consensus sequence of two or more of such spacer sequences. The flanking sequences just as the spacer sequence-derived sections within the flanking sequences can be identical or different. The contiguous nucleotides derived from a spacer sequence or from a consensus sequence of two or more spacer sequences can be fused directly to the human Ig gene segment. Alternatively, there might be an intervening sequence between the human Ig gene segment and at least one of the spacer-originating nucleotide sequences. Thus, for example, a flanking sequence at the 5' end of a human V gene segment may include a promoter region, which is linked directly to the human V gene segment, and separates it from the spacer-sequence derived nucleotide stretch of at least 20 nucleotides.

In yet another aspect, the invention concerns a humanized Ig heavy chain locus in which human heavy chain V, D and/or J gene segments and/or C region segments are present in the same configuration as in the original non-human animal immunoglobulin gene, and separated by sequences including at least about 20 contiguous nucleotides from an intron sequence separating the coding regions in a non-primate animal Ig heavy or light chain gene. In another embodiment, the present invention provides a humanized light chain locus in which human light chain C region segments and/or J gene segments and/or V region segments are separated by non-human animal (e.g. non-primate) intron sequences in the same configuration as in the original non-human animal immunoglobulin gene. In a particular embodiment, the spacer sequences are designed based on non-coding, e.g. intron sequences of the non-human (non-primate) animal. In one embodiment, the spacers may retain the appropriate non-coding sequences from the non-human (non-primate) animal. Alternatively, in order to simplify the construct, a consensus sequence, designed based upon the highly homologous non-coding (intron) sequences may be designed, and used as a uniform spacer sequence for the preparation of multiple human heavy or light chain gene segments.

The invention specifically provides isolated nucleic acid sequences and vectors useful in the construction of humanized immunoglobulin loci.

In one embodiment, DNA fragments containing an Ig locus to be humanized are isolated from animals which generate antibody diversity by gene conversion, e.g., rabbit and chicken. Such large DNA fragments can be isolated by screening a library of plasmids, cosmids, yeast artificial chromosomes (YACs) or bacterial artificial chromosomes (BACs), and the like, prepared from the genomic DNA of the non-human, e.g. non-primate animal. An entire animal C-region can be contained in one plasmid or cosmid clone which is subsequently subjected to humanization. YAC clones can carry DNA fragments of up to 2 megabases, thus an entire animal heavy chain locus or a large portion thereof can be isolated in one YAC clone, or reconstructed to be contained in one YAC clone. BAC clones are capable of carrying DNA fragments of smaller sizes (about 150-450 kb). However, multiple BAC clones containing overlapping fragments of an Ig locus can be separately humanized and subsequently injected together into an animal recipient cell, wherein the overlapping fragments recombine in the recipient animal cell to generate a continuous Ig locus.

Human Ig gene segments can be integrated into the Ig locus on a vector (e.g., a BAC clone) by a variety of methods, including ligation of DNA fragments, or insertion of DNA fragments by homologous recombination. Integration of the human Ig gene segments is done in such a way that the human Ig gene segment is operably linked to the host animal sequence in the transgene to produce a functional humanized Ig locus, i.e., an Ig locus capable of gene rearrangement and gene conversion and hypermutation which lead to the production of a diversified repertoire of humanized antibodies.

In one embodiment, human Ig gene segments can be integrated into the Ig locus by homologous recombination. Homologous recombination can be performed in bacteria, yeast and other cells with a high frequency of homologous recombination events. For example, a yeast cell is transformed with a YAC containing an animal's Ig locus or a large portion thereof. Subsequently, such yeast cell is further transformed with a recombination vector as described hereinabove, which carries a human Ig gene segment linked to a 5' flanking sequence and a 3' flanking sequence. The 5' and the 3' flanking sequences in the recombination vector are homologous to those flanking sequences of the animal Ig gene segment on the YAC. As a result of a homologous recombination, the animal Ig gene segment on the YAC is replaced with the human Ig gene segment. Alternatively, a bacterial cell such as E. coli is transformed with a BAC containing an animal's Ig locus or a large portion thereof. Such bacterial cell is further transformed with a recombination vector which carries a human Ig gene segment linked to a 5' flanking sequence and a 3' flanking sequence. The 5' and the 3' flanking sequences in the recombination vector mediate homologous recombination and exchange between the human Ig gene segment on the recombination vector and the animal Ig gene segment on the BAC. Humanized YACs and BACs can be readily isolated from the cells and used in making transgenic animals.

In a further aspect of the present invention, methods of making transgenic animals capable of producing humanized immunoglobulins are provided.

According to the present invention, a transgenic animal capable of making humanized immunoglobulins are made by introducing into a recipient cell or cells of an animal one or more of the transgenic vectors described herein above which carry a humanized Ig locus, and deriving an animal from the genetically modified recipient cell or cells.

The recipient cells may, for example, be from non-human animals which generate antibody diversity by gene conversion and/or hypermutation, e.g., bird (such as chicken), rabbit, cows and the like. In such animals, the 3'proximal V gene segment is preferentially used for the production of immunoglobulins. Integration of a human V gene segment into the Ig locus on the transgene vector, either by replacing the 3'proximal V gene segment of the animal or by being placed in close proximity of the 3'proximal V gene segment, results in expression of human V region polypeptide sequences in the majority of immunoglobulins. Alternatively, a rearranged human V(D)J segment may be inserted into the J locus of the immunoglobulin locus on the transgene vector.

The transgenic vectors containing a humanized Ig locus is introduced into the recipient cell or cells and then integrated into the genome of the recipient cell or cells by random integration or by targeted integration.

For random integration, a transgenic vector containing a humanized Ig locus can be introduced into an animal recipient cell by standard transgenic technology. For example, a transgenic vector can be directly injected into the pronucleus of a fertilized oocyte. A transgenic vector can also be introduced by co-incubation of sperm with the transgenic vector before fertilization of the oocyte. Transgenic animals can be developed from fertilized oocytes. Another way to introduce a transgenic vector is by transfecting embryonic stem cells and subsequently injecting the genetically modified embryonic stem cells into developing embryos. Alternatively, a transgenic vector (naked or in combination with facilitating reagents) can be directly injected into a developing embryo. Ultimately, chimeric transgenic animals are produced from the embryos which contain the humanized Ig transgene integrated in the genome of at least some somatic cells of the transgenic animal.

In a particular embodiment, a transgene containing a humanized Ig locus is randomly integrated into the genome of recipient cells (such as fertilized oocyte or developing embryos) derived from animal strains with an impaired expression of endogenous immunoglobulin genes. The use of such animal strains permits preferential expression of immunoglobulin molecules from the humanized transgenic Ig locus. Examples for such animals include the Alicia and Basilea rabbit strains, as well as Agammaglobinemic chicken strain, as well as immunoglobulin knock-out mice. Alternatively, transgenic animals with humanized immunoglobulin transgenes or loci can be mated with animal strains with impaired expression of endogenous immunoglobulins. Offspring homozygous for an impaired endogenous Ig locus and a humanized transgenic Ig locus can be obtained.

For targeted integration, a transgenic vector can be introduced into appropriate animal recipient cells such as embryonic stem cells or already differentiated somatic cells. Afterwards, cells in which the transgene has integrated into the animal genome and has replaced the corresponding endogenous Ig locus by homologous recombination can be selected by standard methods See for example, Kuroiwa et al, Nature Genetics 2004, Jun. 6. The selected cells may then be fused with enucleated nuclear transfer unit cells, e.g. oocytes or embryonic stem cells, cells which are totipotent and capable of forming a functional neonate. Fusion is performed in accordance with conventional techniques which are well established. Enucleation of oocytes and nuclear transfer can also be performed by microsurgery using injection pipettes. (See, for example, Wakayama et al., Nature (1998) 394:369). The resulting egg cells are then cultivated in an appropriate medium, and transferred into synchronized recipients for generating transgenic animals. Alternatively, the selected genetically modified cells can be injected into developing embryos which are subsequently developed into chimeric animals.

Further, according to the present invention, a transgenic animal capable of producing humanized immunoglobulins can also be made by introducing into a recipient cell or cells, one or more of the recombination vectors described herein above, which carry a human Ig gene segment, linked to 5' and 3' flanking sequences that are homologous to the flanking sequences of the endogenous Ig gene segment, selecting cells in which the endogenous Ig gene segment is replaced by the human Ig gene segment by homologous recombination, and deriving an animal from the selected genetically modified recipient cell or cells.

Similar to the target insertion of a transgenic vector, cells appropriate for use as recipient cells in this approach include embryonic stem cells or already differentiated somatic cells. A recombination vector carrying a human Ig gene segment can be introduced into such recipient cells by any feasible means, e.g., transfection. Afterwards, cells in which the human Ig gene segment has replaced the corresponding endogenous Ig gene segment by homologous recombination, can be selected by standard methods. These genetically modified cells can serve as nuclei donor cells in a nuclear transfer procedure for cloning a transgenic animal. Alternatively, the selected genetically modified embryonic stem cells can be injected into developing embryos which can be subsequently developed into chimeric animals.

Transgenic animals produced by any of the foregoing methods form another embodiment of the present invention.

The transgenic animals have at least one, i.e., one or more, humanized Ig loci in the genome, from which a functional repertoire of humanized antibodies is produced.

In a specific embodiment, the present invention provides transgenic rabbits having one or more humanized Ig loci in the genome. The transgenic rabbits of the present invention are capable of rearranging and gene converting the humanized Ig loci, and expressing a functional repertoire of humanized antibodies.

In another specific embodiment, the present invention provides transgenic chickens having one or more humanized Ig loci in the genome. The transgenic chickens of the present invention are capable of rearranging and gene converting the humanized Ig loci, and expressing a functional repertoire of humanized antibodies In another specific embodiment, the present invention provides transgenic mice with one or more humanized V regions in the genome. The humanized V region comprises at least two human V gene segments flanked by non-human spacer sequences. The transgenic mice are capable of rearranging the human V elements and expressing a functional repertoire of antibodies.

Once a transgenic non-human animal capable of producing diversified humanized immunoglobulin molecules is made, humanized immunoglobulins and humanized antibody preparations against an antigen can be readily obtained by immunizing the animal with the antigen. A variety of antigens can be used to immunize a transgenic host animal. Such antigens include, without limitation, microorganisms, e.g. viruses and unicellular organisms (such as bacteria and fungi), alive, attenuated or dead, fragments of the microorganisms, or antigenic molecules isolated from the microorganisms.

Exemplary bacterial antigens for use in immunizing an animal include purified antigens from *Staphylococcus aureus* such as capsular polysaccharides type 5 and 8, recombinant versions of virulence factors such as alpha-toxin, adhesin binding proteins, collagen binding proteins, and fibronectin binding proteins. Exemplary bacterial antigens also include an attenuated version of *S. aureus, Pseudomonas aeruginosa, enterococcus, enterobacter*, and *Klebsiella pneumoniae*, or culture supernatant from these bacteria cells. Other bacterial antigens which can be used in immunization include purified lipopolysaccharide (LPS), capsular antigens, capsular polysaccharides and/or recombinant versions of the outer membrane proteins, fibronectin binding proteins, endotoxin, and exotoxin from *Pseudomonas aeruginosa, enterococcus, enterobacter*, and *Klebsiella pneumoniae.*

Exemplary antigens for the generation of antibodies against fungi include attenuated version of fungi or outer membrane proteins thereof, which fungi include, but are not limited to, *Candida albicans, Candida parapsilosis, Candida tropicalis*, and *Cryptococcus neoformans.*

Exemplary antigens for use in immunization in order to generate antibodies against viruses include the envelop proteins and attenuated versions of viruses which include, but are not limited to respiratory synctial virus (RSV) (particularly the F-Protein), Hepatitis C virus (HCV), Hepatits B virus (HBV), cytomegalovirus (CMV), EBV, and HSV.

Therapeutic antibodies can be generated for the treatment of cancer by immunizing transgenic animals with isolated tumor cells or tumor cell lines; tumor-associated antigens which include, but are not limited to, Her-2-neu antigen (antibodies against which are useful for the treatment of breast cancer); CD19, CD20, CD22 and CD53 antigens (antibodies against which are useful for the treatment of B cell lymphomas), (3) prostate specific membrane antigen (PMSA) (antibodies against which are useful for the treatment of prostate cancer), and 17-1A molecule (antibodies against which are useful for the treatment of colon cancer).

The antigens can be administered to a transgenic host animal in any convenient manner, with or without an adjuvant, and can be administered in accordance with a predetermined schedule.

After immunization, serum or milk from the immunized transgenic animals can be fractionated for the purification of pharmaceutical grade polyclonal antibodies specific for the antigen. In the case of transgenic birds, antibodies can also be made by fractionating egg yolks. A concentrated, purified immunoglobulin fraction may be obtained by chromatography (affinity, ionic exchange, gel filtration, etc.), selective precipitation with salts such as ammonium sulfate, organic solvents such as ethanol, or polymers such as polyethyleneglycol.

For making a monoclonal antibody, spleen cells are isolated from the immunized transgenic animal and used either in cell fusion with transformed cell lines for the production of hybridomas, or cDNAs encoding antibodies are cloned by standard molecular biology techniques and expressed in transfected cells. The procedures for making monoclonal antibodies are well established in the art. See, e.g., European Patent Application 0 583 980 A1 ("Method For Generating Monoclonal Antibodies From Rabbits"), U.S. Pat. No. 4,977,081 ("Stable Rabbit-Mouse Hybridomas And Secretion Products Thereof"), WO 97/16537 ("Stable Chicken B-cell Line And Method of Use Thereof"), and EP 0 491 057 B1 ("Hybridoma Which Produces Avian Specific Immunoglobulin G"), the disclosures of which are incorporated herein by reference. In vitro production of monoclonal antibodies from cloned cDNA molecules has been described by Andris-Widhopf et al., "Methods for the generation of chicken monoclonal antibody fragments by phage display", *J Immunol Methods* 242:159 (2000), and by Burton, D. R., "Phage display", *Immunotechnology* 1:87 (1995), the disclosures of which are incorporated herein by reference.

Cells derived from the transgenic animals of the present invention, such as B cells or cell lines established from a transgenic animal immunized against an antigen, are also part of the present invention.

In a further aspect of the present invention, methods are provided for treating a disease in a primate, in particular, a human subject, by administering a purified humanized antibody composition, preferably, a humanized polyclonal antibody composition, desirable for treating such disease.

In another aspect of the present invention, purified monoclonal or polyclonal antibodies are admixed with an appropriate pharmaceutical carrier suitable for administration in primates especially humans, to provide pharmaceutical compositions. Pharmaceutically acceptable carriers which can be employed in the present pharmaceutical compositions can be any and all solvents, dispersion media, isotonic agents and the like. Except insofar as any conventional media, agent, diluent or carrier is detrimental to the recipient or to the therapeutic effectiveness of the antibodies contained therein, its use in the pharmaceutical compositions of the present invention is appropriate. The carrier can be liquid, semi-solid, e.g. pastes, or solid carriers. Examples of carriers include oils, water, saline solutions, alcohol, sugar, gel, lipids, liposomes, resins, porous matrices, binders, fillers, coatings, preservatives and the like, or combinations thereof.

The humanized polyclonal antibody compositions used for administration are generally characterized by containing a polyclonal antibody population, having immunoglobulin concentrations from 0.1 to 100 mg/ml, more usually from 1 to 10 mg/ml. The antibody composition may contain immunoglobulins of various isotypes. Alternatively, the antibody composition may contain antibodies of only one isotype, or a number of selected isotypes.

In most instances the antibody composition consists of unmodified immunoglobulins, i.e., humanized antibodies prepared from the animal without additional modification, e.g., by chemicals or enzymes. Alternatively, the immunoglobulin fraction may be subject to treatment such as enzymatic digestion (e.g. with pepsin, papain, plasmin, glycosidases, nucleases, etc.), heating, etc, and/or further fractionated.

The antibody compositions generally are administered into the vascular system, conveniently intravenously by injection or infusion via a catheter implanted into an appropriate vein. The antibody composition is administered at an appropriate rate, generally ranging from about 10 minutes to about 24 hours, more commonly from about 30 minutes to about 6 hours, in accordance with the rate at which the liquid can be accepted by the patient. Administration of the effective dosage may occur in a single infusion or in a series of infusions. Repeated infusions may be administered once a day, once a week once a month, or once every three months, depending on the half-life of the antibody preparation and the clinical indication. For applications on epithelial surfaces the antibody compositions are applied to the surface in need of treatment in an amount sufficient to provide the intended end result, and can be repeated as needed. In addition, antibodies can, for example, be administered as an intramuscular bolus injection, which may, but does not have to, be followed by continuous administration, e.g. by infusion.

The antibody compositions can be used to bind and neutralize antigenic entities in human body tissues that cause disease or that elicit undesired or abnormal immune responses. An "antigenic entity" is herein defined to encompass any soluble or cell-surface bound molecules including proteins, as well as cells or infectious disease-causing organisms or agents that are at least capable of binding to an antibody and preferably are also capable of stimulating an immune response.

Administration of an antibody composition against an infectious agent as a monotherapy or in combination with chemotherapy results in elimination of infectious particles. A single administration of antibodies decreases the number of infectious particles generally 10 to 100 fold, more commonly more than 1000-fold. Similarly, antibody therapy in patients with a malignant disease employed as a monotherapy or in combination with chemotherapy reduces the number of malignant cells generally 10 to 100 fold, or more than 1000-fold. Therapy may be repeated over an extended amount of time to assure the complete elimination of infectious particles, malignant cells, etc. In some instances, therapy with antibody preparations will be continued for extended periods of time in the absence of detectable amounts of infectious particles or undesirable cells. Similarly, the use of antibody therapy for the modulation of immune responses may consist of single or multiple administrations of therapeutic antibodies. Therapy may be continued for extended periods of time in the absence of any disease symptoms.

The subject treatment may be employed in conjunction with chemotherapy at dosages sufficient to inhibit infectious disease or malignancies. In autoimmune disease patients or transplant recipients, antibody therapy may be employed in conjunction with immunosuppressive therapy at dosages sufficient to inhibit immune reactions. The invention is further illustrated, but by no means limited, by the following examples.

EXAMPLE 1

Isolation and Sequencing of BAC Clones Containing Rabbit Immunoglobulin Loci

High molecular weight DNA was isolated from a2b5 male rabbits. The rabbits were euthanized, spleen and kidneys were removed and rinsed in ice-cold PBS. Fat and connecting tissues were removed and processed separately. The organs were cut into pieces and homogenized in a pre-cooled Dounce homogenizer. The supernatant was transferred into cooled 50 ml falcon tubes, mixed with cold PBS and large tissue debris was allowed to sink to the bottom for 2 minutes. Cells in the supernatant were pelleted at 200 g for 10 min at 4° C., washed once with PBS, resuspended in 1 ml PBS and counted. Sets of $5 \times 10^6$, $5 \times 10^7$ and $5 \times 10^8$ cells were embedded in agarose plugs using the CHEF Mammalian Genomic DNA Plug Kit (BIORAD) To optimize conditions for partial digestion with HindIII, plugs were cut into 5 equal pieces and digested with 1 to 10 units of HindIII for various times and temperatures. Best results were obtained with 2 units HindIII at 4° C. for 3 hrs or 37° C. for 25 min. Digested DNA was double size fractioned on a Pulse Field Gel Electrophoresis (PFGE) apparatus using the following parameters: 6 hr backwards, 15 s switch times; 6 hr forwards, 15 s switch times; 20 hr forwards, 90 s switch times; 200V 14° C. The area of the gel with the desired size of partial digested DNA was cut and DNA was isolated using gelase. 11 ng of insert was ligated with 1 ng of HindIII digested pBELOBAC 11 and electroporated into DH10B cells. 1% of the resulting colonies was sized using NotI and revealed an average insert size of 124 kb. $1 \times 10^5$ clones were spotted on Nylon filters and screened by hybridization with specific probes.

Probes for screening were amplified by PCR using genomic DNA from rabbits, cloned into pBlueScript, and verified by sequencing. Primer pairs (SEQ ID NO: 193-208, Table 2) were designed according to published sequences. Several BACs representing rabbit heavy and light chain immunoglobulin loci were isolated and mapped (FIGS. 1 and 5). BACs 219D23 219D23 (GenBank Acc. No. AY386695), 225P18 (GenBank Acc. No. AY386697), 27N5 (GenBank Acc. No. AY386696), 38A2 (GenBank Acc. No. AY386694), 179L1 (GenBank Acc. No. AY495827), 215M22 (GenBank Acc. No. AY495826), 19 (GenBank Acc. No. AY495828) and Fosmid Fos15B (GenBank Acc. No. AY3866968) were sequenced. Shotgun libraries for sequencing were constructed in pCR-Blunt with an insert size of 1.5-2 kb. For sequence analysis the STADEN package (Roger Staden, Cambridge, UK) was used. The software modules pregap and gap4 were used for assembly and gap closure. For the quality clipping of sequences PHRED (Washington University) and the STADEN package was coupled.

EXAMPLE 2

Construction of a Humanized Rabbit Immunoglobulin Heavy Chain Locus

BAC and fosmid clones containing rabbit immunoglobulin heavy chain locus sequences were isolated from genomic DNA libraries using probes specific for the constant, variable, and joining gene segments or the 3' enhancer region. Isolated BACs (FIG. 1) 27N5 (GenBank Acc. No. AY386696), 219D23 (GenBank Acc. No. AY386695), 225P18 (GenBank Acc. No. AY386697), 38A2 (GenBank Acc. No. AY386694) and fosmid Fos15B (GenBank Acc. No. AY3866968) were sequenced (Ros et al., *Gene* 330, 49-59).

Selected immunoglobulin coding sequences were exchanged with corresponding human counterparts by homologous recombination in *E. Coli* by ET cloning (E-Chiang Lee et al., *Genomics* 73, 56-65 (2001); Daiguan Yu et al., *PNAS* 97, 5978-5983 (2000); Muyrers et al., *Nucleic Acids Research* 27, 1555-1557 (1999); Zhang et al., *Nature Biotechnology* 18, 1314-1317 (2000)).

Alternatively, DNA fragments were recombined by ligation in vitro and subsequent transformation of *E. coli*. BACs and/or Fos15B or parts thereof were combined by in vitro ligation and transformation, ET cloning, or by Cre recombinase mediated integration.

For ET cloning, vectors containing target sequence were transformed into a streptomycin resistant *E. coli* strain containing the inducible lambda phage recombination enzymes Redα, Redβ and γ. These recombination proteins were expressed either from a co-transfected plasmid (DH10B *E. coli* cells with plasmid pSC101) or from a genomic integrated lambda prophage (DY380 *E. coli* strain). The ET cloning procedure encompassed two homologous recombination steps.

In a first step the target locus was replaced by a selection-counter selection cassette (e.g. neo-rpsL which confers resistance to neomycin (neo) and sensitivity to streptomycin (rpsL)). After isolation of neo-resistant colonies, insertion of the selection cassette by homologous recombination was confirmed by restriction enzyme analysis and partial sequencing.

In a second step, the rpsL-neo selection cassette was exchanged with a new sequence. Streptomycin resistant clones were analyzed by restriction analysis and sequencing. Fragments used for the ET cloning procedure had flanking sequences of 20 to 50 bp length, which were identical to target sequences. Sequences used for ligation had appropriate restriction enzyme sites at their 3' and 5' ends. These sites were either naturally occurring sites or they were introduced by PCR using primers containing appropriate sites.

Alternatively, sequences were generated synthetically.

A humanized heavy chain was constructed by replacement of rabbit $J_H$, Cμ in BAC 219D23 and Cγ in BAC 27N5 with their corresponding human counterparts by ET cloning. Human sequences used for the ET cloning procedures were amplified by PCR from human genomic DNA.

Human Cμ, Cγ and $J_H$ gene segments was amplified using primers (SEQ ID Nos: 209-214, Table 2) with 50 bp homologies to rabbit target sequences.

After ligation of BAC clone 225P18 with clone 219D23 and BAC 27N5 with Fosmid 15B, the ligated constructs were transformation into *E. coli* and connected by Cre recombinase mediated insertion. This resulted in a functional locus consisting of 18 rabbit variable genes, rabbit D region, human J region, human Cμ, human Cγ, rabbit Cε, rabbit Cα4 and the 3'enhancer element.

For the generation of transgenic animals the humanized BAC clones were coinjected either separately as three overlapping BACs (225P18 and 219D23 and BAC 27N5) or two overlapping combined BACs (225P18-219D23 and BAC 27N5-Fosmid 15B) or as one BAC (225P18-219D23-27N5-Fosmid 15B). Founder animals with transgenes were identified by PCR.

EXAMPLE 3

Figure 13E:
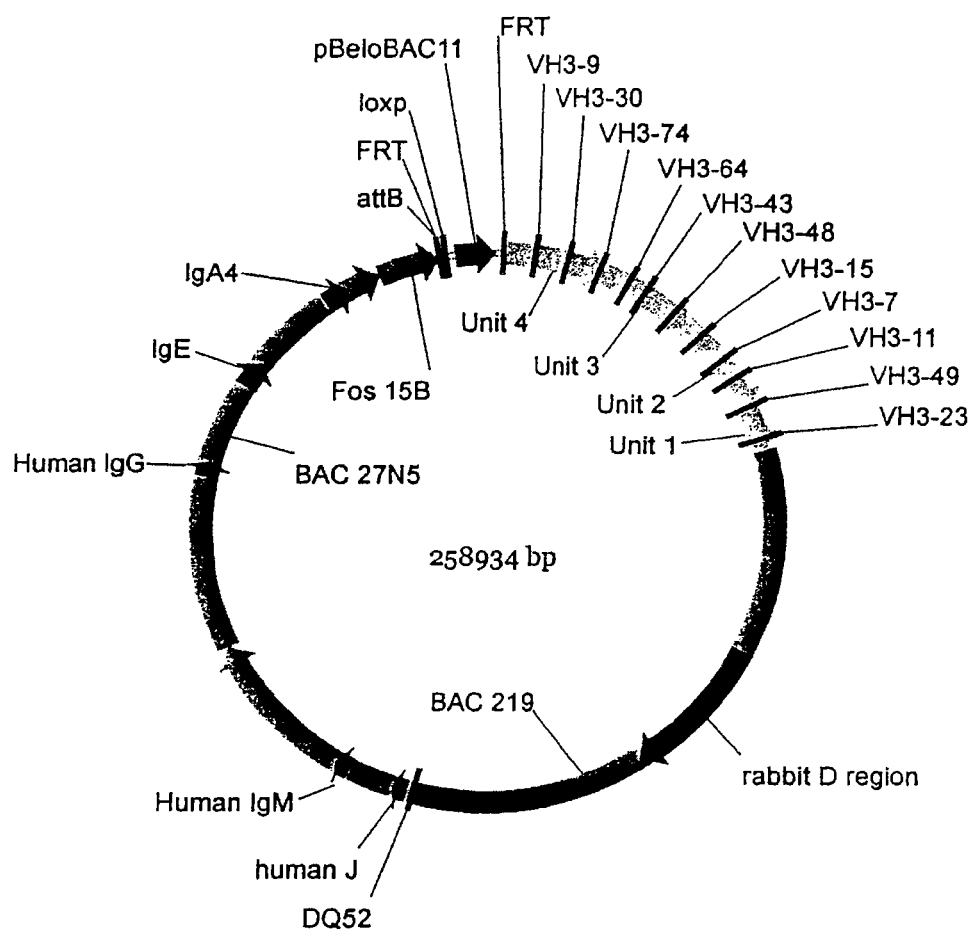

Construction of a Humanized Immunoglobulin Heavy Chain Locus Using Synthetic Fragments Four fragments denoted Unit1, Unit2, Unit3, and Unit 4 (FIG. 13, SEQ ID Nos: 189-192) with human V sequences and rabbit spacers were chemically synthesized. Each fragment was flanked 5' by an AscI restriction endonuclease recognition sequence, 3' by a lox71 Cre recombinase recognition sequence followed by Fse I and MluI restriction enzyme recognition sequences. Unit 1 consisted of human $V_H3$-49, $V_H3$-11, $V_H3$-7 and $V_H3$-15 variable genes separated by rabbit spacers I29-30, I3-4, I2-3 and the 3' half of I1-2 (I1-2B). Unit 2 consisted of human $V_H3$-48, $V_H3$-43 and $V_H3$-64 separated by rabbit spacers I1-2A (5' half of I1-2), I7-8, I6-7 and the 3' half of I4-5 (I4-5B). Unit 3 consisted of human $V_H3$-74, $V_H3$-30, and $V_H3$-9 separated by the rabbit spacer sequences I4-5B, I26-27, I11-12 and I17-18.

Unit 3 had in addition to the afore mentioned upstream flanks an Flp recombinase recognition target (FRT) sequence, followed by a SglfI restriction endonuclease recognition sequence preceding the already mentioned Asc I site.

Unit 4 had the human $V_H3$-23 gene 5' flanked by the rabbit spacer I1-2, a lox66 Cre recombinase target sequence and an AscI endonuclease recognition sequence, and 3' flanked by IV-C (5' half) rabbit spacer sequence followed by a MluI endonuclease recognition sequence.

A gentamycin selection cassette was PCR-amplified, using primers SEQ ID NOs 215 and 216 (Table 2) containing AscI and FseI sites and ligated into a pGEM vector with a modified cloning site including AscI, FseI, and MluI endonuclease recognition sites (pGEM.Genta modified by PCR using SEQ ID NOs 217 and 218, Table 2).

Units 1, 2 and 3 were cloned into pGEM.Genta (Promega) vectors.

Unit 4 was sub-cloned into a customized pBELOBAC11 (NEB) vector linearized with Hind III, and PCR-amplified. The forward primer (SEQ ID NO: 219, Table 2) had restriction sites for HindIII, PacI and AatII, and the reverse primer (SEQ ID NO: 220) sites for Bam HI, MluI and AscI. The primers were designed in such a way that the pBELOBAC11 Chloramphenicol selection cassette was deleted. Furthermore, a Neomycin selection cassette was PCR-amplified with primers SEQ ID NOs 221 and 222 (Table 2) carrying Bam HI and Hind III restriction sites, and ligated to the modified pBELOBAC11 vector (pBB11.1).

Units 1-4 were assembled by cre-mediated recombination as described (Mejia et al, *Genomics* 70(2) 165-70 (2000)). First Unit 1 was cloned into the customized pgem.Genta vector, digested with Fse I and subsequently recircularized by ligation. This vectorless construct was transformed into *E. coli* containing pBB11.1.Unit4 and p706-Cre plasmid. Following recombination of Unit 1 with PBB11.1 unit 4, positive clones (Unit4/1) were selected on kanamycin and gentamycin containing media. Clones were characterized by restriction analyses using various enzymes.

For recombination of Unit 2, the Unit4/1 insert was excised by double digestion with AscI and PacI, and cloned into pBELOBAC11 with a modified linker (pBB11.2: modified by PCR using primers SEQ ID NOs 223 and 224, Table 2).

pBELOBAC11 was linearized with HindIII and PCR-amplified with a forward primer encoding PacI and AatII endonuclease recognition sites and a reverse primer encoding MluI and NotI endonuclease recognition sites and a lox66 Cre recombinase target site. For ligation with Unit1/4 the pBB11.2 vector was opened with MluI and PacI. pGEM.Genta.Unit2 was converted into a circular vectorless construct as described for pGEM.Genta.Unit1 and connected with pBB11.2.Unit4/1 by in vivo Cre mediated recombination. Subsequently, the resulting construct pBB11.2.Unit4/1/2 is prepared for Cre mediated recombination with Unit 3 by replacing the wild type loxp site with a lox66 target site by ET-cloning (Muyrers et al., *Nucleic Acids Research* 27, 1555-

1557 (1999); Muyrers et at *Trends Biochem. Sci.* 26(5):325-31 (2001)). A chloramphenicol selection cassette was amplified by PCR with primers (SEQ ID NOs 225 and 226, Table 2) containing 50 bp sequences homologous to the BAC target sequence. The reverse primer included a lox66 site. The gel-purified PCR product was transformed into cells carrying the target BAC as well as the pSC101 plasmid, required for homologous recombination. Positive clones were selected with chloramphenicol and confirmed by restriction analysis and sequencing. pGEM.Genta.Unit 3 was prepared for in vivo recombination as described above for Unit1 and 2 and transformed into cells carrying the receptor BAC, as well as the p706-Cre plasmid. Positive clones pBB11.2.Unit4/1/2/3 were selected with gentamycin and confirmed by restriction analysis. pBB11.2.Unit4/1/2/3 was further modified by ET-cloning to generate a lox 71 target site. Subsequently, pBB11.2.Unit4/1/2/3 was connected to fragments from BACs 219D23, 27N5 and Fos15B.

EXAMPLE 4

Construction of a Humanized Immunoglobulin Heavy Chain Locus Using PCR Amplified Fragments Human $V_H$ elements were amplified using genomic DNA (ClonTech) and primers SEQ ID NOs 227-248 (Table 2). PCR products were analyzed by gel-electrophoresis and gel purified using the GENECLEAN kit (Q-Biogen). Subsequently, amplification products were sub-cloned into Zero-Blunt TOPO™ (Invitrogen), according to the manufacturer's instructions. The sequences of all amplified V elements were confirmed. For the construction of the humanized V region, V elements were amplified using plasmid DNA as template and primers SEQ ID NOs 249-270 (Table 2). Forward primers contained an AscI site, followed by a rabbit splice site. Reverse primers contained a rabbit recombination signal sequence (RSS) and a MluI restriction site. PCR products were gel purified using the GENECLEAN kit.

Human $V_H$s, V3-33, V3-74, V3-49, V3-21, V3-48, V3-73, V3-7, and V3-D could not be isolated by PCR and were synthesized chemically (BlueHeron, Bothel, Wash.). Restriction sites and rabbit regulatory sequences were added during synthesis.

Rabbit spacer sequences were amplified using BACs 38A2 and 225P18 as templates and primers SEQ ID NOs 271-288 (Table 2). BAC 225P18 was double digested with NheI and a 41 kb fragment was gel purified. This fragment served as a template for the amplification of spacers V1-2, V2-3, V3-4, V4-5, and V5-6.

BAC 225P18 was digested with BstBI and the template for spacers V6-7 and V7-8 was gel-purified. A double digestion of BAC 38A2 with PacI and RsrII allowed gel purification of the template for spacers V21-22, and V22-23.

Amplified spacer sequences were gel-purified, and sub-cloned into XL-PCR-TOPO™ (Invitrogen) according to the manufacturer's instructions.

$V_H$ elements and rabbit spacer sequences were sub-cloned into modified pGEM (Promega) and pBS (Strategene) vectors. The pGEM vector was cut with NotI and Hind III and ligated with chemically synthesized oligonucleotide sequences containing FseI, AscI and MluI sites (Oligo1: SEQ ID NO: 289; Oligo2: SEQ ID NO: 290; Table 2). Vector pBS was cut with SacI and KpnI and ligated with a chemically synthesized oligonucleotide sequence containing the restriction sites FseI, AscI and MluI (Oligo1: (SEQ ID NO: 291; Oligo2: SEQ ID NO: 292, Table 2).

Gentamycin and neomycin selection cassettes were amplified using primers (SEQ ID NOs: 293-296, Table 2) with Fse I or AscI sites and ligated into the modified pGEM and pBS-vectors.

The final construct is built in a modified pBeloBAC II vector. The pBeloBAC II vector was opened with BamHI and HindIII and the cloning sites were modified to contain FseI, AscI, MluI sites using a chemically synthesized oligonucleotide sequence (Oligo1: SEQ ID NO: 297; Oligo2: SEQ ID NO: 298, Table 2).

BAC 219D23 was modified by introduction of restriction sites using ET-cloning (Muyrers et al., *Nucleic Acids Research* 27, 1555-1557 (1999); Muyers et at *Trends Biochem. Sci.* 26(5):325-31 (2001)). The Neomycin selection cassette was amplified with primers SEQ ID NO: 299 and SEQ ID NO: 300 (Table 2). The forward primer contained an FseI site, the reverse primer an AscI site.

The purified PCR product was transformed into *E. coli* cells carrying BAC 219D23 and plasmid pSC101 necessary for homologous recombination. After homologous recombination of the cassette and the target sites in the BAC, introduced restriction sites were confirmed by restriction analysis. Subsequently, the modified BAC 219D23 was digested with FseI and MluI and the resulting 17 kb fragment (containing the FseI-Neo-AscI cassette) was separated by PFGE and purified by electro-elution. This purified fragment was ligated with the modified pBeloBAC II vector opened with FseI and MluI.

Figure 6:
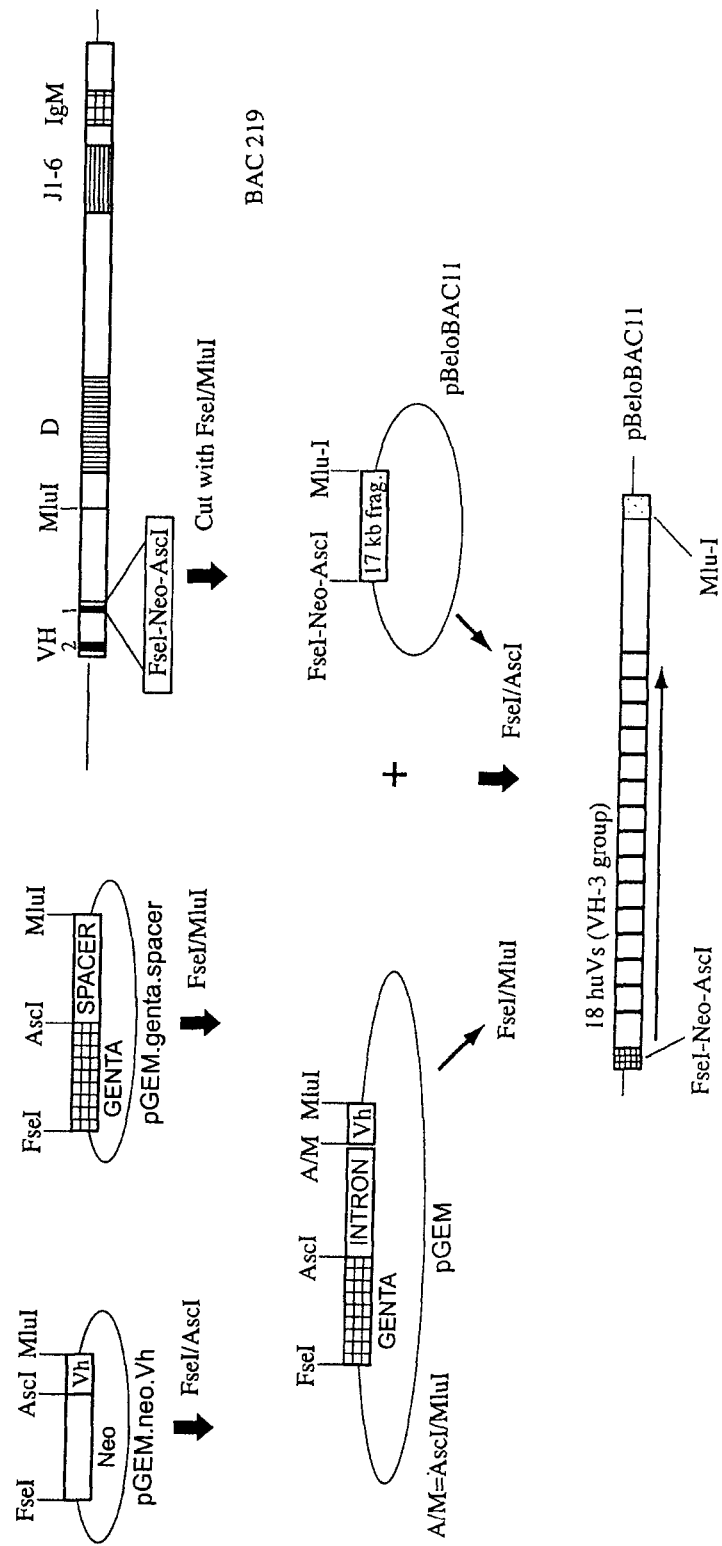
FIG. 6 illustrates the building of an immunoglobulin gene V locus using human $V_H$ and rabbit spacer elements.

A purified DNA fragment encoding a human $V_H$ element is ligated with the modified pGEM.neo vector opened with AscI and MluI. Similarly a spacer sequence is sub-cloned into the modified pGEM.genta vector. Subsequently, the pGEM-.genta vector carrying the spacer sequence is cut with FseI and MluI and the insert is ligated with pGEM.neo.$V_H$ vector opened with FseI and AscI. This step is repeated several times to build a fragment consisting of several spacer and $V_H$ segments. Such fragments are excised with FseI and MluI and ligated with the modified pBeloBAC II vector linearized with FseI and AscI. These processes are repeated to build a large immunoglobulin V region (FIG. 6). The humanized heavy chain locus is used for the generation of transgenic animals.

EXAMPLE 5

Construction of a Humanized Rabbit Light Chain Locus Containing Humanized Ck and Humanized Rearranged VJ Screening of a rabbit genomic BAC libraries resulted in the identification of three BACs (215M22, 179L1 and 19O2; Gene Bank Accession Nos: AY495826, AY495827, and AY495828, respectively) containing rabbit light chain K1 gene segments. Rabbit Cκ☐ was exchanged with human Cκ☐ allotype Km3 by ET cloning as described (E-Chiang Lee et al., *Genomics* 73, 56-65 (2001); Daiguan Yu et al., *PNAS* 97, 5978-5983 (2000); Muyrers et al., *Nucleic Acids Research* 27, 1555-1557 (1999); Zhang et al., *Nature Biotechnology* 18, 1314-1317 (2000)). Human Cκ (allotype Km3) was amplified by PCR with primers (SEQ ID Nos 301 and 302, Table 2) containing 50 bp sequences homologous to target sequences. Homology arms were designed based on the published sequence of rabbit germline kappa (b5; GenBank Accession No. K01363) and matched the intron-exon boundary of Cκ. The exchange of rabbit Cκagainst the human Cκ in BAC 179L1 was verified by sequencing.

BAC 179L1-huCk was modified by two ET cloning. A neomycin selection cassette was amplified with primers (SEQ ID NOs 303 and 304, Table 2) containing 50 bp sequences homologous to BAC 179L1. The forward primer additionally had an i-CeuI meganuclease site. The PCR product was used for ET cloning. Positive clones were selected with neomycin and checked for correctness by restriction enzyme digests and sequencing. A zeocin selection cassette was amplified with primers (SEQ ID NOs 305 and 306, Table 2) containing 50 bp sequences homologous to BAC 179L1. The forward primer additionally had an i-SceI meganuclease site. The PCR product was used for ET cloning. Positive clones were selected with zeozin and checked for correctness by restriction enzyme digests and sequencing.

BAC 215M22 was modified by one ET cloning. A gentamycin resistance gene was amplified with primers (SEQ ID NOs 307 and 308, Table 2) containing 50 bp sequences homologous to BAC215M22. The forward primer additionally had an i-CeuI Meganuclease site and the reverse primer an i-SceI meganuclease site. The PCR product was used for ET cloning. Resulting clones were selected with gentamycin and analyzed by restriction enzyme digests and sequencing.

Modified BAC179L1 and 225M22 were cut with i-CeuI and i-SceI. Fragments of 98 kb and 132 kb were purified and ligated. Resulting clones were selected with kanamycin and chloramphenicol and checked for correctness by restriction enzyme digests, PCR of the regions containing i-SceI and i-CeuI restriction sites, and sequencing. The resulting BAC was termed 179-215-huCk.

Rabbit JK1 and JK2 of BAC 179-215-huCk were replaced by ET cloning with a synthetic human rearranged VκJκ gene. A DNA fragment with rabbit promoter, rabbit leader, rabbit intron and human VκJκ gene was synthesized chemically. The codon usage of the synthetic human VJ was optimised to achieve highest DNA sequence homology to rabbit V kappa genes.

The synthetic human VJ was PCR amplified with a forward primer (SEQ ID NO 309, Table 2) containing 50 bp sequences homologous to BAC 179L1 and a reverse primer (SEQ ID NO 310, Table 2) containing a sequence homologous to the gentamycin resistance gene and a FRT site. A gentamycin resistance gene was amplified with a forward primer (SEQ ID NO 311, Table 2) containing a FRT site and a reverse primer (SEQ ID NO 312, Table 2) with 50 bp homology to BAC 179L1 and a FRT site. The human synthetic human VJ and the gentamycin resistance gene were combined by overlap extension PCR using the forward primer for the synthetic human VJ gene and the reverse primer for the gentamycin resistance gene. The resulting fragment was used for ET cloning. Positive clones were selected with gentamycin and checked for correctness by restriction enzyme digests and sequencing.

The gentamycin resistance gene was removed by site specific recombination via expression of Flp recombinase. After recombination one FRT was left. The FRT site was deleted by ET cloning. A 232 bp fragment from the synthetic human VJ was amplified by PCR (using primers SEQ ID NOs 313 and 314, Table 2) and used for ET cloning. Resulting colonies were screened by PCR (using primers SEQ ID NOs 315 and 316, Table 2) for loss of the FRT site and confirmed by sequencing.

The neomycin resistance gene of BAC179-215-huCk was replaced by ET cloning. A gentamycin resistance (pRep-Genta; Genebridges) gene was amplified by PCR with primers (SEQ ID NOs 317 and 318, Table 2) containing 50 bp sequences homologous to BAC 179-215-huCk. The forward primer additionally had a loxP site, an attB site and a PvuI restriction site. Resulting clones were selected with gentamycin and checked for correctness by restriction enzyme digests and sequencing.

Figure 8:
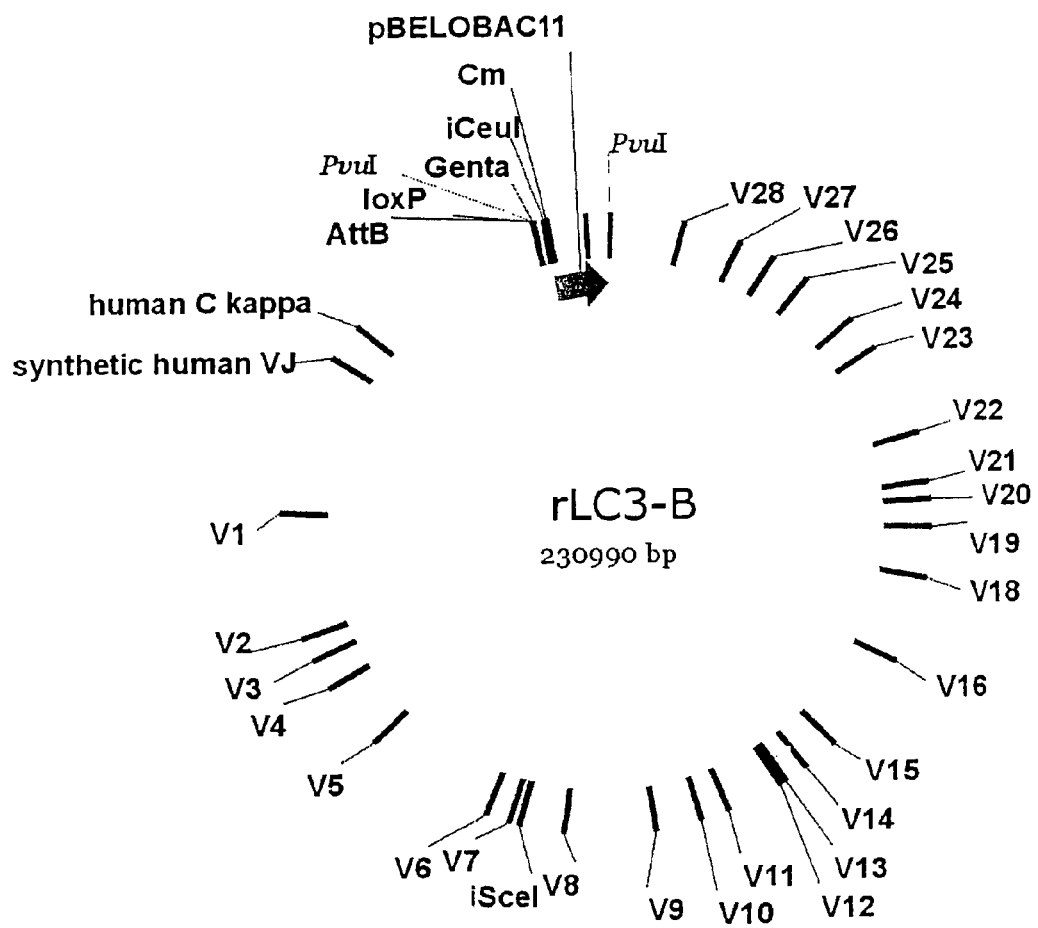
FIG. 8 shows a humanized rabbit light chain locus (rLC3-B) based on the rabbit K1 light chain locus. Rabbit Cκ1 was replaced with human Cκ. A human rearranged human VκJκ was inserted. The synthetic human VκJκ shares more than 80% sequence homology with rabbit Vκ elements

The resulting BAC (rLC3-B; FIG. 8) was used for the generation of transgenic animals.

EXAMPLE 6

Construction of a Humanized Rabbit Light Chain Locus Containing Multipe Human Vk Elements, Chicken Spacer Elements and a Rearranged Human VJ Screening of a rabbit genomic BAC libraries resulted in the identification of three BACs (215M22, 179L1 and 19O2; Gene Bank Accession Nos: AY495826, AY495827, and AY495828, respectively) containing rabbit light chain K1 gene segments. Rabbit Cκ☐0 was exchanged with human Cκ☐ allotype Km3 by ET cloning as described (E-Chiang Lee et al., *Genomics* 73, 56-65 (2001); Daiguan Yu et al., *PNAS* 97, 5978-5983 (2000); Muyrers et al., *Nucleic Acids Research* 27, 1555-1557 (1999); Zhang et al., *Nature Biotechnology* 18, 1314-1317 (2000)). Human Cκ (allotype Km3) was amplified by PCR with primers (SEQ ID Nos 301 and 302, Table 2) containing 50 bp sequences homologous to target sequences. Homology arms were designed based on the published sequence of rabbit germline kappa (b5; GenBank Accession No. K01363) and matched the intron-exon boundary of Cκ. The exchange of rabbit Cκ against the human Cκ in BAC 179L1 was verified by sequencing.

Figure 12C:
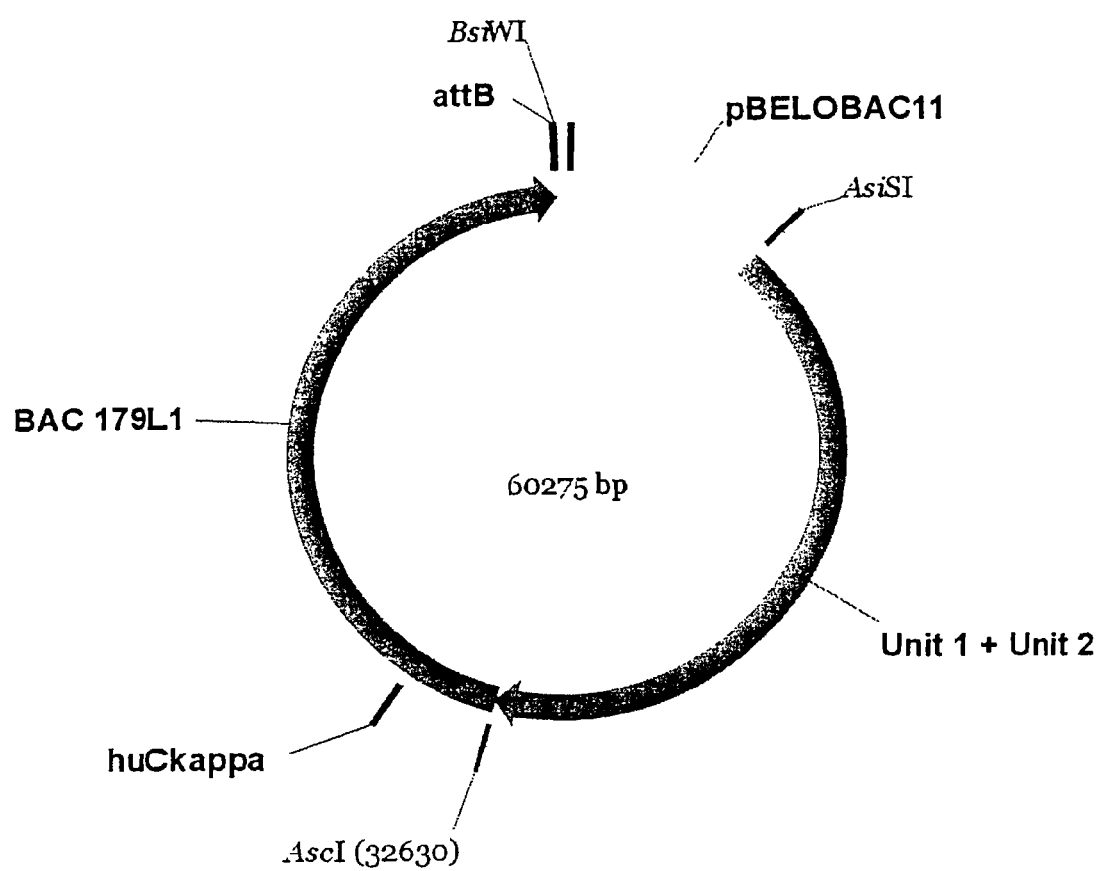

Two DNA fragments, Unit1 (12,235 bp, FIG. 12*a*, SEQ ID NO 187), containing 17 human V pseudogenes and 18 chicken spacer sequences and Unit 2 (13,283 bp, FIG. 12*b*, SEQ ID NO 188) containing one functional rearranged human kappa VJ gene with leader, 11 human V pseudogenes, 12 chicken spacer sequences and intron 1 and parts of intron 2 were synthesized chemically and cloned into vector pBR322.

Units 1 and 2 were digested with the restriction enzyme NgoMIV and AsiSI or NgoMIV and AscI respectively and ligated into pBELOBAC11 with a modified linker by three fragment ligation. The modified linker contained a BsiWI restriction site, a FRT5-site, a rpsL-Neo-cassette, a AscI site and a AsiSI-site. The linker fragment was amplified with High fidelity polymerase (Roche), primers CE_1_001_012904 (SEQ ID NO 319, Table 2) and CE_1_on005_013004 (SEQ ID NO 320, Table 2) and plasmid pRpsL-Neo (Genebridges) as template. Subsequently, the amplified product was ligated into BamHI and HindIII sites of pBELOBAC11. For ligation with Unit 1 and 2 the modified pBELOBAC11 was opened with AsiSI and AscI. Positive clones (pBELOBAC11 Unit1/2) were checked by restriction enzyme digests.

BAC 179L1 (GENBANK Acc. No. AY495827) was modified by insertion of two modified selection cassettes by ET cloning. Cassette 1 was a gentamycin resistance gene amplified with primers (SEQ ID Nos 321 and 322, Table 2) containing 50 bp sequences homologous to BAC 179L1 and an AscI site in the reverse primer. Cassette 2 was a rpsl-Neo selection cassette amplified with primers (SEQ ID Nos 323 and 324, Table 2) containing 50 bp sequences homologous to BAC 179L1 and an attB site, a FRT5 site and a BsiWI site in the forward primer.

The purified PCR products were transformed into *E. coli* cells carrying the BAC and plasmid pSC101 necessary for homologous recombination. After homologous recombination successful modification of the BAC was confirmed by restriction digest analyses, Southern Blot and sequencing.

Modified BAC 179L1 was cut with the restriction enzymes AscI and BsiWI. The fragment containing the human Cκ was purified and ligated with pBELOBAC11 Unit1/2 opened with the same restriction enzymes. Positive clones were checked by restriction enzyme digests. The final construct (FIG. 12c) is used for the generation of transgenic animals

EXAMPLE 7

Construction of a Humanized Rabbit Light Chain Locus Containing Multiple Human Vκ Elements, Chicken Spacers and an Unrearranged Human J Kappa Locus The construct described in example 6 was modified by ET cloning as follows: an. The rearranged functional VJ sequence was exchanged with a functional V1 flanked by a functional recombination signal sequence (RSS). The RSS was PCR amplified from BAC179L1 with a forward primer (SEQ ID NO 325, Table 2) containing a 50 bp sequence homologous to V1 of pBELOBAC11 Unit1/2 and a reverse primer (SEQ ID NO 326, Table 2) containing an AscI restriction enzyme site and homology to the gentamycin resistance gene. A gentamycin resistance gene was amplified with a forward primer (SEQ ID NO 327, Table 2) containing a sequence homologous to the reverse primer used for RSS amplification and a reverse primer (SEQ ID NO 328, Table 2) containing a 50 bp sequence homologous to pBELOBAC11 Unit1/2 and a BsiWI restriction enzyme site.

The RSS and the gentamycin resistance gene were combined by overlap extension PCR using the forward primer for RSS amplification and the reverse primer for Gentamycin resistance gene amplification. The resulting fragment was used to modify pBELOBAC11 Unit1/2 by ET cloning. Positive clones were selected with gentamycin and analyzed by restriction enzyme digests and sequencing.

BAC 179L1 with human Cκ was further modified by ET cloning. A kanamycin selection cassette was amplified with a primers (SEQ ID NO 329 and 330, Table 2) containing 50 bp sequences homologous to BAC 179L1. The reverse primer contained also an AscI restriction enzyme site and a FRT site. The PCR product was used for ET cloning. An ampicillin selection cassette was amplified with primers (SEQ ID Nos 331 and 332, Table 2) containing 50 bp sequences homologous to BAC 179L1. The forward primer contained also an attB site, an AsiSI restriction enzyme site and a FRT5 site The reverse primer contained a BsiWI restriction enzyme site and a FRT site. The PCR product was used for ET cloning. The human J region was amplified from human genomic DNA with primers (SEQ ID Nos 333 and 334, Table 2) containing 50 bp sequences homologous to BAC 179L1. The PCR product was used for ET cloning. The resulting clones were analyzed by restriction enzyme digest and sequencing.

A positive clone was cut with AscI and BsiWI. The resulting fragment was purified and ligated into the modified pBELOBAC11 Unit1/2 cut with the same enzymes. Positive clones were selected with ampicillin and analyzed by restriction enzyme digests and sequencing. Correct clones are used to generate transgenic animals.

EXAMPLE 8

Construction of a Humanized Rabbit Light Chain Locus Containing Multiple Human Vk Elements Screening of a rabbit genomic BAC libraries resulted in the identification of three BACs (215M22, 179L1 and 196O2; Gene Bank Accession Nos: AY495826, AY495827, and AY495828, respectively) containing rabbit light chain K1 gene segments. Rabbit Cκ1 was exchanged with human Cκ□ allotype Km3 by ET cloning as described (E-Chiang Lee et al., *Genomics* 73, 56-65 (2001); Daiguan Yu et al., *PNAS* 97, 5978-5983 (2000); Muyrers et al., *Nucleic Acids Research* 27, 1555-1557 (1999); Zhang et al., *Nature Biotechnology* 18, 1314-1317 (2000)). Human Cκ (allotype Km3) was amplified by PCR with primers (SEQ ID NOs 301 and 302, Table 2) containing 50 bp sequences homologous to target sequences. Homology arms were designed based on the published sequence of rabbit germline kappa (b5; GenBank Accession No. K01363) and matched the intron-exon boundary of Cκ. The exchange of rabbit Cκ against the human Cκ in BAC 179L1 was verified by sequencing.

Human Vκ elements of the Vκ1 family (O2, L8, L4, A30, L11, L1, L5, L15, O8, L19, L12, A20, O4, L14, L23, L9, A4, L24, O6, L22, A9, A25, A15, O9) were amplified by PCR using primers (SEQ ID NOs 335-382, Table 2) and human genomic DNA as a template.

Amplification products were analysed by gel-electrophoresis, gel purified using GENECLEAN (Q-Biogen), subcloned into the Zero-Blunt TOPO™ vectors (Invitrogen) and sequenced. A rearranged human Vκ (O2) Jκ (J4) element was produced by PCR amplification, subcloned and sequenced. To combine human Vκ elements with rabbit spacers, human Vκ elements were amplified by PCR with primers (SEQ ID Nos 383-430, Table 2) using plasmid DNA as a template. Primers contained AscI or MluI sites.

Rabbit spacer sequences are amplified by PCR using primers SEQ ID NOs 431-450 (Table 2). BACs 179L1 and 215M22 are digested with SpeI, NheI, AclI, SfoI, MluI, and SalI/XhoI. Fragments are gel purified and used as amplification templates.

The spacer sequence located at the 5-end is amplified by an upstream oligonucleotide containing a FRT and an attB site. PCR products are gel purified using the GENECLEAN kit and subcloned into XL-PCR-TOPO™ (Invitrogen) according to the manufacturer's instructions.

Human Vk elements and rabbit spacer sequences were cloned into pGem (Promega) modified as described in Example 4.

Figure 7:
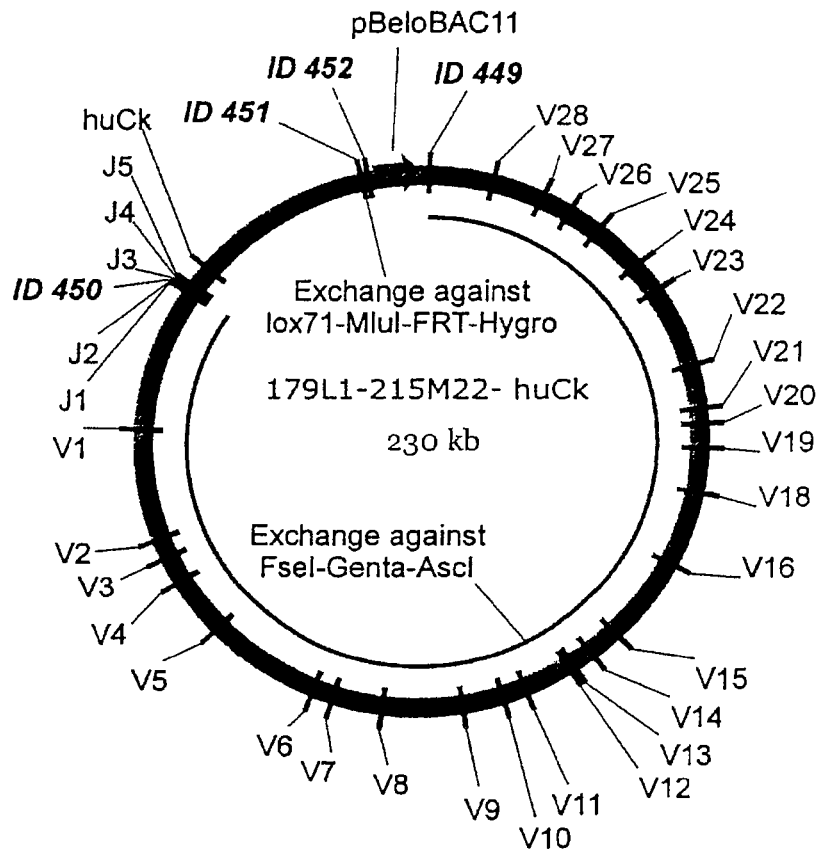
FIGS. 7 (a) and (b): Insertion of two cassettes by homologous recombination using the redεβγ-system.
Figure 7:
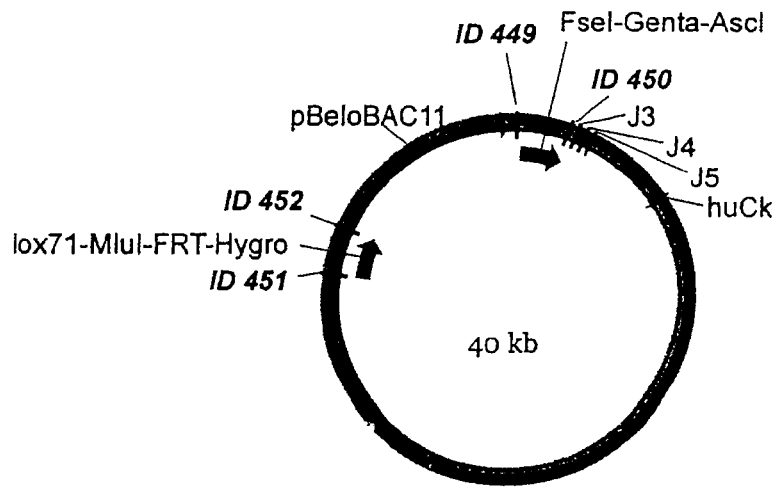

Human V kappa and the modified pGEM.genta vector are digested with AscI and MluI and ligated. Similarly, rabbit spacer sequences are cloned into pGEM.neo. Subsequently, pGem.neo.Vκ is cut with FseI and AscI and ligated with a purified insert of pGem.genta.spacer excised with FseI and MluI. Ligation of AscI and MluI complementary ends destroys the restriction enzyme site and allows repeated use of AscI and MluI for the construction of a Vκ locus comprising several Vκ and spacer elements. The final construct, consisting of fragments of a humanized BAC 179L1 and 215M22 and a humanized Vκ region is built in pBeloBAC. BAC 179L1 and 215M22 were modified and combined. Subsequently, BAC 179L1-215M22-huCk was further modified by ET cloning. Two cassettes containing restriction enzyme site, selection markers, and additional functional sites were inserted into the vector by ET-cloning as shown in FIG. 7. Primers (SEQ ID NOs 451-454) used for the amplification of the cassettes are listed in Table 2.

To built the final construct, units consisting of human V elements, rabbit spacer elements and a resistance marker are excised out of pGEM with FseI and MluI and ligated with BAC 179L1-215M22 digested with FseI and AscI. Subsequently, the resistance marker is replaced with a new insert consisting of human V elements, rabbit spacer elements and another resistance marker. After several repeats the final construct will consist of many Vk segments (L8, L4, A30, L11, L1, L5, L15, O8, L19, L12, A20, O4, L14, L23, L9, A4, L24, O6, L22, A9, A25, A15, O9) separated by rabbit spacer sequences. The humanized light chain locus is used for the generation of transgenic animals.

EXAMPLE 9

Construction of a Humanized Heavy Chain Locus with Chicken Heavy Chain Locus Spacer Sequences A synthetic humanized heavy chain locus containing a rabbit D region, a human J region, human Cμ, human Cγ, rabbit Cα4, the rabbit 3'α enhancer and human VH elements (including promotor and nonamer/heptamer sequences) separated by chicken spacer sequences is constructed.

Modified rabbit BAC 27N5 (see "Example 2) was further modified by ET cloning. The construct contained a humanized Cμ and Cγ and two unique restriction sites, BsiWI and AsiSI downstream of the α-4 membrane exon. DNA is amplified with oligonucleotides SEQ ID Nos 455 and 456 (Table 2).

Fosmid Fos15B is digested with NheI and the resulting 13 kb fragment containing the 3'α enhancer is subcloned into a cloning vector in such a way that the insert is flanked by BsiWI and AsiSI sites. Subsequently, the insert is excised with BsiWI and AsiSI and ligated with the modified BAC 27N5 to form BAC 27N5Fos.

The rabbit J region in BAC219D23 was exchanged with the corresponding human J region by ET cloning. The human J region was amplified by PCR using primers SEQ ID NOs 457 and 458 (Table 2).

Unique restriction enzyme sites are inserted in BAC219D23 upstream of the D region (A) and upstream of Cμ(B)☐. In BAC 27N5Fos restriction site A is inserted upstream of the linker region and B is inserted in sequences homologous to BAC219D23. Following digestion with enzymes A and B, the fragment containing human J and rabbit D regions is isolated and ligated with BAC 27N5Fos to create BAC 219D23/27N5Fos.

Chicken heavy chain spacer sequences are amplified from chicken genomic DNA by PCR using primers (SEQ ID NOS 459 and 460, Table 2) specific for chicken heavy chain V pseudogenes (Mansikka et al., *J Immunol* 145(11), 3601-3609 (1990), Reynaud et al., *Cell* 59(1), 171-183 (1989)). Alternatively, spacer sequences are synthesized chemically.

The PCR products are gel purified, cloned into pTOPO (Invitrogen) and sequenced.

Human heavy chain variable elements are amplified by PCR using primers designed according to published sequences in GENBANK (eg Acc. No. NG_001019) or synthesized chemically. The human V elements contain the human promoter region, the human leader sequence, the human intron between leader and V-coding region, the human V-coding region and the human recombination signal sequence. The amplified or synthesized fragments are flanked by specific restriction endonuclease recognition. Chicken spacer sequences and human V elements are combined in one or several large DNA fragment comprising a humanized immunoglobulin locus. The construct is used to generate transgenic animals.

EXAMPLE 10

Construction of a Humanized Immunoglobulin Locus Containing Human V Elements and Non-Human Spacer Sequences (without Promoter Region and RSS)

Figure 10A:
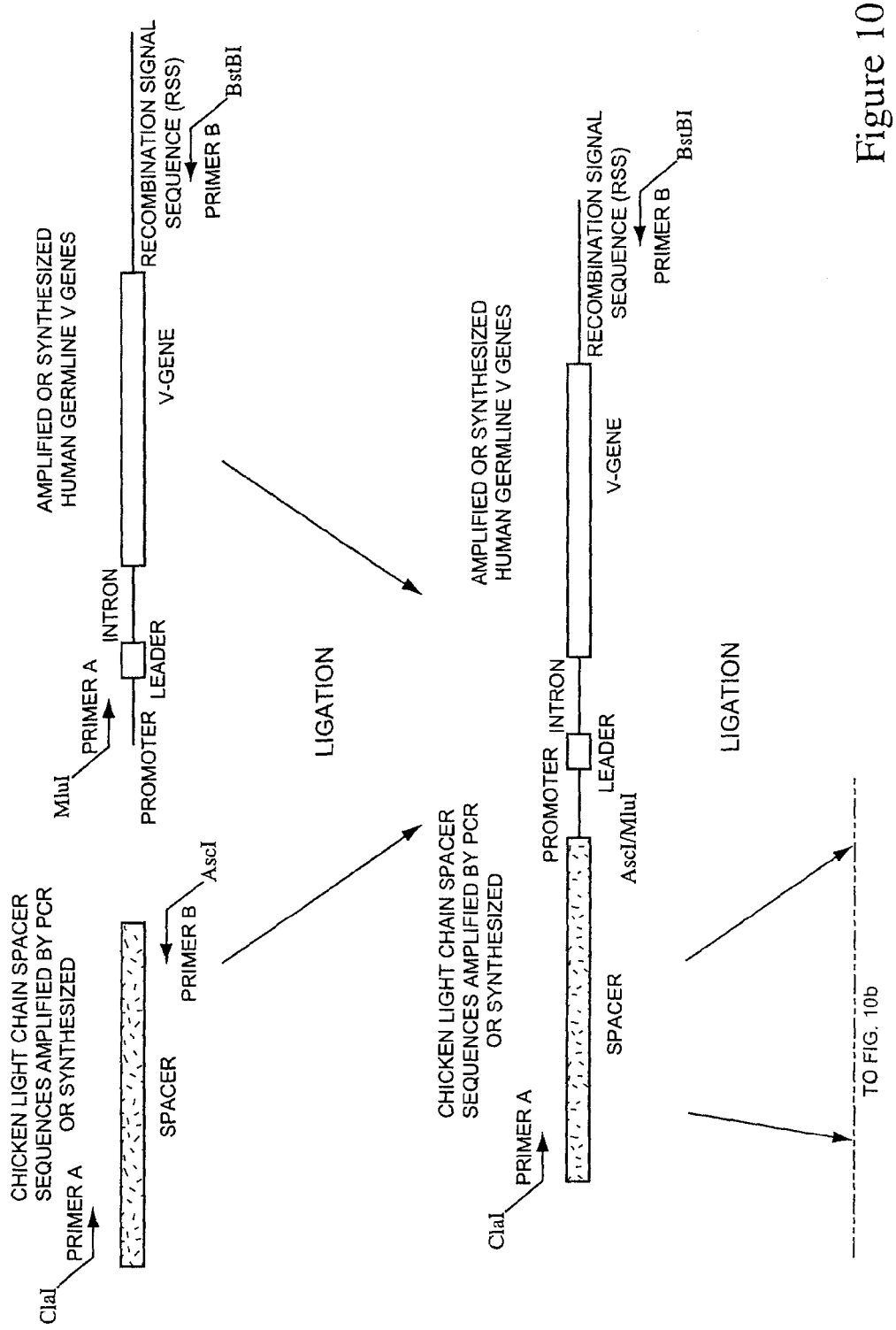
FIGS. 10a and 10b illustrate an outline showing the construction of a humanized immunoglobulin locus using chicken immunoglobulin spacer sequences and human V elements.
Figure 10B:
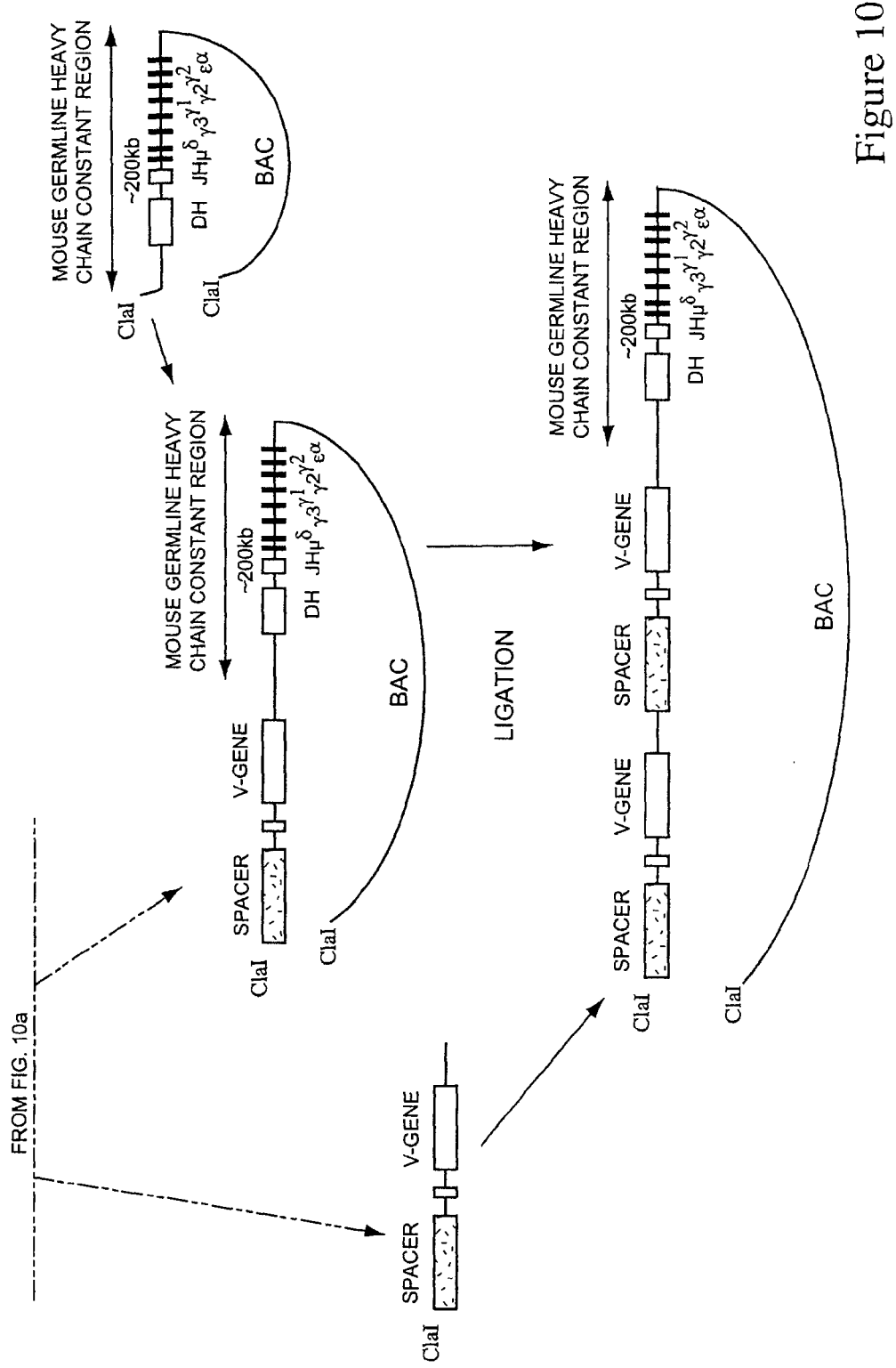

A BAC library generated with non-human genomic DNA is screened with probes specific for immunoglobulin and BAC clones containing heavy and light chain immunoglobulin C, J and D regions are identified. The BAC clones are modified to contain restriction enzyme sites. Human heavy and light chain variable elements are amplified by PCR using primers designed according to published sequences in GenBank (eg., Acc. No. NG_001019). Sequences are amplified from genomic DNA or synthesized chemically. The human V elements contain the human promoter region, the human leader sequence, the human intron between leader and V-coding region, the human V-coding region and the human recombination signal sequence (RSS). The amplified or synthesized fragments have specific restriction endonuclease recognition sites at the ends. The non-human spacer sequences are amplified by PCR or synthesized chemically. Non-human spacer sequences and human V elements are combined in one or several large DNA fragment comprising a humanized immunoglobulin locus. The construct is used to generate transgenic animals. An example for the construction of a humanized V region using chicken spacer sequences is shown in FIG. 10.

EXAMPLE 11

Figure 11A:
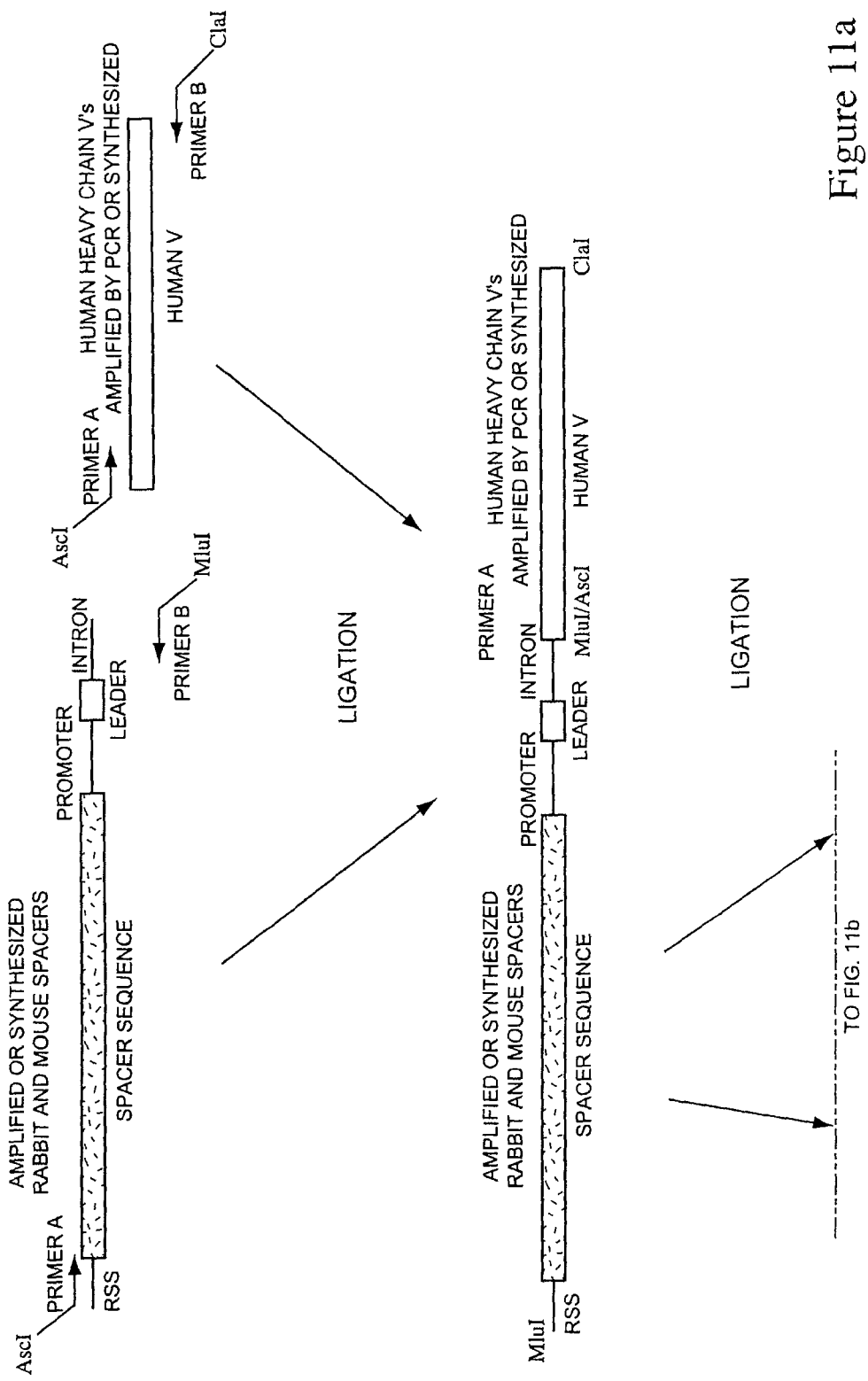
FIGS. 11a and 11b illustrate an outline showing the construction of a humanized immunoglobulin locus using mouse or rabbit immunoglobulin spacer sequences and human V elements.
Figure 11B:
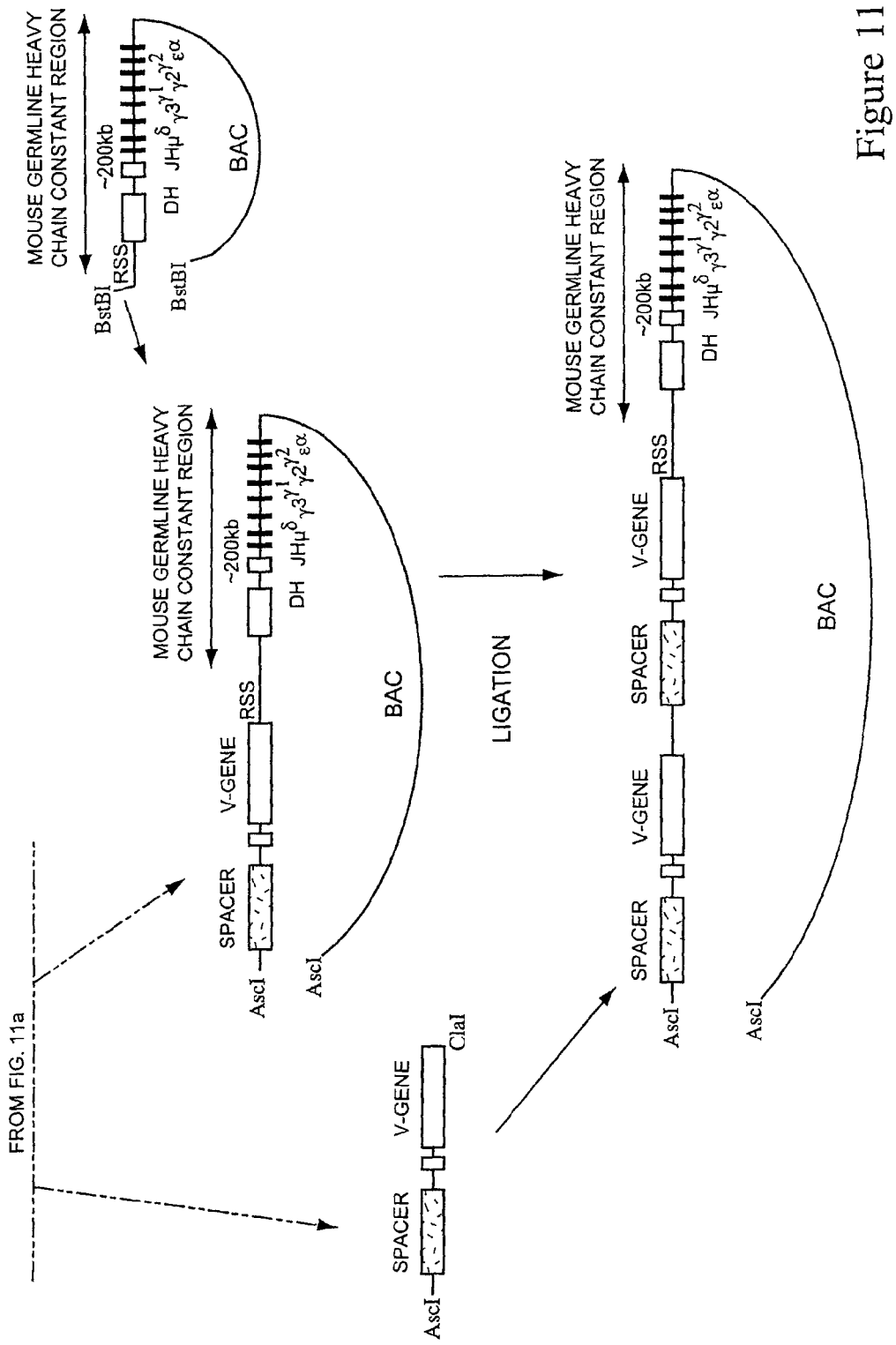

Construction of a Humanized Immunoglobulin Locus Containing Human V Elements and Non-Human Spacer Sequences A BAC library generated with non-human genomic DNA is screened with probes specific for immunoglobulin and BAC clones containing heavy and light chain immunoglobulin C, J and D regions are identified. The BAC clones are modified to contain restriction enzyme sites. Human heavy and light chain variable elements are amplified by PCR using primers designed according to published sequences in GenBank (eg., Acc No. NG_001019). Sequences are amplified from genomic DNA or synthesized chemically. The human V elements contain the human V coding region. Non-human spacer sequences are amplified by PCR or synthesized chemically and contain a recombination signal sequence, a spacer sequence, a promoter region, a leader sequence and the intron between leader and V coding region. Such non-human spacer sequences are combined with human V elements in one or several large DNA fragments and used for the generation of transgenic animals. An example for the construction of a humanized V region using mouse or rabbit spacer sequences is shown in FIG. 11.

EXAMPLE 12

Transgenic Rabbits Expressing Humanized Immunoglobulins

Transgenic rabbits were generated as described by Fan et al. (*Pathol. Int.* 49: 583-594, 1999). Briefly, female rabbits are superovulated using standard methods and mated with male rabbits. Pronuclear-stage zygotes are collected from oviduct and placed in an appropriate medium such as Dulbecco's phosphate buffered saline supplemented with 20% fetal bovine serum. BAC containing humanized immunoglobulin loci were microinjected into the male pronucleus with the aid of a pair of manipulators. Morphological surviving zygotes were transferred to the oviducts of pseudopregnant rabbits. Pseudopregnancy was induced by the injection of human chorionic gonadotrophin (hCG). Following injection of a humanized light chain construct into 4645 pronuclei of fertilized oocytes, 4043 oocytes were transferred into 132 recipients. In total, 253 live offspring were born, 11 of which were transgenic. Expression of human kappa light chain was detected by ELISA using human-kappa light chain specific reagents (for example, mouse anti-human Kappa, Southern Biotech, 9220-01; goat anti-human Kappa, Southern Biotech 2063-08).

A humanized heavy chain construct was injected into 4083 pronuclei of fertilized oocytes. 3485 oocytes were transferred into 119 recipients which delivered 433 offspring. Analysis by PCR and FISH revealed that 20 of these animals were transgenic. Humanized heavy chain in the blood of founder animals was detected by ELISA using antibodies specific for human IgM/IgG (for example, rabbit anti-human IgM, Rockland 609-4131; rabbit anti-human IgM, Rockland 609-4631; rabbit anti-human IgG, Pierce 31142, rabbit anti-human IgG, Southern Biotech 6145-08; rabbit anti-human IgG, Pierce 31784).

Sandwich-type ELISAs detecting humanized κ, μ and γ chains were performed using standard procedures. Briefly, microtiter plates were coated with capture antibody and incubated with diluted serum samples. Bound human immunoglobulin was detected using a secondary labeled antibody and peroxidase-streptavidin-conjugate (Sigma, S2438).

Double transgenic animals expressing both humanized heavy and light immunoglobulin chains were generated by breeding of founder animals.

EXAMPLE 13

Transgenic Mice Expressing Humanized Immunoglobulins

Transgenic mice were generated as described by Nagy et al. (*Manipulating the Mouse Embryo: A Laboratory Manual*; Cold Spring Harbor Laboratory Press, New York, 2003). Briefly, female mice were superovulated using standard methods and mated with male mice. Pronuclear-stage zygotes were collected from oviduct and placed in a suitable medium such as M2 medium. BAC containing humanized immunoglobulin loci were microinjected into the male pronucleus with the aid of a pair of manipulators. Morphologically surviving zygotes were transferred to the oviducts of pseudopregnant female mice. Pseudopregnancy was induced by mating with sterile males. Following injection of a humanized light chain construct into 1325 pronuclei of fertilized oocytes, 787 oocytes were transferred into 29 recipients. In total, 55 live offspring were born, 11 of which were transgenic.

A humanized heavy chain construct was injected into 1050 pronuclei of fertilized oocytes. 650 oocytes were transferred into 25 recipients which delivered 64 live offspring. Analysis by PCR revealed that 19 of these animals were transgenic.

Double transgenic animals expressing both humanized heavy and light immunoglobulin chains are generated by breeding of founder animals. Expression of humanized κ, μ and γ chains was detected by ELISAs using standard procedures. Briefly, microtiter plates were coated with capture antibody and incubated with diluted serum samples. Bound human immunoglobulin was detected using a secondary labeled antibody and peroxidase-streptavidin-conjugate (Sigma, S2438).

All references cited throughout the specification are hereby expressly incorporated by reference. While the invention is illustrated by reference to certain embodiments, it is not so limited. One skilled in the art will recognize that various modifications and variations are possible without diverting from the essence of the invention. All such modifications and variations are specifically included within the scope herein.

TABLE 1

| ID | BAC | Accession# | Start | Finish | Description |
|---|---|---|---|---|---|
| 1 | 38A2 | AY386694 | 1 | 2137 | Spacer 5' start-V34 |
| 2 | 38A2 | AY386694 | 2433 | 9504 | Spacer V34-V33 |
| 3 | 38A2 | AY386694 | 9798 | 19384 | Spacer V33-V32 |
| 4 | 38A2 | AY386694 | 19690 | 35164 | Spacer V32-V31 |
| 5 | 38A2 | AY386694 | 35447 | 47669 | Spacer V31-V30 |
| 6 | 38A2 | AY386694 | 47973 | 52521 | Spacer V30-V29 |
| 7 | 38A2 | AY386694 | 52819 | 61798 | Spacer V29-V28 |
| 8 | 38A2 | AY386694 | 62100 | 74264 | Spacer V28-V27 |
| 9 | 38A2 | AY386694 | 74566 | 79145 | Spacer V27-V26 |
| 10 | 38A2 | AY386694 | 79449 | 84800 | Spacer V26-V25 |
| 11 | 38A2 | AY386694 | 85103 | 95717 | Spacer V25-V24 |
| 12 | 38A2 | AY386694 | 96009 | 102226 | Spacer V24-V26 |
| 13 | 38A2 | AY386694 | 102504 | 105307 | Spacer V23-V22 |
| 14 | 38A2 | AY386694 | 105603 | 107583 | Spacer V22-V24 |
| 15 | 38A2 | AY386694 | 107769 | 118033 | Spacer V24-V20 |
| 16 | 38A2 | AY386694 | 118334 | 125546 | Spacer V20-V19 |
| 17 | 38A2 | AY386694 | 125849 | 128059 | Spacer V19-3' end |
| 18 | 225P18 | AY386697 | 1 | 4333 | Spacer 5' start-V18 |
| 19 | 225P18 | AY386697 | 4629 | 9255 | Spacer V18-V17 |
| 20 | 225P18 | AY386697 | 9561 | 15841 | Spacer V17-V16 |
| 21 | 225P18 | AY386697 | 16135 | 22502 | Spacer V16-V15 |
| 22 | 225P18 | AY386697 | 22794 | 32821 | Spacer V15-V14 |
| 23 | 225P18 | AY386697 | 33118 | 37738 | Spacer V14-V13 |
| 24 | 225P18 | AY386697 | 38044 | 44571 | Spacer V13-V12 |
| 25 | 225P18 | AY386697 | 44865 | 49447 | Spacer V12-V11 |
| 26 | 225P18 | AY386697 | 49745 | 56909 | Spacer V11-V10 |
| 27 | 225P18 | AY386697 | 57205 | 63678 | Spacer V10-V9 |
| 28 | 225P18 | AY386697 | 63977 | 71204 | Spacer V9-V8 |
| 29 | 225P18 | AY386697 | 71507 | 76261 | Spacer V8-V7 |
| 30 | 225P18 | AY386697 | 76560 | 79012 | Spacer V7-V6 |
| 31 | 225P18 | AY386697 | 79308 | 83467 | Spacer V6-V5 |
| 32 | 225P18 | AY386697 | 83768 | 88013 | Spacer V5-V4 |
| 33 | 225P18 | AY386697 | 88314 | 91233 | Spacer V4-V3 |
| 34 | 225P18 | AY386697 | 91531 | 95929 | Spacer V3-V2 |
| 35 | 225P18 | AY386697 | 96233 | 100963 | Spacer V2-V1 |
| 36 | 225P18 | AY386697 | 101262 | 133721 | Spacer V1-D3 |
| 37 | 225P18 | AY386697 | 133752 | 135212 | Spacer D3-D1a |
| 38 | 225P18 | AY386697 | 135237 | 136922 | Spacer D1a-D4 |
| 39 | 225P18 | AY386697 | 136947 | 139446 | Spacer D4-3' end |
| 40 | 219D23 | AY386695 | 8151 | 40612 | Spacer V1-D3 |
| 41 | 219D23 | AY386695 | 40643 | 42102 | Spacer D3-D1a |
| 42 | 219D23 | AY386695 | 42127 | 43812 | Spacer D4-D1b |
| 43 | 219D23 | AY386695 | 43837 | 48553 | Spacer D1b-D6 |
| 44 | 219D23 | AY386695 | 48577 | 48753 | Spacer D6-D8 |
| 45 | 219D23 | AY386695 | 48769 | 51181 | Spacer D8-D2x |
| 46 | 219D23 | AY386695 | 51213 | 55826 | Spacer D1c-Df |
| 47 | 219D23 | AY386695 | 55852 | 61112 | Spacer Df-D1d |
| 48 | 219D23 | AY386695 | 61237 | 62445 | Spacer D1d-D5 |
| 49 | 219D23 | AY386695 | 62471 | 97024 | Spacer D5-DQ52 |
| 50 | 219D23 | AY386695 | 97036 | 97831 | Spacer DQ52-J1 |
| 51 | 219D23 | AY386695 | 97871 | 98090 | Spacer J1-J2 |
| 52 | 219D23 | AY386695 | 98140 | 98430 | Spacer J2-J3 |
| 53 | 219D23 | AY386695 | 98483 | 98642 | Spacer J3-J4 |
| 54 | 219D23 | AY386695 | 98690 | 98981 | Spacer J4-J5 |
| 55 | 219D23 | AY386695 | 99032 | 99550 | Spacer J5-J6 |
| 56 | 219D23 | AY386695 | 99604 | 106867 | Spacer J6-IgM exon1 |
| 57 | 219D23 | AY386695 | 107185 | 107290 | Spacer IgM exon1-exon2 |
| 58 | 219D23 | AY386695 | 107635 | 107863 | Spacer IgM exon2-exon3 |
| 59 | 219D23 | AY386695 | 108181 | 108268 | Spacer IgM exon3-exon4 |
| 60 | 219D23 | AY386695 | 108664 | 110499 | Spacer IgM exon4-exonM1 |
| 61 | 219D23 | AY386695 | 110615 | 110741 | Spacer exonM1-exonM2 |
| 62 | 219D23 | AY386695 | 108664 | 137302 | Spacer IgM exon4-3' end |
| 63 | 27N5 | AY386696 | 5099 | 55582 | Spacer IgM exon4-IgG exon1 |
| 64 | 27N5 | AY386696 | 55867 | 56071 | Spacer IgG exon1-exon2 |
| 65 | 27N5 | AY386696 | 56104 | 56201 | Spacer IgG exon2-exon3 |
| 66 | 27N5 | AY386696 | 56531 | 56623 | Spacer IgG exon3-exon4 |
| 67 | 27N5 | AY386696 | 56946 | 58984 | Spacer IgG exon4-exonM1 |

TABLE 1-continued

| ID | BAC | Accession# | Start | Finish | Description |
|---|---|---|---|---|---|
| 68 | 27N5 | AY386696 | 56946 | 59205 | Spacer IgG exon4-exonM2 |
| 69 | 27N5 | AY386696 | 56946 | 69246 | Spacer IgG exon4-IgE exon1 |
| 70 | 27N5 | AY386696 | 69546 | 69719 | Spacer IgE exon1-exon2 |
| 71 | 27N5 | AY386696 | 70037 | 70132 | Spacer IgE exon2-exon3 |
| 72 | 27N5 | AY386696 | 70453 | 70532 | Spacer IgE exon3-exon4 |
| 73 | 27N5 | AY386696 | 70873 | 73061 | Spacer IgE exon4-exonM1 |
| 74 | 27N5 | AY386696 | 70873 | 73292 | Spacer IgE exon4-exonM2 |
| 75 | 27N5 | AY386696 | 70873 | 86059 | Spacer IgE exon4-IgA4 exon1 |
| 76 | 27N5 | AY386696 | 86362 | 86498 | Spacer IgA4 exon1-exon2 |
| 77 | 27N5 | AY386696 | 86876 | 87059 | Spacer IgA4 exon2-exon3 |
| 78 | 27N5 | AY386696 | 87450 | 89577 | Spacer IgA4 exon3-exonM |
| 79 | 27N5 | AY386696 | 87450 | 103798 | Spacer IgA4 exon3-IgA5b exon1 |
| 80 | 27N5 | AY386696 | 104101 | 104231 | Spacer IgA5b exon1-exon2 |
| 81 | 27N5 | AY386696 | 104609 | 104787 | Spacer IgA5b exon2-exon3 |
| 82 | 27N5 | AY386696 | 105182 | 107227 | Spacer IgA5b exon3-exonM |
| 83 | 27N5 | AY386696 | 105182 | 112077 | Spacer IgA5b exon3-exonM |
| 84 | 27N5 | AY386696 | 105182 | 119223 | Spacer IgA5b exon3-IgA1 exon1 |
| 85 | 27N5 | AY386696 | 119511 | 119644 | Spacer IgA1 exon1-exon2 |
| 86 | 27N5 | AY386696 | 119984 | 120162 | Spacer IgA1 exon2-exon3 |
| 87 | 27N5 | AY386696 | 120557 | 122823 | Spacer IgA1 exon3-exonM |
| 88 | 27N5 | AY386696 | 120557 | 127750 | Spacer IgA1 exon3-exonM* |
| 89 | 27N5 | AY386696 | 120557 | 135838 | Spacer IgA1 exon3-IgA2 exon1 |
| 90 | 27N5 | AY386696 | 136138 | 136274 | Spacer IgA2 exon1-exon2 |
| 91 | 27N5 | AY386696 | 136652 | 136831 | Spacer IgA2 exon2-exon3 |
| 92 | 27N5 | AY386696 | 137229 | 139433 | Spacer IgA2 exon3-exonM |
| 93 | 27N5 | AY386696 | 137229 | 146676 | Spacer IgA2 exon3-3' end |
| 94 | Fos15B | AY386698 | 1 | 828 | Spacer 5' start-IgA exonM |
| 95 | Fos15B | AY386698 | 1043 | 3596 | Spacer IgA exonM-end contig1 |
| 96 | Fos15B | AY386698 | 1 | 3596 | Spacer 5' start-end contig1 |
| 97 | Fos15B | AY386698 | 7404 | 7541 | Spacer IgA exon1-exon2 |
| 98 | Fos15B | AY386698 | 7908 | 8086 | Spacer IgA exon2-exon3 |
| 99 | Fos15B | AY386698 | 8481 | 10538 | Spacer IgA exon3-exonM |
| 100 | Fos15B | AY386698 | 8481 | 13140 | Spacer IgA exon3-end contig2 |
| 101 | Fos15B | AY386698 | 8481 | 15871 | Spacer IgA exon3-1,2 hs 3' enh |
| 102 | Fos15B | AY386698 | 8481 | 21447 | Spacer IgA exon3-4hs enh |
| 103 | Fos15B | AY386698 | 21484 | 33297 | Spacer 4hs enh-end contig4 |
| 104 | Fos15B | AY386698 | 16633 | 33297 | Spacer 1,2hs 3' enh-end contig4 |
| 105 | 179L1 | AY495827 | 1 | 124285 | Spacer 5' end-enh |
| 106 | 179L1 | AY495827 | 125411 | 131350 | Enhancer-C□ |
| 107 | 179L1 | AY495827 | 131664 | 134637 | Spacer C□-J5 |
| 108 | 179L1 | AY495827 | 134684 | 134915 | Spacer J5-J4 |
| 109 | 179L1 | AY495827 | 134952 | 135196 | Spacer J4-J3 |
| 110 | 179L1 | AY495827 | 135241 | 135485 | Spacer J3-J2 |
| 111 | 179L1 | AY495827 | 135525 | 135863 | Spacer J2-J1 |
| 112 | 179L1 | AY495827 | 135897 | 155257 | Spacer J1-V1 |
| 113 | 179L1 | AY495827 | 155572 | 170621 | Spacer V1-V2 |
| 114 | 179L1 | AY495827 | 170936 | 173443 | Spacer V2-V3 |
| 115 | 179L1 | AY495827 | 173752 | 177227 | Spacer V3-V4 |
| 116 | 179L1 | AY495827 | 177536 | 185356 | Spacer V4-V5 |
| 117 | 179L1 | AY495827 | 185664 | 200758 | Spacer V5-V6 |
| 118 | 179L1 | AY495827 | 201064 | 203580 | Spacer V6-V7 |
| 119 | 179L1 | AY495827 | 203886 | 205144 | Spacer V7-3' end |
| 120 | 215M22 | AY495826 | 1 | 12829 | Spacer 5' end-V6 |
| 121 | 215M22 | AY495826 | 13136 | 15653 | Spacer V6-V7 |
| 122 | 215M22 | AY495826 | 15957 | 22241 | Spacer V7-V8 |
| 123 | 215M22 | AY495826 | 22551 | 32876 | Spacer V8-V9 |
| 124 | 215M22 | AY495826 | 33188 | 38276 | Spacer V9-V10 |
| 125 | 215M22 | AY495826 | 38582 | 41476 | Spacer V10-V11 |
| 126 | 215M22 | AY495826 | 41780 | 47827 | Spacer V11-V12 |
| 127 | 215M22 | AY495826 | 48133 | 48547 | Spacer V12-V13 |
| 128 | 215M22 | AY495826 | 48841 | 51408 | Spacer V13-V14 |
| 129 | 215M22 | AY495826 | 51638 | 55438 | Spacer V14-V15 |
| 130 | 215M22 | AY495826 | 55745 | 67437 | Spacer V15-V16 |
| 131 | 215M22 | AY495826 | 67743 | 77805 | Spacer V16-V17 |
| 132 | 215M22 | AY495826 | 78120 | 80628 | Spacer V17-V18 |
| 133 | 215M22 | AY495826 | 80937 | 84009 | Spacer V18-V19 |
| 134 | 215M22 | AY495826 | 84315 | 87339 | Spacer V19-V20 |
| 135 | 215M22 | AY495826 | 87648 | 89399 | Spacer V20-V21 |
| 136 | 215M22 | AY495826 | 89711 | 95414 | Spacer V21-V22 |
| 137 | 215M22 | AY495826 | 95720 | 106650 | Spacer V22-V23 |
| 138 | 215M22 | AY495826 | 106956 | 110940 | Spacer V23-V24 |
| 139 | 215M22 | AY495826 | 111246 | 117877 | Spacer V24-V25 |
| 140 | 215M22 | AY495826 | 118183 | 122396 | Spacer V25-V26 |
| 141 | 215M22 | AY495826 | 122706 | 126496 | Spacer V26-V27 |
| 142 | 215M22 | AY495826 | 126802 | 133358 | Spacer V27-V28 |
| 143 | 196O2 | AY495828 | 37134 | 48826 | Spacer V15-V16 |
| 144 | 196O2 | AY495828 | 49032 | 59195 | Spacer V16-V17 |
| 145 | 196O2 | AY495828 | 115057 | 125885 | Spacer V28-V29 |
| 146 | 196O2 | AY495828 | 126195 | 130012 | Spacer V29-V30 |
| 147 | 196O2 | AY495828 | 130318 | 136966 | Spacer V30-V31 |
| 148 | 196O2 | AY495828 | 137272 | 144512 | Spacer V31-V32 |
| 149 | 196O2 | AY495828 | 144819 | 148617 | Spacer V32-V33 |
| 150 | 196O2 | AY495828 | 148923 | 155402 | Spacer V33-V34 |
| 151 | 196O2 | AY495828 | 155714 | 171415 | Spacer V34-V35 |
| 152 | 196O2 | AY495828 | 171572 | 177676 | Spacer V35-V36 |
| 153 | 196O2 | AY495828 | 177979 | 178083 | Spacer V36-3' end |
| 154 | CLC* | NA | 1 | 443 | Spacer 5' end-pV28** |
| 155 | CLC* | NA | 486 | 1203 | Spacer pV28-Pv27** |
| 156 | CLC* | NA | 1528 | 1635 | Spacer pV27-pV26** |
| 157 | CLC* | NA | 1818 | 2242 | Spacer pV26-pV25** |
| 158 | CLC* | NA | 2585 | 2676 | Spacer pV25-pV24** |
| 159 | CLC* | NA | 2781 | 3327 | Spacer pV24-pV23** |
| 160 | CLC* | NA | 3464 | 3659 | Spacer pV23-pV22** |
| 161 | CLC* | NA | 3985 | 4241 | Spacer pV22-pV21** |
| 162 | CLC* | NA | 4578 | 4994 | Spacer pV21-pV20** |
| 163 | CLC* | NA | 5366 | 5425 | Spacer pV20-pV19** |
| 164 | CLC* | NA | 5749 | 5842 | Spacer pV19-pV18** |
| 165 | CLC* | NA | 6034 | 7043 | Spacer pV18-pV17** |
| 166 | CLC* | NA | 7266 | 7493 | Spacer pV17-pV16** |
| 167 | CLC* | NA | 7625 | 7625 | Spacer pV16-pV15** |
| 168 | CLC* | NA | 7988 | 8758 | Spacer pV15-pV14** |
| 169 | CLC* | NA | 9100 | 9410 | Spacer pV14-pV13** |

TABLE 1-continued

| ID | BAC | Accession# | Start | Finish | Description |
|---|---|---|---|---|---|
| 170 | CLC* | NA | 9787 | 10057 | Spacer pV13-pV12** |
| 171 | CLC* | NA | 10441 | 11022 | Spacer pV12-pV11** |
| 172 | CLC* | NA | 11380 | 11911 | Spacer pV11-pV10** |
| 173 | CLC* | NA | 12162 | 12349 | Spacer pV10-pV9** |
| 174 | CLC* | NA | 12691 | 13357 | Spacer pV9-pV8** |
| 175 | CLC* | NA | 13708 | 13882 | Spacer pV8-pV7** |
| 176 | CLC* | NA | 14229 | 14406 | Spacer pV7-pV6** |
| 177 | CLC* | NA | 14599 | 15338 | Spacer pV6-pV5** |
| 178 | CLC* | NA | 15613 | 16578 | Spacer pV5-pV4** |
| 179 | CLC* | NA | 16916 | 18219 | Spacer pV4-pV3** |
| 180 | CLC* | NA | 18439 | 18879 | Spacer pV3-pV2** |
| 181 | CLC* | NA | 19248 | 19343 | Spacer pV2-pV1** |
| 182 | CLC* | NA | 19609 | 22208 | Spacer pV1-V** |
| 183 | CLC* | NA | 22506 | 24313 | Spacer V-J |
| 184 | CLC* | NA | 24350 | 26088 | Spacer J-C□ |
| 185 | CLC* | NA | 26402 | 36259 | Spacer C-3' end |

*CLC—Chicken light chain locus SEQ ID 184, FIG. 9
**pV—pseudo V gene (not functional)
Comments:
BAC sequences submitted to GenBank were modified by deletion of vector sequences at the 5' and 3' end as follows:

| BAC | Accession# | Removed from 5' end | Removed from 3' end |
|---|---|---|---|
| 38A2 | AY386694 | 1-125 | 128185-128225 |
| 219D23 | AY386695 | 1-54 | 137357-137389 |
| Fos15B* | AY3866968 | 1-97 | 33395-33427 |
| 179L1 | AY495827 | 0 | 205145-205968 |
| 196O2 | AY495828 | 1-32 | 178117-178171 |

*In addition contigs in GenBank are separated by 50 nt. In the Fos15B sequence submitted with the provisional application contigs were separated by 10 nt.

TABLE 2

| ID | Region | Sequence |
|---|---|---|
| 193 | $V_H1$ | 5'CGCGGATCCGAGACTGGGCTGCGCTG3' |
| 194 | $V_H1$ | 5'CGCAAGCTTGAAATAGGTGGCCGTGTC3' |
| 195 | $J_H$ | 5'CGCGGATCCAGGCACCCTGGTCACCG3' |
| 196 | $J_H$ | 5'CGCAAGCTTGTGACCAGGGTGCCCTG3' |
| 197 | Cγ | 5'CGCGGATCCCTGGAGCCGAAGGTCTAC3' |
| 198 | Cγ | 5'CGCAAGCTTGAGATGGACTTCTGCGTG3' |
| 199 | 3' Enh | 5'CGCGGATCCCAGAGTGGGTCTGTGACA3' |
| 200 | 3' Enh | 5'CGCAAGCTTACAGGCGCATGCAAATGC3' |
| 201 | Vκ | 5'CGCGGATCCGAGGCACAGTCACCATC3' |
| 202 | Vκ | 5'CGCAAGCTTACAGTAGTAAGTGGCAGC3' |
| 203 | Jκ | 5'CGCGGATCCGGAGGGACCGAGGTGGT3' |
| 204 | Jκ | 5'CGCAAGCTTACCATGGTCCCTGAGCC3' |
| 205 | C□ | 5'CGCGGATCCCCTCAGGTGATCCAGTTG3' |
| 206 | C□ | 5'CGCAAGCTTCTATTGAAGCTCTGGACG3' |
| 207 | K 3' Enh | 5'CGCGGATCCGTGACTGGCCCAAGAAG3' |
| 208 | K 3' Enh | 5'CGCAAGCTTATACAACCTTGGCCAGG3' |
| 209 | C□ | 5'AAACAGCTTTTCACACCTCCCCTTTCTCTCTTTGCTCCCCTGGGCCCTCAGGGAGTGCATCCGCCCCAACCCTTTTCC3' |
| 210 | C□ | 5'CAGGGTTAGTTTGCATGCACACACACAGCGCCTGGTCACCCAGAGGGGTCAGTAGCAGGTGCCAGCTGTGTCGGACATG3' |
| 211 | C□ | 5'GGTCAGGGGTCCTCCAGGGCAGGGGTCACATTGTGCCCCTTCTCTTGCAGCCTCCACCAAGGGCCCATCGGTC3' |
| 212 | Cγ | 5'CACAGCTGCGGCGTGGGGGGGAGGGAGAGGGCAGCTCGCCGGCACAGCGCTCATTTACCCGGAGACAGGGAGAGGCTCTTC3' |
| 213 | $J_H$ | 5'GTGTTATAAAGGGAGACTGAGGGGGCAGAGGCTGTGCTACTGGTACCTGGCTGAATACTTCCAGCACTGGGGCCAGG3' |
| 214 | $J_H$ | 5'GGCCACAGAAAAGAGGAGAGAATGAAGGCCCCGGAGAGGCCGTTCCTACCTGAGGAGACGGTGACCGTGGTCCCT TG-3' |
| 215 | Genta | 5'CCAGGCCGGCCTGGAGTTGTAGATCCTCTACG3' |
| 216 | Genta | 5'CCAGGCGCGCCAAGATGCGTGATCTGATCC3' |

TABLE 2-continued

| ID | Region | Sequence |
|---|---|---|
| 217 | Linker | 5'GGCCGCGGCCGGCCATCGATGGCGCGCCTTCGAAACGCGTA3' |
| 218 | Linker | 5'AGCTTACGCGTTTCGAAGGCGCGCCATCGATGGCCGGCCGC3' |
| 219 | pBB11.1 | 5'ATTCCCAAGCTTTTAATTAAGACGTCAGCTTCCTTAGCTCCTG3' |
| 220 | pBB11.1 | 5'ATTCGCGGATCCACGCGTTTCGTTCCCAAAGGCGCGCCTAGCGATGAGCTCGGAC3' |
| 221 | Neo | 5'GCAGGCATGCAAAGCTTATTACACCAGTGTCAGTAAGCG3' |
| 222 | Neo | 5'GGTACCCGGGGATCCTCAGAAGAACTCGTCAAGAAGGCG3' |
| 223 | pBB11.2 | 5'AAATTCCCTTAATTAAGACGTCAGCTTCCTTAGCTCCTG3' |
| 224 | pBB11.2 | 5'GAAACCGGGGACGCGTTACCGTTCGTATAATGTATGCTATACGAAGTTATGCGGCCGCTAGCGATGAGCTCGGAC3' |
| 225 | CA | 5'TTCTCTGTTTTTGTCCGTGGAATGAACAATGGAAGTCCGAGCTCATCGCTAAGGGCACCAATAACTGC3' |
| 226 | CA | 5'CACAGGAGAGAAACAGGACCTAGAGGATGAGGAAGTCCCTGTAGGCTTCCTACCGTTCGTATAATGTATGCTATACGAAGTTATTACCTGTGACGGAAGATC-3' |
| 227 | $V_H3$-9 | 5'ATAGAGAGATTGAGTGTG3' |
| 228 | $V_H3$-9 | 5'TCCTGTCTTCCTGCAG3' |
| 229 | $V_H3$-11 | 5'AGAGACATTGAGTGGAC3' |
| 230 | $V_H3$-11 | 5'AGGGAGGTTTGTGTC3' |
| 231 | $V_H3$-13 | 5'ACTAGAGATATTGAGTGTG3' |
| 232 | $V_H3$-13 | 5'AGGCATTCTGCAGGG3' |
| 233 | $V_H3$-15 | 5'ACTAGAGAGATTAAGTGTG3' |
| 234 | $V_H3$-15 | 5'TCACACTGACCTCCC3' |
| 235 | $V_H3$-20 | 5'TCATGGATCAATAGAGATG3' |
| 236 | $V_H3$-20 | 5'TGCAGGGACGTTTGTG3' |
| 237 | $V_H3$-23 | 5'AGAAAAATTGAGTGTGAA3' |
| 238 | $V_H3$-23 | 5'GTGTCTGGGCTCACAA3' |
| 239 | $V_H3$-30 | 5'AGAGAGACTGAGTGTG3' |
| 240 | $V_H3$-30 | 5'TGCAGGGAGGTTTGTG3' |
| 241 | $V_H3$-43 | 5'TGAGTGTGAGTGAACATG3' |
| 242 | $V_H3$-43 | 5'ACCAGCTCTTAACCTTC3' |
| 243 | $V_H3$-64 | 5'TGAGTGTGAGTGGAC3' |
| 244 | $V_H3$-64 | 5'TGACGCTGATCAGTG3' |
| 245 | $V_H3$-66 | 5'TCTGACCAATGTCTCTG3' |
| 246 | $V_H3$-66 | 5'AGGTTTGTGTCTGGGC3' |
| 247 | $V_H3$-72 | 5'ACAAGGTGATTTATGGAG3' |
| 248 | $V_H3$-72 | 5'AGGTTTGTGTCCGGG3' |
| 249 | $V_H3$-9 | 5'TTGGCGCGCC TGTCGTCTGTGTTTGCAG GTGTCC3' |
| 250 | $V_H3$-9 | 5'TTGCACGCGTGCAGGGAGGTTTGTGTCTGGGCTCAGCCTGAGGGCCCCTCACTGTGTCATCTTTTGCAC3' |
| 251 | $V_H3$-11 | 5'TTGGCGCGCC TGTCGTCTGTGTTTGCAG GTGTCC3 |
| 252 | $V_H3$-11 | 5'TTGCACGCGTGCAGGGAGGTTTGTGTCTGGGCTCAGCCTGAGGGCCCCTCACTGTGTCTCTCG3' |

TABLE 2-continued

| ID | Region | Sequence |
|---|---|---|
| 253 | $V_H3-13$ | 5'TTGGCGCGCCTGTCGTCTGTGTTTGCAGGTGTCC3' |
| 254 | $V_H3-13$ | 5'TTGCACGCGTGCAGGGAGGTTTGTGTCTGGGCTCAGCCTGAGGGCCCCTCACTGTGTCTCTTG3' |
| 255 | $V_H3-15$ | 5'TTGGCGCGCCTGTCGTCTGTGTTTGCAGGTGTCC3' |
| 256 | $V_H3-15$ | 5'TTGCACGCGTGCAGGGAGGTTTGTGTCTGGGCTCAGCCTGAGGGCCCCTCACTGTGTCTGTGG3' |
| 257 | $V_H3-20$ | 5'TTGGCGCGCC TGTCGTCTGTGTTTGCAGGTGTC3' |
| 258 | $V_H3-20$ | 5'TTGCACGCGTGCAGGGAGGTTTGTGTCTGGGCTCAGCCTGAGGGCCCCTCACTGTGTCTCTC3' |
| 259 | $V_H3-23$ | 5'TTGGCGCGCCTGTCGTCTGTGTTTGCAG GTGTCCAGTGTG3' |
| 260 | $V_H3-23$ | 5'TTGCACGCGTGCAGGGAGGTTTGTGTCTGGGCTCAGCCTGAGGGCCCCTCACTGTGTCTTTC3' |
| 261 | $V_H3-30$ | 5'TTGGCGCGCCTGTCGTCTGTGTTTGCAGGTGTCCAGTGTC3' |
| 262 | $V_H3-30$ | 5'TTGCACGCGTGCAGGGAGGTTTGTGTCTGGGCTCAGCCTGAGGGCCCCTCACTGTGTCTTTCG3' |
| 263 | $V_H3-43$ | 5'TTGGCGCGCCTGTCGTCTGTGTTTGCAGGTGTCC3' |
| 264 | $V_H3-43$ | 5'TTGCACGCGTGCAGGGAGGTTTGTGTCTGGGCTCAGCCTGAGGGCCCCTCACTGTGTCTCTTTTGCAC3' |
| 265 | $V_H3-64$ | 5'TTGGCGCGCCTGTCGTCTGTGTTTGCAGGTGTCC3' |
| 266 | $V_H3-64$ | 5'TTGCACGCGTGCAGGGAGGTTTGTGTCTGGGCTCAGCCTGAGGGCCCCTCACTGTGTCTCTCGCAC3' |
| 267 | $V_H3-66$ | 5'TTGGCGCGCCTGTCGTCTGTGTTTGCAGGTGTCC3' |
| 268 | $V_H3-66$ | 5'TTGCACGCGTGCAGGGAGGTTTGTGTCTGGGCTCAGCCTGAGGGCCCCTCACTGTGTCTCCG3' |
| 269 | $V_H3-72$ | 5'TTGGCGCGCCTGTCGTCTGTGTTTGCAG GTTTCC3' |
| 270 | $V_H3-72$ | 5'TTGCACGCGTGCAGGGAGGTTTGTGTCTGGGCTCAGCCTGAGGGCCCCTCACTGTGTCTCTAGCAC3' |
| 271 | V1-2 | 5'TTGGCGCGCCAGGGGAGTGCGGCTCCAC3' |
| 272 | V1-2 | 5'TTGCACGCGT TGGTCAGGACACTGTCACTCAC3' |
| 273 | V2-3 | 5'TTGGCGCGCCAGGGGCGCGCGGCTCCAC3' |
| 274 | V2-3 | 5'TTGCACGCGTTGATCACGAAACTGTCACTCACACTCTC3' |
| 275 | V3-4 | 5'TTGGCGCGCCAGGGGCGCGCGGCTCCAC3' |
| 276 | V3-4 | 5'TTGCACGCGTTCTGTTGGTCTCTTCTTCTCTTGCTATAAC3' |
| 277 | V4-5 | 5'TTGGCGCGCCAGGGGAGTGCGGCTCCAC3' |
| 278 | V4-5 | 5'TTGCACGCGTTGGTCAAGACACTGTCACTCAC3 |
| 279 | V5-6 | 5'TTGGCGCGCCAGGGACGCACGGCTCCAC3' |
| 280 | V5-6 | 5'TTGCACGCGTTGGTCAGGAAGCTGTCACTCAC3' |
| 281 | V6-7 | 5'TTGGCGCGCCAGGGATGCGCGGCTCCAG3' |
| 282 | V6-7 | 5'TTGCACGCGTTGGTCAGGACACTGTCACTGACAC3' |
| 283 | V7-8 | 5'TT GGCGCGCCAGGGGAGTGCGGCTCCAC3' |
| 284 | V7-8 | 5'TTGCACGCGTTGGTCAGGAAGCTGTCACTCACTCTC3' |
| 285 | V21-22 | 5'TTGGCGCGCCGGGGCCCGCGGCTCCAC3' |
| 286 | V21-22 | 5'TTGCACGCGTTGGTCAGGAAGCTGTCAC3' |

TABLE 2-continued

| ID | Region | Sequence |
|---|---|---|
| 287 | V22-23 | 5'TTGGCGCGCCAGGGACGTGAGGCTCTAC3' |
| 288 | V22-23 | 5'TTGCACGCGTTGGTCAGGGCACTGTCAC3' |
| 289 | Linker | 5'GGCCGCGGCCGGCCATCGATGGCGCGCC TTCGAAACGCGTA3' |
| 290 | Linker | 3'CGCCGGCCGGTAGCTACCGCGCGGAAGCTT TGCGCATTCGA5' |
| 291 | Linker | 5'CGG CCG GCC ATC GAT GGC GCG CCT TCG AAA CGC GTG GTA C3' |
| 292 | Linker | 3'TCG AGC CGG CCG GTA GCT ACC GCG CGG AAG CTT TGC GCA C5' |
| 293 | Genta | 5'CCAGGCCGGCCTGGAGTTGTAGATCCTCTACG3' |
| 294 | Genta | 5'CCAGGCGCGCCAAGATGCGTGATCTGATCC-3' |
| 295 | Neo | 5'CCAGGCCGGCCATTACACCAGTGTCAGTAAGCG3' |
| 296 | Neo | 5'CCAGGCGCGCCTCAGAAGAACTCGTCAAGAAGGCG3' |
| 297 | Linker | 5'GAT CCG GCC GGC CAT CGA TGG CGC GCC TTC GAA ACG CGT TAG GGA TAA CAG GGT AAT A3' |
| 298 | Linker | 3'GCC GGC CGG TAG CTA CCG CGC GGA AGC TTT GCG CAA TCC CTA TTG TC CCA TTA TCGA5' |
| 299 | Neo | 5'ATCTGCACTCAGTGCGTCTTGAGCGCCCCCTGGTAGAGCCG CGCGACCCT GGCGCGCC ATTACACCAGTGTCAGTAAGCG3' |
| 300 | Neo | 5'AAATGACCAGTCTGACAGCCGCGGACACGGCCACCTATTTC TGTGCGAGA GGCCGGCC TCAGAAGAACTCGTCAAGAAGGCG3' |
| 301 | Cκ Km3 | 5'GATGTCCACTGGTACCTAAGCCTCGCCCTCTGTGCTTCTTCCCTC CTCAGGAACTGTGGCTGCACCATCTGTCTTC3' |
| 302 | Cκ Km3 | 5'GAGGCTGGGCCTCAGGGTCGCTGGCGGTGCCCTGGCAGGCGTC TCGCTCTAACACTCTCCCCTGTTGAAGCTCTTTGTG3 |
| 303 | Neo | 5'CTTTCTCTGTCCTTCCTGTGCGACGGTTACGCCGCTCCATGAGCTT ATCGTAACTATAACGGTCCTAAGGTAGCGATGGACAGCAAGCGAA CCGGA3' |
| 304 | Neo | 5'GGACCAGTTTACAATCCCACCTGCCATCTAAGAAAGCTGGTCTCA TCGTGTCAGAAGAACTCGTCAAGAAG3' |
| 305 | Zeo | 5'CCCCCCCCGCCACTTCTCTTTCTGTTTCGTTTAAGTTCTACACTGAC ATACTAGGGATAACAGGGTAATAACGTTTACAATTTCGCCTGATG3 |
| 306 | Zeo | 5'AGTGGGTAGGCCTGGCGGCCGCCTGGCCGTCGACATTTAGGTGA CACTATAGAAGGATCCTAGCACGTGTCAGTCCTGCT3' |
| 307 | Genta | 5'TTACGCCAAGCTATTTAGGTGACACTATAGAATACTCAAGCTTTG ATTGCTAACTATAACGGTCCTAAGGTAGCGATGAAGGCACGAACCC AGTTG3' |
| 308 | Genta | 5'GCGGAATTCTATGTCTAGTGGAGGGTGAAGCTGGTGATTATAGA GTGAAAATTACCCTGTTATCCCTATCGGCTTGAACGAATTGTTAG3' |
| 309 | VJ | 5'CATAAATATACTGTCTTCCAGGATCTTAGAGCTCACCTAAGGAAA CAAGAGTTCATTTGAAGTTTTTAAAGTG3' |
| 310 | VJ | 5'ACTCCAGAAGTTCCTATACTTTCTAGAGAATAGGAACTTCGGAAT AGGAACTTCCTTTGATCTCCACCTTGGTC3' |
| 311 | Genta | 5'GAAGTTCCTATTCCGAAGTTCCTATTCTCTAGAAAGTATAGGAAC TTCTGGAGTTGTAGATCCTCTACG3' |
| 312 | Genta | 5'AAAACAAACCAATCAGGCAGAAACGGTGAGGAATCAGTGAAAC GGCCACTTACGAAGTTCCTATACTTTCTAGAGAATAGGAACTTCGG AATAGGAACTTCAAGATGCGTGATCTGATCC3' |
| 313 | FRT | 5'TTATGCTGCATCCAGTTTGC3' |
| 314 | FRT | 5'AAAACAAACCAATCAGGCAG3' |
| 315 | FRT | 5'TGTGACATCCAGATGAC3' |

TABLE 2-continued

| ID | Region | Sequence |
|---|---|---|
| 316 | FRT | 5'AAAACAAACCAATCAGGCAG3' |
| 317 | Genta | 5'GGACCAGTTTACAATCCCACCTGCCATCTAAGAAAGCTGGTCTCATCGTGGTGCCAGGGCGTGCCCTTGGGCTGGGGGCGCGATAACTTCGTATAGCATACATTATACGAAGTTATCGATCGTGGAGTTGTAGATCCTCTACG3' |
| 318 | Genta | 5'TTACGCCAAGCTATTTAGGTGACACTATAGAATACTCAAGCTTTGATTGCAAGATGCGTGATCTGATCCT3' |
| 319 | Linker | 5'CGGGATCCGCGCGTACGGAAGTTCCTATACCTTTTGAAGAATAGGAACTTCGGAATAGGAACTTCATTACACCAGTGTCAGTAAGCG3' |
| 320 | Linker | 5'GGGAAGCTTCGCGCGATCGCCGCTTTCGCAAAGGCGCGCCTCAGAAGAACTCGTCAAGAAGGCG3' |
| 321 | Genta | 5'GGCGGCCGCCTGGCCGTCGACATTTAGGTGACACTATAGAAGGATCCGCGTGGAGTTGTAGATCCTCTACG3' |
| 322 | Genta | 5'AACTCAGTAAGGAAAAGGACTGGGAAAGTGCACTTACATTTGATCTCCAGGCGCGCCAAGATGCGTGATCTGATCC3' |
| 323 | Neo | 5'GGACCAGTTTACAATCCCACCTGCCATCTAAGAAAGCTGGTCTCATCGTGGTGCCAGGGCGTGCCCTTGGGCTGGGGGCGCGGAAGTTCCTATTCCGAAGTTCCTATTCTTCAAAAGGTATAGGAACTTCCGTACGATTACACCAGTGTCAGTAAGCG3' |
| 324 | Neo | 5'GGACTGATGGGAAAATAGAGGAGAAAATTGACCAGAGGAAGTGCAGATGGTCAGAAGAACTCGTCAAGAAGGCG3' |
| 325 | RSS | 5'AACCTGAAGATTTTGCAACTTACTACTGTCAACAGAGTTACAGTACCCCTTCCACAGTGATACAAGCCC3' |
| 326 | RSS | 5'TGCCGGCCACGATGCGTCCGGCGTAGAGGATCTACAACTCCAGGCGCGCCTGGTCATGTCAGTGCTGCTGC3' |
| 327 | Genta | 5'CTCCTTTCCTCCTCCTTGGTGGCAGCAGCACTGACATGACCAGGCGCGCC TGGAGTTGTAGATCCTCTACG3' |
| 328 | Genta | 5'TGTAATACGACTCACTATAGGGCGAATTCGAGCTCGGTACCCGGGGATCCCGTACGAAGATGCGTGATCTGATCC3' |
| 329 | Kana | 5'GGCGGCCGCCTGGCCGTCGACATTTAGGTGACACTATAGAAGGATCCGCGACCCTGTTATCCCTAGATTTAAATGATATCGG3' |
| 330 | Kana | 5'AACTTTCTCCTACAGATCCCAGATAACCATGAATTTATTACACCATCTTGGGCGCGCCAAGTTCCTATACTTTCTAGAGAATAGGAACTTCGGAATAGGAACTTCAGTTGGTGATTTTGAACTTTTGCTTTGCC3' |
| 331 | Amp | 5'GGACCAGTTTACAATCCCACCTGCCATCTAAGAAAGCTGGTCTCATCGTGGTGCCAGGGCGTGCCCTTGGGCTGGGGGCGCGGCGATCGCAAGTTCCTATTCCGAAGTTCCTATTCTTCAAAAGGTATAGGAACTTCTACGGGGTCTGACGCTCAG3' |
| 332 | Amp | 5'GAATTCAGAGCTCAATGAGTTGCCTTGTTCAGAGCTCTATTTTCACTTGACGTACGACAGACAAGCTGTGACCGTC3' |
| 333 | J Region | 5'GAGTTAGGCCTCAGAGCTGAGGCAGGGCTCGGTTCCCCTTGGGTGAGAAGGGTTTCTGTTCAGCAAGAC3' |
| 334 | J Region | 5'TGGCCAATTAGAGCAAAATTTCAGACAGTAATAGGAAAAGGTACTTACGTTTAATCTCCAGTCGTGTC3' |
| 335 | O2 | 5'TCAGTACTGACTGGAAC3' |
| 336 | O2 | 5'CCAATGACTTTCAAAACC3' |
| 337 | L8 | 5'CCGTACAGCCTGGCTC3' |
| 338 | L8 | 5'AACACCATCAGAGTGTGC |
| 339 | L4 | 5'ATGATTAATTGTGTGGACC3' |
| 340 | L4 | 5'AGGTGATCTCATATCCTC3' |
| 341 | A30 | 5'CTCAGTACTGCTTTACTG3' |

TABLE 2-continued

| ID | Region | Sequence |
|---|---|---|
| 342 | A30 | 5'TGACTTCATGTCCCCTTC3' |
| 343 | L11 | 5'ACATGATTAATTGTGTGGACC3' |
| 344 | L11 | 5'GGTGCAGAGGTGACTTCG3' |
| 345 | L1 | 5'CTCAGTACTGCTTTACTATTC3' |
| 346 | L1 | 5'GAGGAACACTCTCAGCTG3' |
| 347 | L5 | 5'CAGGGAACTTCTCTTACAG3' |
| 348 | L5 | 5'GAATTAGGGTGCAGAGGC3' |
| 349 | L15 | 5'TACTATTCAGGGAAATTC3' |
| 350 | L15 | 5'TGTCTGTGAAGTTGGTG3' |
| 351 | O8 | 5'TGGCTCTTGATGGAAGC3' |
| 352 | O8 | 5'ACTTCAAAGTGTGACTGC3' |
| 353 | L19 | 5'AGGGAACTTCTCTTACAGC3' |
| 354 | L19 | 5'AATTAGGGTGCAGAGGCG3' |
| 355 | L12 | 5'GAAGTCTTCCTATAATATGATC3' |
| 356 | L12 | 5'TGGCTGCATCTGAGGACC3' |
| 357 | A20 | 5'GCCACTAATGCCTGGCAC3' |
| 358 | A20 | 5'CTGCTGTCAGCAGAGGGC3' |
| 359 | O4 | 5'CTTCTTATAACATGATGG3' |
| 360 | O4 | 5'AAACGCTCTGAGCAGC3' |
| 361 | L14 | 5'CTCAGTACTGCTTTACTG3' |
| 362 | L14 | 5'GAGGAACAATCTCAGCCG3' |
| 363 | L23 | 5'AGCCAGGCTGTACGGAAC3' |
| 364 | L23 | 5CCCAGCCTCACACATCTC3' |
| 365 | L9 | 5'TGGCCCTTCAGGGAAG3' |
| 366 | L9 | 5'ACCATCAGAGTGTGGTTG3' |
| 367 | A4 | 5'CCAGTGTAGCCATTAATG3' |
| 368 | A4 | 5'TACCAAAACTTCCCAGGG3' |
| 369 | L24 | 5'GGGAAATTCTCTTACTAC3 |
| 370 | L24 | 5'CCCCCTCTACCAATAC3' |
| 371 | O6 | 5'CCATTCAGGGAAGTCTTC3' |
| 372 | O6 | 5'TGAGTCTGAGAAGTGTTG3' |
| 373 | L22 | 5'GGAATTTTCTTAGCCCAC3' |
| 374 | L22 | 5'ATGTTCAGGCTTGTAACC3' |
| 375 | A9 | 5'TCATCTTACAAATAGTTG3' |
| 376 | A9 | 5'TCTGACCATTCCTGC3' |
| 377 | A25 | 5'GGGAAATCATCTTATAAATAG3' |
| 378 | A25 | 5'TGCAGATGAGACTTCTGG3' |
| 379 | A15 | 5'ATTCAGGAAAGTCCTCTC3' |
| 380 | A15 | 5'CAGTGACCTTCAGAGTG3' |

TABLE 2-continued

| ID | Region | Sequence |
|---|---|---|
| 381 | O9 | 5'ATTCAGGAAAGTCCTCTC3' |
| 382 | O9 | 5'CAGTGACCTTCAGAGTG3' |
| 383 | O2 | 5'TTGGCGCGCCTTCTGTTTCCCTTCTCAGGTGCCAGATGTGACATC |
| 384 | O2 | 5'CGCACGCGTGTTTGATCTCCACCTTGGTCCCTCCGCCGAAAGTGAGAGGGGTACTGTAACTCTGTTG3' |
| 385 | L8 | 5'TTGGCGCGCCTTCTGTTTCCCTTCTCAGGTGCCAGATGTGACATC |
| 386 | L8 | 5'CGCACGCGTCCTGGGGGGTTTTTGTTAGGGCTTGTATCACTGTGGGAGGGTAACTATTAAG3' |
| 387 | L4 | 5'TTGGCGCGCCTTCTGTTTCCCTTCTCAGGTGCCAGATGTGCCATC |
| 388 | L4 | 5'CGCACGCGTCCTGGGGGGTTTTTGTTAGGGCTTGTATCACTGTGGGAGGGTAACTATTAAAC3' |
| 3897 | A30 | 5'TTGGCGCGCCTTCTGTTTCCCTTCTCAGGTGCCAGGTGTGACATC3' |
| 390 | A30 | 5'CGCACGCGTCCTGGGGGGTTTTTGTTAGGGCTTGTATCACTGTGGGAGGGTAACTATTATGC3' |
| 391 | L11 | 5'TTGGCGCGCCTTCTGTTTCCCTTCTCAGGTGCCAGATGTGCCATC3' |
| 392 | L11 | 5'CGCACGCGTCCTGGGGGGTTTTTGTTAGGGCTTGTATCACTGTGGGAGGGTAATTGTAATC3' |
| 393 | L1 | 5'TTGGCGCGCCTTCTGTTTCCCTTCTCAGGTGCCAGATGTGACATC3' |
| 394 | L1 | 5'CGCACGCGTCCTGGGGGGTTTTTGTTAGGGCTTGTATCACTGTGGGAGGGTAACTATTATAC3' |
| 395 | L5 | 5'TTGGCGCGCCTTCTGTTTCCCTTCTCAGGTTCCAGATGCGACATC3' |
| 396 | L5 | 5'CGCACGCGTCCTGGGGGGTTTTTGTTAGGGCTTGTATCACTGTGGGAGGGAAACTGTTAG3' |
| 397 | L15 | 5'TTGGCGCGCCTTCTGTTTCCCTTCTCAGGTGCCAGATGTGACATC |
| 398 | L15 | 5'CGCACGCGTCCTGGGGGGTTTTTGTTAGGGCTTGTATCACTGTGGGAGGGTAACTATTATAC3' |
| 399 | O8 | 5'TTGGCGCGCCTTCTGTTTCCCTTCTCAGGTGCCAGATGTGACATC |
| 400 | O8 | 5'CGCACGCGTCCTGGGGGGTTTTTGTTAGGGCTTGTATCACTGTGGGAGGGAGATTATCATAC3' |
| 401 | L19 | 5'TTGGCGCGCCTTCTGTTTCCCTTCTCAGGTTCCAGATGCGACATC3' |
| 402 | L19 | 5'CGCACGCGTCCTGGGGGGTTTTTGTTAGGGCTTGTATCACTGTGGGAGGGAAACTGTTAG3' |
| 403 | L12 | 5'TTGGCGCGCCTTCTGTTTCCCTTCTCAGGTGCCAAATGTGACATC3' |
| 404 | L12 | 5'CGCACGCGTCCTGGGGGGTTTTTGTTAGGGCTTGTATCACTGTGGGAGAATAACTATTATAC3' |
| 405 | A20 | 5'TTGGCGCGCCTTCTGTTTCCCTTCTCAGATACCAGATGTGACATCC3' |
| 406 | A20 | 5'CGCACGCGTCCTGGGGGGTTTTTGTTAGGGCTTGTATCACTGTGGGAGGGGCACTGTTATAC3' |
| 407 | O4 | 5'TTGGCGCGCCTTCTGTTTCCCTTCTCAGGTGCCAGATGTGACATC3' |
| 408 | O4 | 5'CGCACGCGTCCTGGGGGGTTTTTGTTAGGGCTTGTATCACTGTGGGAGGGGCATTGTAAG3' |
| 409 | L14 | 5'TTGGCGCGCCTTCTGTTTCCCTTCTCAGGTGCCAGATGTAACATCC3' |
| 410 | L14 | 5'CGCACGCGTCCTGGGGGGTTTTTGTTAGGGCTTGTATCACTGTGGGAGGGTAACTATTATGC3' |
| 411 | L23 | 5'TTGGCGCGCCTTCTGTTTCCCTTCTCAGGTGCCAGATGTGCCATC3' |

TABLE 2-continued

| ID | Region | Sequence |
|---|---|---|
| 412 | L23 | 5'CGCACGCGTCCTGGGGGGTTTTTGTTAGGGCTTGTATCACTGTGGGAGGGGTACTATAATAC3' |
| 413 | L9 | 5'TTGGCGCGCCTTCTGTTTCCCTTCTCAGGTGCCAGATGTGCCATC3' |
| 414 | L9 | 5'CGCACGCGTCCTGGGGGGTTTTTGTTAGGGCTTGTATCACTGTGGGAGGGTAACTATAATAC3' |
| 415 | A4 | 5'TTGGCGCGCCTTCTGTTTCCCTTCTCAGATACCAGATGTGACATCC3' |
| 416 | A4 | 5'CGCACGCGTCCTGGGGGGTTTTTGTTAGGGCTTGTATCACTGTGGGAGGGGCACTGTTATAC3' |
| 417 | L24 | 5'TTGGCGCGCCTTCTGTTTCCCTTCTCAGGTGCCAGATGTGTCATC3' |
| 418 | L24 | 5'CGCACGCGTCCTGGGGGGTTTTTGTTAGGGCTTGTATCACTGTGGGAGGGAAACTATAATAC3' |
| 419 | O6 | 5'TTGGCGCGCCTTCTGTTTCCCTTCTCAGGGACCAGAAGTGACATC3' |
| 420 | O6 | 5'CGCACGCGTCCTGGGGGGTTTTTGTTAGGGCTTGTATCACTGTGGGAGGGTAATTTTTATAC3' |
| 421 | L22 | 5'TTGGCGCGCCTTCTGTTTCCCTTCTCAGGTGTCAGATTTGACATCC3' |
| 422 | L22 | 5'CGCACGCGTCCTGGGGGGTTTTTGTTAGGGCTTGTATCACTGTGGGAGGGTAACTGAAGTC3' |
| 423 | A9 | 5'TTGGCGCGCCTTCTGTTTCCCTTCTCAGGAGTCAGATGTGATTTCC3' |
| 424 | A9 | 5'CGCACGCGTCCTGGGGGGTTTTTGTTAGGGCTTGTATCACTGTGGGATGGCTGCTGTAAG3' |
| 425 | A25 | 5'TTGGCGCGCCTTCTGTTTCCCTTCTCAGGAGTCAGATGTGATTTCC3' |
| 426 | A25 | 5'CGCACGCGTCCTGGGGGGTTTTTGTTAGGGCTTGTATCACTGTGGGATGGCTGCTGTAAG3' |
| 427 | A15 | 5'TTGGCGCGCCTTCTGTTTCCCTTCTCAGGTGCCAGATATGACATGC3' |
| 428 | A15 | 5'CGCACGCGTCCTGGGGGGTTTTTGTTAGGGCTTGTATCACTGTGGGAGGGTCACTTTTATAC3' |
| 429 | O9 | 5'TTGGCGCGCCTTCTGTTTCCCTTCTCAGGTGCCAGATATGACATGC3' |
| 430 | O9 | 5'CGCACGCGTCCTGGGGGGTTTTTGTTAGGGCTTGTATCACTGTGGGAGGGTCACTTTTATAC3' |
| 431 | V7-8 | 5'TTGGCGCGCC GGAGGAAACAGAAACACAG3' |
| 432 | V7-8 | 5'CGCACGCGT CAGCTGCTCGTCCTGGG3' |
| 433 | V11-10 | 5'TTGGCGCGCC GGAGGGAAACAGAAACAC3' |
| 434 | V11-10 | 5'CGCACGCGTAGCTGCTCCTCCTGGG3' |
| 435 | V15-14 | 5'TTGGCGCGCC GAAGGGAAACAGAAACACAG3' |
| 436 | V15-14 | 5'CGCACGCGTAGCTGCTCCTCCTGGG3' |
| 437 | V18-17 | 5'TTGGCGCGCC GAGGGAAACAGAAACAC3' |
| 438 | V18-17 | 5'CGCACGCGTCAGCTGCTGCTCCTGGG3' |
| 439 | V19-18 | 5'TTGGCGCGCC GAAGGGAAACAGAAACACAG3' |
| 440 | V19-18 | 5'CGCACGCGT AGCTGCTCCTCCTGGG3' |
| 441 | V20-19 | 5'TTGGCGCGCC GAGGAGGGAAACAGAAACAC3' |
| 442 | V20-19 | 5'CGCACGCGTCAGCTGCCCCTCCTGGG3' |
| 443 | V21-20 | 5'TTGGCGCGCC GGAGGAAACAGAAACACAG3' |
| 444 | V21-20 | 5'CGCACGCGTCCCTAGCTGCTCCTGGG3' |

TABLE 2-continued

| ID | Region | Sequence |
|---|---|---|
| 445 | V24-23 | 5'TTGGCGCGCC GGAGGGAAACAGACACAC3' |
| 446 | V24-23 | 5'CGCACGCGTCAGCTGCTCCTCCTGGC3' |
| 447 | V26-25 | 5'TTGGCGCGCC GAAGGGAAAGAGAAACACAG3' |
| 448 | V26-25 | 5'CGCACGCGTAGCTGCTCCTCCTGGG3' |
| 449 | V27-26 | 5'TTGGCGCGCC GGAGGGAAACAGAAACAC3' |
| 450 | V27-26 | 5'CGCACGCGTCCCAGCTGCTCCTGGG3' |
| 451 | Genta | 5'AGCTCGGTACCCGGGGATCCTCTAGAGTCGACCTGCAGGCATGCAAGCTTGGCCGGCCTGGAGTTGTAGATCCTCTACG3' |
| 452 | Genta | 5'AAAACAAACCAATCAGGCAGAAACGGTGAGGAATCAGTGAAACGGCCACTTACGGCGCGCCAAGATGCGTGATCTGATCC3' |
| 453 | Hygro | 5'CGTTGGACCAGTTTACAATCCCACCTGCCATCTAAGAAAGCTGGTCTCATATAACTTCGTATAATGTATGCTATACGAACGGTAACGCGTGAAGTTCCTATTCCGAAGTTCCTATTCTCTAGAAAGTATAGGAACTTCTCAGAGCAGATTGTACTG3' |
| 454 | Hygro | 5'GGACAGCAAGCGAACCGGAATTGCCAGCTGGGGCGCCCTCTGGTAAGGTTAAGATGCGTGATCTGATCC3' |
| 455 | | 5'ACTGCACCTCAGCGTCCCCCTGCCCATGTCAGGGCCGATGAAGGGCACAGCGTACGATTACACCAGTGTCAGTAAGCG3' |
| 456 | | 5'TGTAATACGACTCACTATAGGGCGAATTGAGCTCGGTACCCGGGGATCCTGCGATCGCTCAGAAGAACTCGTCAAGAAGGCG3' |
| 457 | $J_H$ | 5'GTGTTATAAAGGGAGACTGAGGGAGGCAGAGGCTGTGCTACTGGTACCTGGCTGAATACTTCCAGCACTGGGGCCAGG3' |
| 458 | $J_H$ | 5'GGCCACAGAAAAGAGGAGAGAATGAAGGCCCCGGAGAGGCCGTTCCTACCTGAGGAGACGGTGACCGTGGTCCCTTG3' |
| 459 | Spacer | 5'AACAACCTCAGGGCTGAGGACACC3' |
| 460 | Spacer | 5'CTGCCCGTTGTCCCTCGAGATGGTGGCACGGCC3' |

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08652842B2). An electronic copy of the "Sequence Listing" will also be available from the USPTO upon request and payment of the fee set forth in 37 CFR 1.19(b)(3).

What is claimed is:

1. A B cell from a transgenic rabbit, wherein said transgenic rabbit comprises a humanized immunoglobulin (Ig) locus comprising multiple Ig gene segments, present in a transgenic vector wherein:
    (a) at least one of said gene segments is a human Ig gene segment comprising two or more identical or different units consisting of, from 5' to 3' direction, a 5' nucleotide sequence, a human immunoglobulin heavy or light chain V gene segment, and a 3' nucleotide sequence, wherein said 5' nucleotide sequence and said 3' nucleotide sequence have the nucleotide sequence of SEQ ID NO: 35;
    (b) said gene segments are juxtaposed in an unrearranged, partially rearranged or fully rearranged configuration, and
    (c) said humanized Ig locus is capable of undergoing gene rearrangement, if necessary, and gene conversion and/or hypermutation, and producing a repertoire of humanized immunoglobulins in said transgenic rabbit.

2. The B cell of claim 1, wherein said transgenic rabbit preserves an essentially intact endogenous regulatory and antibody production machinery.

3. The B cell of claim 1 or claim 2, wherein said human Ig heavy chain V gene segment is a member of the VH3, VH1, VH5, or VH4 family.

* * * * *